(12) United States Patent
Glimcher et al.

(10) Patent No.: US 7,393,944 B2
(45) Date of Patent: Jul. 1, 2008

(54) T-BET COMPOSITIONS AND METHODS OF USE THEREOF

(75) Inventors: Laurie H. Glimcher, West Newton, MA (US); Susanne J. Szabo, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 371 days.

(21) Appl. No.: 10/008,264

(22) Filed: Dec. 3, 2001

(65) Prior Publication Data

US 2003/0104528 A1 Jun. 5, 2003

Related U.S. Application Data

(63) Continuation-in-part of application No. PCT/US00/15345, filed on Jun. 1, 2000.

(51) Int. Cl.
 *C07H 21/04* (2006.01)
 *C12N 15/00* (2006.01)
 *C12P 21/06* (2006.01)

(52) U.S. Cl. .................. 536/23.5; 435/320.1; 435/455; 435/69.1

(58) Field of Classification Search ................ 536/23.5, 536/23.1, 23.4, 24.31; 435/320.1, 70.1, 69.1, 435/325
See application file for complete search history.

(56) References Cited

U.S. PATENT DOCUMENTS

| | | | | |
|---|---|---|---|---|
| 5,844,082 | A | * 12/1998 | Kishimoto et al. | ........... 530/350 |
| 6,031,078 | A | 2/2000 | Khodadoust | ................. 530/350 |
| 2003/0186377 | A1 | * 10/2003 | Glimcher et al. | ........... 435/69.1 |

FOREIGN PATENT DOCUMENTS

| WO | WO 99/11783 A2 | 3/1999 |
|---|---|---|
| WO | WO 99/11783 A3 | 3/1999 |
| WO | WO 00/73453 A1 | 12/2000 |

OTHER PUBLICATIONS

Webster's New World Dictionary (Neufeldt and Guralnik, Eds.), Third College Edition, Ney York, 1988, p. 1080.*
Bulfone et al., 1995, Neuron, vol. 15: 63-78.*
Bulfone, et al. "*T-brain-1*: a Homolog of Brachyury whose Expression Defines Molecularly Distinct Domains within a Cerebral Cortex." *Neuron* 15(1):63-78 (Jul. 1995).
EMBL Acession No. AF093098 for *Homo sapiens* transcription factor TBLYM (TBLYM) mRNA, complete cds. Dec. 7, 2000.
Mullen, et al. "Role of T-bet in Commitment of $T_H1$ Cells Before IL-12-Dependent Selection." *Science* 292:1907-1910 (Jun. 2001).
Smith "T-box Genes: What They Do and How They Do It." *Trends Genet.* 15(4):154-158 (Apr. 1999).
Szabo, et al. "A Novel Transcription Factor, T-bet, Directs Th1Lineage Commitment." *Cell* 100:655-669 (Mar. 2000).
Zhang, et al. "Cloning and Characterization of a New Member of the T-Box Gene Family." *Genomics* 70(1):41-48 (2000).

* cited by examiner

*Primary Examiner*—G. R. Ewoldt
*Assistant Examiner*—Amy Juedes
(74) *Attorney, Agent, or Firm*—Lahive & Cockfield LLP; Giulio A. DeConti; Megan E. Williams

(57) ABSTRACT

Isolated nucleic acid molecules encoding T-bet, and isolated T-bet proteins, are provided. The invention further provides antisense nucleic acid molecules, recombinant expression vectors containing a nucleic acid molecule of the invention, host cells into which the expression vectors have been introduced and non-human transgenic animals carrying a T-bet transgene. The invention further provides T-bet fusion proteins and anti-T-bet antibodies. Methods of using the T-bet compositions of the invention are also disclosed, including methods for detecting T-bet activity in a biological sample, methods of modulating T-bet activity in a cell, and methods for identifying agents that modulate the activity of T-bet.

38 Claims, 27 Drawing Sheets

```
                          10         20         30         40         50         60
SEQ ID NO:2  HUMAN   MGIVEPGCGDMLTGTEPMPGSDEGRAPGADPQHRYFYPEPGAQDADERRGGGSLGSPYPG
                     ::::::::::::::::::: :::::.::::  :::.::::::::  .::.:.:::.::  :
SEQ ID NO:4  MOUSE   MGIVEPGCGDMLTGTEPMP-SDEGRGPGADQQHRFFYPEPGAQDPTDRRAGSSLGTPYSG
                          10         20         30          40         50

CONS    MGIVEPGCGDMLTGTEPMP SDEGR PGAD QHR FYPEPGAQD   RR G SLG PY G 70         80         90        100        110        120
SEQ ID NO:2  HUMAN   GALVPAPPSRFLGAYAYPPRPQAAGFPGAGESFPPPADAEGYQPGEGYAAPDPRAGLYPG
                     ::::::  :.::::..:::::  :.:::::  ::  :::::  ::::  :  .::  :::::::::::
SEQ ID NO:4  MOUSE   GALVPAAPGRFLGSFAYPPRAQVAGFPGPGEFFPPPAGAEGYPPVDGYPAPDPRAGLYPG
                          60         70         80         90        100        110

CONS    GALVPA P RFLG  AYPPR Q AGFPG GE FPPPA AEGY P  GY APDPRAGLYPG 130        140        150        160        170        180
SEQ ID NO:2  HUMAN   PREDYALPAGLEVSGKLRVALNNHLLWSKFNQHQTEMIITKQGRRMFPFLSFTVAGLEPT
                     :::::::::::::::::::::::.::::::::::::::::::::::::::::::::::::
SEQ ID NO:4  MOUSE   PREDYALPAGLEVSGKLRVALSNHLLWSKFNQHQTEMIITKQGRRMFPFLSFTVAGLEPT
                         120        130        140        150        160        170

CONS    PREDYALPAGLEVSGKLRVAL NHLLWSKFNQHQTEMIITKQGRRMFPFLSFTVAGLEPT 190        200        210        220        230        240
SEQ ID NO:2  HUMAN   SHYRMFVDVVLVDQHHWRYQSGKWVQCGKAEGSMPGNRLYVHPDSPNTGAHWMRQEVSFG
                     ::::::::::::::::::::::::::::::::::::::::::::::::::::::::::::
SEQ ID NO:4  MOUSE   SHYRMFVDVVLVDQHHWRYQSGKWVQCGKAEGSMPGNRLYVHPDSPNTGAHWMRQEVSFG
                         180        190        200        210        220        230

CONS    SHYRMFVDVVLVDQHHWRYQSGKWVQCGKAEGSMPGNRLYVHPDSPNTGAHWMRQEVSFG 250        260        270        280        290        300
SEQ ID NO:2  HUMAN   KLKLTNNKGASNNVTQMIVLQSLHKYQPRLHIVEVNDGEPEAACNASNTHIFTFQETQFI
                     :::::::::::::::::::::::::::::::::::::::::::.:::::.::::::::::
SEQ ID NO:4  MOUSE   KLKLTNNKGASNNVTQMIVLQSLHKYQPRLHIVEVNDGEPEAACSASNTHVFTFQETQFI
                         240        250        260        270        280        290

CONS    KLKLTNNKGASNNVTQMIVLQSLHKYQPRLHIVEVNDGEPEAAC ASNTH FTFQETQFI
```

Fig. 1A

```
                310       320       330       340       350       360
SEQ ID NO:2 HUMAN  AVTAYQNAEITQLKIDNNPFAKGFRENFESMYTSVDTSIPSPPGPNCQFLGGDHYSPLLP
                   ::::::::::::::::::::::::::::::::: ::::::.:::::::::.  .::::
SEQ ID NO:4 MOUSE  AVTAYQNAEITQLKIDNNPFAKGFRENFESMYASVDTSVPSPPGPNCQLLGGDPFSPLLS
                300       310       320       330       340       350

CONS   AVTAYQNAEITQLKIDNNPFAKGFRENFESMY SVDTS PSPPGPNCQ LGGD FSPLL 370       380       390       400       410       420
SEQ ID NO:2 HUMAN  NQYPVPSRFYPDLPGQAKDVVPQAYWLGAPRDHSYEAEFRAVSMKPAFLPSAPGPTMSYY
                   :::::::::::::::: ::.. : ::::.::.::::::::::::::..::::::::. ::
SEQ ID NO:4 MOUSE  NQYPVPSRFYPDLPGQPKDMISQPYWLGTPREHSYEAEFRAVSMKPTLLPSAPGPTVPYY
                360       370       380       390       400       410

CONS   NQYPVPSRFYPDLPGQ KD  Q YWLG PR HSYEAEFRAVSMKP  LPSAPGPT  YY 430       440       450       460       470       480
SEQ ID NO:2 HUMAN  RGQEVLAPGAGWPVAPQYPPKMGPASWFRPMRTLPMEPGPGGSEGRGPEDQGPPLVWTEI
                   :::.::::::::::::::::::::::.::.:::::::::::.: :.::  :   . : :.
SEQ ID NO:4 MOUSE  RGQDVLAPGAGWPVAPQYPPKMSPAGWFRPMRTLPMDPGLGSSEEQG----SSPSLWPEV
                420       430       440       450       460       470

CONS   RGQ VLAPGAGWPVAPQYPPKM PA WFRPMRTLPM PG G SE  G         P  W E 490       500       510       520       530
SEQ ID NO:2 HUMAN  APIRPESSDSGLGEGDSKRRRVSPYPSSGDSSSPAGAPSPFDKEAEGQFYNTFPN
                   . ..:: :::::::::.::::.:::::::::::::::::::::::.::::::::
SEQ ID NO:4 MOUSE  TSLQPEPSDSGLGEGDTKRRRISPYPSSGDSSSPAGAPSPFDKETEGQFYNYFPN
                480       490  ↑↑↑↑500       510       520       530

CONS       PE SDSGLGEGD KRRR SPYPSSGDSSSPAGAPSPFDKE EGQFYNYFPN
```

Fig. 1B

```
              10        20        30        40        50        60
SEQ ID NO:1 HUMAN ATGGGCATCGTGGAGCCGGGTTGCGGAGACATGCTGACGGGCACCGAGCCGATGCCGGGG
                  ::::::::::::::::::::: :::::::::::::::::: ::::::::::::::::::: :
SEQ ID NO:3 MOUSE ATGGGCATCGTGGAGCCGGGCTGCGGAGACATGCTGACCGGCACCGAGCCGATGCC---G
                  10        20        30        40        50

70        80        90       100       110       120
SEQ ID NO:1 HUMAN AGCGACGAGGGCCGGGCGCCTGGCGCCGACCCGCAGCACCGCTACTTCTACCCGGAGCCG
                  :: :::::::::::::::: ::: :: :: :::: ::::: :: :::::::: :::::::
SEQ ID NO:3 MOUSE AGTGACGAGGGCCGGGGGCCCGGAGCGGACCAACAGCATCGTTTCTTCTATCCCGAGCCG
                  60        70        80        90       100       110

130       140       150       160       170       180
SEQ ID NO:1 HUMAN GGCGCGCAGGACGCGGACGAGCGTCGCGGGGGCGGCAGCCTGGGGTCTCCCTACCCGGGG
                  ::::: :::::: :: ::: :: :::: :: :::::::::: : :::::: : :::
SEQ ID NO:3 MOUSE GGCGCACAGGACCCGACCGATCGCCGCGCAGGTAGCAGCCTGGGGACGCCCTACTCTGGG
                  120       130       140       150       160       170

190       200       210       220       230       240
SEQ ID NO:1 HUMAN GGCGCCTTGGTGCCCGCCCCGCCGAGCCGCTTCCTTGGAGCCTACGCCTACCCGCCGCGA
                  ::::::  ::::::: ::: :::::: : :::::::::::::: ::: ::::::::::: ::
SEQ ID NO:3 MOUSE GCGCCCTGGTGCCTGCCGCGCCGGGTCGCTTCCTTGGATCCTTCGCCTACCCGCCCCGG
                  180       190       200       210       220       230

250       260       270       280       290       300
SEQ ID NO:1 HUMAN CCCCAGGCGGCCGGCTTCCCCGGCGCGGGCGAGTCCTTCCCGCCGCCCGCGGACGCCGAG
                  :  ::::  :::  :::::  :::::  :  ::::::::  :::::::::::::::  ::  :::
SEQ ID NO:3 MOUSE GCTCAGGTGGCTGGCTTTCCCGGGCCTGGCGAGTTCTTCCCGCCGCCCGCGGGTGCGGAG
                  240       250       260       270       280       290

310       320       330       340       350       360
SEQ ID NO:1 HUMAN GGCTACCAGCCGGGCGAGGGCTACGCCGCCCCGGACCCGCGCGCCGGGCTCTACCCGGGG
                  :::::::  :::  :   ::  :::::::  :  :::::  :::::::::::::  :::::::::::  :::
SEQ ID NO:3 MOUSE GGCTACCCGCCCGTGGATGGCTACCCTGCCCCTGACCCGCGCGCGGGGCTCTACCCAGGG
                  300       310       320       330       340       350

370       380       390       400       410       420
SEQ ID NO:1 HUMAN CCGCGTGAGGACTACGCGCTACCCGCGGGACTGGAGGTGTCGGGGAAACTGAGGGTCGCG
                  :::::  :::::::::::::  :  :::::::::  ::::::::::::  :::::  :::::  :::::::::
SEQ ID NO:3 MOUSE CCGCGCGAGGACTACGCATTGCCCGCGGGGTTGGAGGTGTCTGGGAAGCTGAGAGTCGCG
                  360       370       380       390       400       410
```

Fig. 1C

```
                        430       440       450       460       470       480
SEQ ID NO:1  HUMAN  CTCAACAACCACCTGTTGTGGTCCAAGTTTAATCAGCACCAGACAGAGATGATCATCACC
                    ::::  ::::::::::::::::::::::::  ::  :::::::::::::::::::::::::::
SEQ ID NO:3  MOUSE  CTCAGCAACCACCTGTTGTGGTCCAAGTTCAACCAGCACCAGACAGAGATGATCATCACT
                      420       430       440       450       460       470

490       500       510       520       530       540
SEQ ID NO:1  HUMAN  AAGCAGGGACGGCGGATGTTCCCATTCCTGTCATTTACTGTGGCCGGGCTGGAGCCCACC
                    :::::  :::::::: ::::::::::::::::::  ::  ::::::::::::::::::::
SEQ ID NO:3  MOUSE  AAGCAAGGACGGCGAATGTTCCCATTCCTGTCCTTCACCGTGGCCGGGCTGGAGCCCACA
                      480       490       500       510       520       530

550       560       570       580       590       600
SEQ ID NO:1  HUMAN  AGCCACTACAGGATGTTTGTGGACGTGGTCTTGGTGGACCAGCACCACTGGCGGTACCAG
                    :::::  ::::::::::::::::::  ::::::::::::::::::::::::::::::::::
SEQ ID NO:3  MOUSE  AGCCATTACAGGATGTTTGTGGATGTGGTCTTGGTGGACCAGCACCACTGGCGGTACCAG
                      540       550       560       570       580       590

610       620       630       640       650       660
SEQ ID NO:1  HUMAN  AGCGGCAAGTGGGTGCAGTGTGGAAAGGCCGAGGGCAGCATGCCAGGAAACCGCCTGTAC
                    ::::::::::::::::::::::::::::::::  ::  :::::::::::: ::::::  ::
SEQ ID NO:3  MOUSE  AGCGGCAAGTGGGTGCAGTGTGGAAAGGCAGAAGGCAGCATGCCAGGGAACCGCTTATAT
                      600       610       620       630       640       650

670       680       690       700       710       720
SEQ ID NO:1  HUMAN  GTCCACCCGGACTCCCCCAACACAGGAGCGCACTGGATGCGCCAGGAAGTTTCATTTGGG
                    ::::::::  :::::::::::::::  :::::  :::::::::::::::::::::::::::
SEQ ID NO:3  MOUSE  GTCCACCCAGACTCCCCCAACACCGGAGCCCACTGGATGCGCCAGGAAGTTTCATTTGGG
                      660       670       680       690       700       710

730       740       750       760       770       780
SEQ ID NO:1  HUMAN  AAACTAAAGCTCACAAACAACAAGGGGGCGTCCAACAATGTGACCCAGATGATTGTGCTC
                    ::  ::::::::::::  ::::::::::::::::  ::::::::::::::::::::  ::
SEQ ID NO:3  MOUSE  AAGCTAAAGCTCACCAACAACAAGGGGGCTTCCAACAATGTGACCCAGATGATCGTCCTG
                      720       730       740       750       760       770

790       800       810       820       830       840
SEQ ID NO:1  HUMAN  CAGTCCCTCCATAAGTACCAGCCCCGGCTGCATATCGTTGAGGTGAACGACGGAGAGCCA
                    :::::  ::::: ::::::::::::::::::::::  ::::: :::::  ::  ::::::::
SEQ ID NO:3  MOUSE  CAGTCTCTCCACAAGTACCAGCCCCGGCTGCACATCGTGGAGGTGAATGATGGAGAGCCA
                      780       790       800       810       820       830
```

Fig. 1D

```
                         850       860       870       880       890       900
SEQ ID NO:1  HUMAN   GAGGCAGCCTGCAACGCTTCCAACACGCATATCTTTACTTTCCAAGAAACCCAGTTCATT
                     ::::: ::::::::  :::::  :::::  ::  ::::::::::::::::  ::::::::::::
SEQ ID NO:3  MOUSE   GAGGCTGCCTGCAGTGCTTCTAACACACACGTCTTTACTTTCCAAGAGACCCAGTTCATT
                        840       850       860       870       880       890

910       920       930       940       950       960
SEQ ID NO:1  HUMAN   GCCGTGACTGCCTACCAGAATGCCGAGATTACTCAGCTGAAAATTGATAATAACCCCTTT
                     ::  :::::::::::::::::::  ::::::  ::::::::::::::::  ::  ::::::::::
SEQ ID NO:3  MOUSE   GCAGTGACTGCCTACCAGAACGCAGAGATCACTCAGCTGAAAATCGACAACAACCCCTTT
                        900       910       920       930       940       950

970       980       990      1000      1010      1020
SEQ ID NO:1  HUMAN   GCCAAAGGATTCCGGGAGAACTTTGAGTCCATGTACACATCTGTTGACACCAGCATCCCC
                     :::::::::::::::::::::::::::::::::::::::::::  :::::::::::  ::  ::  :::::
SEQ ID NO:3  MOUSE   GCCAAAGGATTCCGGGAGAACTTTGAGTCCATGTACGCATCTGTTGATACGAGTGTCCCC
                        960       970       980       990      1000      1010

1030      1040      1050      1060      1070      1080
SEQ ID NO:1  HUMAN   TCCCCGCCTGGACCCAACTGTCAATTCCTTGGGGGAGATCACTACTCTCCTCTCCTACCC
                     ::  ::  ::::::::::::::::::::::  :  ::::::::::::  :  ::  :::  :::::  :::  ::
SEQ ID NO:3  MOUSE   TCGCCACCTGGACCCAACTGTCAACTGCTTGGGGGAGACCCCTTCTCACCTCTTCTATCC
                        1020      1030      1040      1050      1060      1070

1090      1100      1110      1120      1130      1140
SEQ ID NO:1  HUMAN   AACCAGTATCCTGTTCCCAGCCGCTTCTACCCCGACCTTCCTGGCCAGGCGAAGGATGTG
                     :::::::::::::::::::::::  ::::::::::::::::::::  ::::::::::  ::::::  ::
SEQ ID NO:3  MOUSE   AACCAGTATCCTGTTCCCAGCCGTTTCTACCCCGACCTTCCAGGCCAGCCCAAGGATATG
                        1080      1090      1100      1110      1120      1130

1150      1160      1170      1180      1190      1200
SEQ ID NO:1  HUMAN   GTTCCCCAGGCTTACTGGCTGGGGGCCCCCCGGGACCACAGCTATGAGGCTGAGTTTCGA
                     :   :  :::  :::::::::::::::::  :  ::  :::::  :::::  :::::  ::  :::::  :::
SEQ ID NO:3  MOUSE   ATCTCACAGCCTTACTGGCTGGGGACACCTCGGGAACACAGTTATGAAGCGGAGTTCCGA
                        1140      1150      1160      1170      1180      1190

1210      1220      1230      1240      1250      1260
SEQ ID NO:1  HUMAN   GCAGTCAGCATGAAGCCTGCATTCTTGCCCTCTGCCCCTGGGCCCACCATGTCCTACTAC
                     ::  ::  :::::::::::::::  ::  ::  :::::::::: :::::::::: ::  ::::::::
SEQ ID NO:3  MOUSE   GCTGTGAGCATGAAGCCCACACTCCTACCCTCTGCCCCGGGGCCCACTGTGCCCTACTAC
                        1200      1210      1220      1230      1240      1250
```

Fig. 1E

```
                    1270       1280       1290       1300       1310       1320
SEQ ID NO:1  HUMAN  CGAGGCCAGGAGGTCCTGGCACCTGGAGCTGGCTGGCCTGTGGCACCCCAGTACCCTCCC
                    :: :::::  ::  :::::::: ::::::::::: :::::  :::::  ::  :: :::::  :::
SEQ ID NO:3  MOUSE  CGGGGCCAAGACGTCCTGGCGCCTGGAGCTGGTTGGCCCGTGGCCCCCTCAATACCCGCCC
                    1260       1270       1280       1290       1300       1310

1330       1340       1350       1360       1370       1380
SEQ ID NO:1  HUMAN  AAGATGGGCCCGGCCAGCTGGTTCCGCCCTATGCGGACTCTGCCCATGGAACCCGGCCCT
                    ::::::: ::::  ::  ::::::::::::  ::  :::: ::::::::::::::: ::  ::::
SEQ ID NO:3  MOUSE  AAGATGAGCCCAGCTGGCTGGTTCCGGCCCATGCGAACTCTGCCCATGGACCCGGGCCTG
                    1320       1330       1340       1350       1360       1370

1390       1400       1410       1420       1430       1440
SEQ ID NO:1  HUMAN  GGAGGCTCAGAGGGACGGGGACCAGAGGACCAGGGTCCCCCCTTGGTGTGGACTGAGATT
                    :::  :::::::::  ::  :::  :                  ::::::  :  :::::  :::::  :
SEQ ID NO:3  MOUSE  GGATCCTCAGAGGAACAGGGCTCCT------------CCCCCTCGCTGTGGCCTGAGGTC
                    1380       1390       1400                   1410       1420

1450       1460       1470       1480       1490       1500
SEQ ID NO:1  HUMAN  GCCCCCATCCGGCCGGAATCCAGTGATTCAGGACTGGGCGAAGGAGACTCTAAGAGGAGG
                    ::  ::  :::  ::::::  ::::  ::  :::::::::  :::::::::::::  :::::::::::
SEQ ID NO:3  MOUSE  ACCTCCCTCCAGCCGGAGCCCAGCGACTCAGGACTAGGCGAAGGAGACACTAAGAGGAGG
                    1430       1440       1450       1460       1470       1480

1510       1520       1530       1540       1550       1560
SEQ ID NO:1  HUMAN  CGCGTGTCCCCCTATCCTTCCAGTGGTGACAGCTCCTCCCCTGCTGGGGCCCCTTCTCCT
                    :  ::::::::::::::::::: :::::::: ::::::::::::::::::::::::::::::::
SEQ ID NO:3  MOUSE  AGGATATCCCCCTATCCTTCCAGTGGCGACAGCTCCTCTCCCGCTGGGGCCCCTTCTCCT
                    1490       1500       1510       1520       1530       1540

1570       1580       1590       1600
SEQ ID NO:1  HUMAN  TTTGATAAGGAAGCTGAAGGACAGTTTTATAACTATTTTCCCAACTGA
                    :::::::::::::: :  :::::  ::::::::::::  :::::::::::::::::::
SEQ ID NO:3  MOUSE  TTTGATAAGGAAACCGAAGGCCAGTTTTATAATTATTTTCCCAACTGA
                    1550       1560       1570       1580       1590
```

Fig. 1F

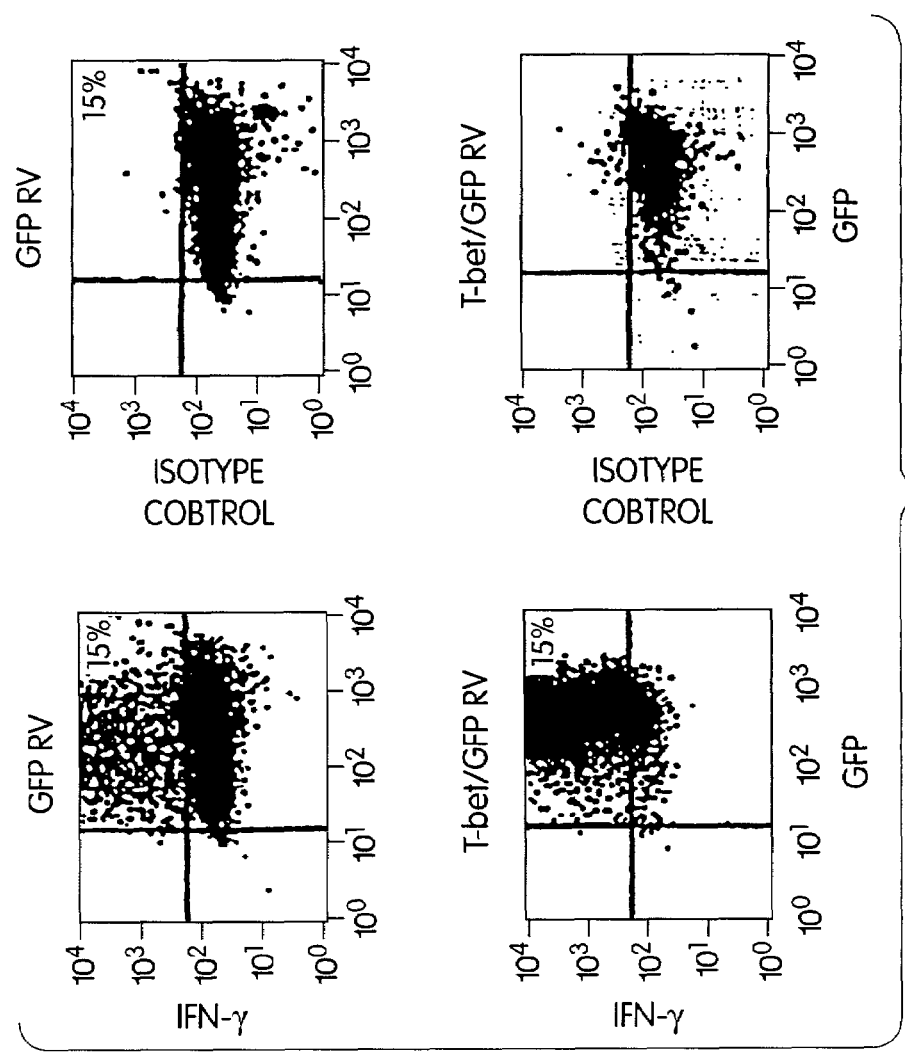

T-BET COMPOSITIONS AND METHODS OF USE THEREOF

RELATED APPLICATIONS

This application is continuation-in-part application of PCT/US00/15345, filed on Jun. 1, 2000, pending, published pursuant to PCT Article 21, in English, the entire contents of which are incorporated herein by this reference.

GOVERNMENT FUNDING

Work described herein was supported, at least in part, under grants AI/AG 37833, AI 39646, AI 36535, AR 6-2227, TGAI 07290 awarded by the National Institutes of Health. The U.S. government therefore may have certain rights in this invention.

BACKGROUND OF THE INVENTION

Cells of the immune system alter patterns of gene expression in response to extracellular and intracellular signals. A group of polypeptides, designated cytokines or lymphokines, which affect a range of biological activities in several cell types, are among the most important of these signals. While many cell types in the immune system secrete cytokines, the T helper (Th) lymphocyte is the major source of these polypeptides. More than a decade ago it was discovered that Th cells differentiate into two distinct subsets, Th1 and Th2, upon T cell receptor engagement, defined both by their distinct functional abilities and by unique cytokine profiles (Paul and Seder, 1994, Cell 76, 241-251; Mosmann and Coffman, 1989, Annu. Rev. Immunol. 7, 145-173; Mosmann et al., 1986, J. Immunol. 136, 2348-2357; Snapper and Paul, 1987, Science 236, 944-947). Th1 cells mediate delayed type hypersensitivity responses and macrophage activation while Th2 cells provide help to B cells and are critical in the allergic response (Mosmann and Coffman, 1989, Annu. Rev. Immunol. 7, 145-173; Paul and Seder, 1994, Cell 76, 241-251; Arthur and Mason, 1986, J. Exp. Med. 163, 774-786; Paliard et al., 1988, J. Immunol. 141, 849-855; Finkelman et al., 1988, J. Immunol. 141, 2335-2341). The evidence that Th1 cells directed cell-mediated immunity while Th2 cells contributed to humoral responses fit nicely with the observations that an organism tends to mount either a cell-mediated or humoral response, but not both, in response to pathogens. These functional differences between the Th subsets can be explained most easily by the activities of the cytokines themselves. IFN-γ is the "signature" cytokine of Th1 cells although Th1 cells also produce IL-2, TNF and LT. The corresponding "signature" cytokine for Th2 cells is IL-4. Th2 cells also secrete IL-5, IL-6, IL-9, IL-10 and IL-13.

Upon encountering antigen, the naive CD4+ T helper precursor (Thp) cell enacts a genetic program that ultimately sends it down a Th1 or Th2 lineage. While it is clear that polarization can be achieved by manipulating the antigen and costimulatory signals i.e. the "strength of signal" received by the Thp (Constant and Bottomly, 1997. Annu. Rev. Immunol. 15, 297-322), the most potent inducers of effector Th cells are undoubtedly the cytokines themselves. IL-4 promotes Th2 differentiation and simultaneously blocks Th1 development, an effect that is mediated via the Stat6 signaling pathway. Thus, mice that lack IL-4 or Stat6, fail to develop Th2 cells (Kopf et al., 1993, Nature 362, 245-248; Kuhn et al., 1991, Science 254, 707-710; Kaplan et al., 1996, Immunity 4, 313-319; Shimoda et al., 1996, Nature 380, 630-633; Takeda et al., 1996, Nature 380, 627-630). In contrast, IL-12, IL-18 and IFN-γ are the cytokines critical for the development of Th1 cells (Hsieh et al., 1993, Science 260, 547-549; Okamura et al., 1995, nature 378, 88-91; Gu et al., 1997, Science 275, 206-209; Meraz et al., 1996, Cell 84, 431-442; Magram et al., 1996, Immunity 4, 471-481). IFN-γ acting via the Stat1 pathway (Meraz et al., 1996, Cell 84, 431-442), and IL-12, acting via the Stat-4 signaling pathway (Jacobson et al., 1995, J. Exp. Med. 181, 1755-1762) together promote the differentiation of Th1 cells and block commitment to the Th2 lineage (Szabo et al., 1995, Immunity 2, 665-675; Szabo et al., 1997, J. Exp. Med. 185: 817-824). Mice deficient in IL-12 or Stat4 do not have Th1 cells (Magram et al., 1996, Immunity 4, 471-481; Takeda et al., 1996, Nature 380, 627-630; Shimoda et al., 1996, Nature 380, 630-633). Another important Th1-inducing cytokine is IL-18, whose receptor is related to the IL-1 receptor family (Cerretti et al., 1992, Science 256, 97-100). Mice lacking IL-18 have defective in vivo Th1 responses (Takeda et al., 1998, Immunity 8, 383-390) and both IL-12 and IL-18 regulate IFN-γ expression (Barbulescu et al., 1998, Eur. J. Immunol. 27, 1098-1107; Robinson et al., 1997, Immunity 7, 571-581; Ahn et al., 1997, J. Immunol. 159, 2125-2131). The cytokines themselves, then, form a positive and negative feedback system that drives Th polarization (Powrie and Coffman, 1993, Immunol. Today 14, 270-274; Scott, 1991, J. Immunol. 147, 3149; Maggi et al., 1992, J. Immunol. 148, 2142; Parronchi et al., 1992, J. Immunol. 149, 2977; Fargeas et al., 1992, Eur. J. Immunol. 149, 2977; Manetti et al., 1993, J. Exp. Med. 177, 1199; Trinchieri, 1993, Immunol. Today 14, 335-338; Macatonia et al., 1993, Immunol. 5, 1119; Seder et al., 1993, Proc. Natl. Acad. Sci. USA 90, 10188-10192; Wu et al., 1993, J. Immunol. 151, 1938; Hsieh et al., 1993, Science 260, 547-549) (reviewed in (Seder and Paul, 1994, In Annual Review of Immunology, Vol. 12, 635-673, Paul and Seder, 1994, Cell 76, 241-251; O'Garra, 1998, Immunity 8, 275-283).

Over the last few years, significant progress has been made in identifying the transcription factors that control the transition of a Thp to a Th2 cell as evidenced by the capacity of such factors to drive IL-4 production reviewed in (Glimcher and Singh, 1999 Cell 96, 13-23; Szabo et al., 1997, Current Opinions in Immunology 9, 776-781). The provision of three distinct proteins, the c-Maf proto-oncogene, the transcription factor Nuclear Factor of Activated T cells (NFAT), and a novel nuclear antigen, NFAT-Interacting Protein 45 kD (NIP45), have been shown to confer on a non-T cell the ability to produce endogenous IL-4 (Hodge et al., 1996, Science 274, 1903-1905; Ho et al., 1998, J. Exp. Med. 188:1859-1866). These factors and others such as GATA-3 (Zheng and Flavell, 1997, Cell 89, 587-596) and Stat6 clearly can drive the production of IL-4, and therefore the development of Th2 cells, both in vitro and in vivo.

In contrast, little is known about the molecular basis of Th1 differentiation. For example, the only known transcription factors whose absence results in a failure to generate Th1 cells are Stat4 (Thierfelder et al., 1996, Nature 382, 171-174; Kaplan et al., 1996, Nature 382, 174-177) and IRF-1 (Lohoff et al., 1997, Immunity :681-689; Taki et al., 1997, Immunity 6: 673-679), neither of which is Th1-specific. The Ets family member ERM which is induced by IL-12 in a Stat4-dependent manner has recently been reported to be Th1-specific but it does not affect the production of Th1 cytokines (Ouyang et al., 1999, Proc. Natl. Acad. Sci. 96:3888). The absence of Th1 cells in Stat4 deficient mice is secondary to the failure of IL-12 to drive the Th1 program while the lack of Th1 cells in IRF-1 deficient mice is likely due to its direct effect in controlling transcription of the IL-12 gene (Lohoff et al., 1997, Immunity 6: 681-689; Taki et al., 1997, Immunity 6:673-

679). However, some of the signaling pathways upstream of such putative Th1-specific regulatory factors are beginning to be elucidated. The p38 kinase is one such signaling molecule as demonstrated by the ability of constitutively activated MAP kinase kinase 6 (MKK6) to boost IFN-γ production. Conversely, overexpression of a dominant negative p38 MAP kinase or targeted disruption of Jnk2 or Jnk1 reduces Th1 responses (Rincon et al., 1998, EMBO J. 17, 2817-2829; Yang et al., 1998, Immunity 9, 575-585; Dong et al., 1998, Science 282, 2092-2095). The JNK signaling pathway might affect Th development by a direct effect on the transcription of the IFN-γ gene, but this has not been shown. For example, the ATF-2 and AP-1 transcription factors are both substrates of JNK kinases and these factors as well as NF☐B and Stat4 proteins are known to bind to sites in the IFN-γ promoter (Zhang et al., 1998, Immunol. 161 , 6105-6112; Ye et al., 1996, Mol. Cell. Biol. 16:4744; Barbulescu et al., 1997, Eur. J. Immunol. 27, 1098-1107; Sica et al., 1997, J. Biol. Chem. 272, 30412-30420). The production of IFN-γ is, however, normal in mice lacking ATF-2. Because cytokines are critical in the development of Th1 and Th2 cells and, thereby, in determining whether an immune response will be primarily cellular or humoral, compositions and methods for modulating the production of Th1 and/or Th2 cytokines would be of tremendous benefit in modulating the immune response.

SUMMARY OF THE INVENTION

This invention is based, at least in part, on the discovery of novel compositions which act to promote the Th1 phenotype in naïve T helper precursor cells (Thp), both by initiating Th1 cell genetic programs and by repressing the opposing programs in Th2 cells. In particular, this invention provides isolated nucleic acid molecules encoding T-bet and isolated T-bet protein. T-bet (T box expressed in T cells) is a new member of the T box family of transcription factors whose founding member is the brachyury gene. T-bet is constitutively expressed selectively in thymocytes and Th1 cells. T-bet is the first Th1 specific transcription factor that can transactivate the interferon-gamma gene, induce interferon-gamma production in retrovirally transduced primary T cells and redirect polarized Th2 cells into the Th1 pathway. The invention also provides methods of using these novel T-bet compositions.

One aspect of the invention pertains to an isolated nucleic acid molecule comprising a nucleotide sequence encoding T-bet. In a preferred embodiment, the nucleic acid molecule comprises the nucleotide sequence of SEQ ID NO: 1 or 3. In other embodiments, the nucleic acid molecule comprises at least 700 contiguous nucleotides of SEQ ID NO:1 or at least 500 contiguous nucleotides of SEQ ID NO:3. In a preferred embodiment, the nucleic acid molecule has at least 70% nucleotide identity, with at least 700 contiguous nucleotides of SEQ ID NO:1 or at least 70% identity with at least 500 contiguous nucleotides of SEQ ID NO:3.

The isolated nucleic acid molecules of the invention encoding T-bet can be incorporated into a vector, such as an expression vector, and this vector can be introduced into a host cell. The invention also provides a method for producing a T-bet protein by culturing a host cell of the invention (carrying a T-bet expression vector) in a suitable medium until a T-bet protein is produced. The method can further involve isolating the T-bet protein from the medium or the host cell.

Another aspect of the invention pertains to an isolated T-bet protein. Preferably, the T-bet protein comprises the amino acid sequence of SEQ ID NO: 2 or 4. In other embodiments, the protein has at least 60% amino acid identity, at least 70% amino acid identity, more preferably 80% amino identity, at, and even more preferably 90% amino acid identity with the amino acid sequence shown in SEQ ID NO:1 or 3.

Fusion proteins, comprising a T-bet protein operatively linked to a polypeptide other than T-bet, are also encompassed by the invention, as well as antibodies that specifically bind a T-bet protein. The antibodies can be, for example, polyclonal antibodies or monoclonal antibodies. In one embodiment, the antibodies are coupled to a detectable substance.

Another aspect of the invention pertains to a nonhuman transgenic animal that contains cells carrying a transgene encoding a T-bet protein.

Yet another aspect of the invention pertains to a method for detecting the presence of T-bet in a biological sample. The method involves contacting the biological sample with an agent capable of detecting an indicator of T-bet activity such that the presence of T-bet is detected in the biological sample. The invention also provides a method for modulating T-bet activity in a cell comprising, involving contacting the cell with an agent that modulates T-bet activity such that T-bet activity in the cell is modulated.

Still another aspect of the invention pertains to methods for identifying a compound that modulates the activity of a T-bet protein. These methods generally involve:

providing an indicator composition that comprises a T-bet protein;

contacting the indicator composition with a test compound; and determining the effect of the test compound on the activity of the T-bet protein in the indicator composition to thereby identify a compound that modulates the activity of a T-bet protein. In a preferred embodiment, the indicator composition comprises a T-bet protein and a DNA molecule to which the T-bet protein binds and the effect of the test compound on the activity of the T-bet protein is determined by evaluating the binding of the T-bet protein to the DNA molecule in the presence and absence of the test compound. In another preferred embodiment, the indicator composition is a cell comprising a T-bet protein and a reporter gene responsive to the T-bet protein and the effect of the test compound on the activity of the T-bet protein is determined by evaluating the expression of the reporter gene in the presence and absence of the test compound. In yet another embodiment, the method further involves the step of determining the effect of the test compound on an immune response to thereby identify a compound that modulates an immune response.

In yet another preferred embodiment, wherein the activity of T-bet is enhanced. In another preferred embodiment, the activity of T-bet is inhibited. In a particularly preferred embodiment, the activity of T-bet is IFN-γ production. In another embodiment, the activity of T-bet is transcription of IgG2a. In another embodiment, the step of contacting occurs in vivo. In yet another embodiment, the step of contacting occurs in vitro.

In another embodiment, the test compound is selected from the group comprised of: a T-bet nucleic acid molecule, a T-bet peptide, a small molecule T-bet agonist and a small molecule T-bet antagonist. In yet another embodiment, the test compound is selected from a group comprised of: an intracellular antibody, a nucleic acid molecule that is antisense to a T-bet molecule, a dominant negative T-bet molecule, a small molecule T-bet agonist and a small molecule T-bet antagonist. In another embodiment, the cell is selected from the group consisting of: a T cell, a B cell, and a macrophage. In a particularly preferred embodiment, the cell is a Th1 cell.

Another aspect of the invention pertains to a method of diagnosing a subject for a disorder associated with aberrant immune cell activation comprising:

detecting expression of T-bet in immune cells of a subject suspected of having said disorder;

comparing expression of T-bet in immune cells of said subject to a control that is not associated with aberrant immune cell activation; and diagnosing the subject for a disorder based on a change in expression of T-bet in immune cells of the subject as compared to the control.

In one embodiment, the disorder is an autoimmune disease. In another embodiment, the disorder is lupus. In a particularly preferred embodiment, the disorder is Inflammatory Bowel Disease. In another particularly preferred embodiment, the disorder is Crohn's disease. In another particularly preferred embodiment, the disorder is ulcerative colitis. In yet another particularly preferred embodiment, the disorder is asthma.

BRIEF DESCRIPTION OF THE DRAWINGS

FIGS. 1A-1B show a nucleotide sequence alignment of murine and human T-bet. The alignment was prepared using the ALIGN program. FIGS. 1C-1F show an amino acid sequence alignment of murine and human T-bet prepared using the Lipman Pearson protein alignment program. The T-box sequence is shown in bold. Tyrosine phosphorylation sites are underlined. The nuclear localization site is marked with arrows.

DETAILED DESCRIPTION OF THE INVENTION

Figure 2A:
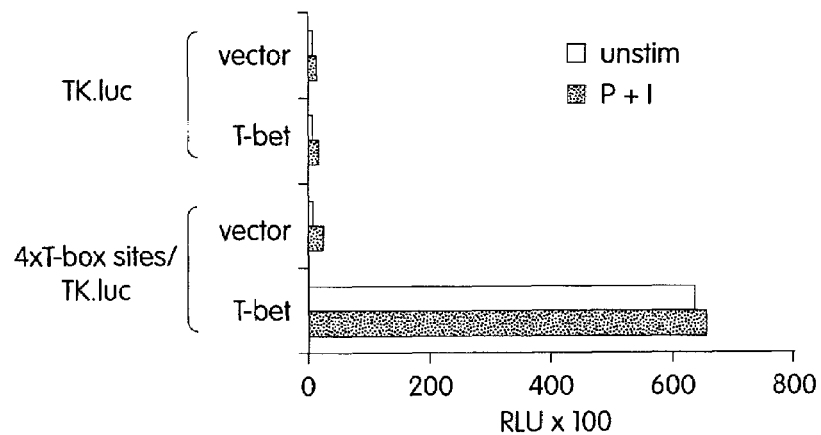
FIGS. 2A and B show that T-bet binds to and transactivates consensus T-box sites with functionally important domains that map to both 5' and 3' regions.

This invention pertains to T-bet compositions, such as isolated nucleic acid molecules encoding T-bet and isolated T-bet proteins, as well as methods of use therefore.

So that the invention may be more readily understood, certain terms are first defined.

As used herein, the term "T-bet molecules" includes T-bet nucleic acid molecules that share structural features with the nucleic acid molecules shown in SEQ ID Nos: 1 and 3 and T-bet proteins that share the distinguishing structural and functional features of the T-bet proteins shown in SEQ ID Nos 2 and 4. The T-bet proteins are members of the T-box family of proteins and share some amino acid sequence homology to Brachyury, Tbx1-6, T-brain-1 (Tbr-1). T-box proteins comprise a T box domain which binds to DNA at a T box binding site. Further structural and functional features of T-bet proteins are provided below.

As used herein, the term "nucleic acid molecule" is intended to include DNA molecules (e.g., cDNA or genomic DNA) and RNA molecules (e.g., mRNA). The nucleic acid molecule may be single-stranded or double-stranded, but preferably is double-stranded DNA.

An used herein, an "isolated nucleic acid molecule" refers to a nucleic acid molecule that is free of gene sequences which naturally flank the nucleic acid in the genomic DNA of the organism from which the nucleic acid is derived (i.e., genetic sequences that are located adjacent to the gene for the isolated nucleic acid molecule in the genomic DNA of the organism from which the nucleic acid is derived). For example, in various embodiments, an isolated T-bet nucleic acid molecule typically contains less than about 10 kb of nucleotide sequences which naturally flank the nucleic acid molecule in genomic DNA of the cell from which the nucleic acid is derived, and more preferably contains less than about 5, kb, 4 kb, 3 kb, 2 kb, 1 kb, 0.5 kb or 0.1 kb of naturally flanking nucleotide sequences. An "isolated" T-bet nucleic acid molecule may, however, be linked to other nucleotide sequences that do not normally flank the T-bet sequences in genomic DNA (e.g., the T-bet nucleotide sequences may be linked to vector sequences). In certain preferred embodiments, an "isolated" nucleic acid molecule, such as a cDNA molecule, also may be free of other cellular material. However, it is not necessary for the T-bet nucleic acid molecule to be free of other cellular material to be considered "isolated" (e.g., a T-bet DNA molecule separated from other mammalian DNA and inserted into a bacterial cell would still be considered to be "isolated").

As used herein, the term "hybridizes under high stringency conditions" is intended to describe conditions for hybridization and washing under which nucleotide sequences having substantial homology (e.g., typically greater than 70% homology) to each other remain stably hybridized to each other. A preferred, non-limiting example of high stringency conditions are hybridization in a hybridization buffer that contains 6×sodium chloride/sodium citrate (SSC) at a temperature of about 45° C. for several hours to overnight, followed by one or more washes in a washing buffer containing 0.2×SSC, 0.1% SDS at a temperature of about 50-65° C.

The term "percent (%) identity" as used in the context of nucleotide and amino acid sequences (e.g., when one amino acid sequence is said to be X % identical to another amino acid sequence) refers to the percentage of identical residues shared between the two sequences, when optimally aligned. To determine the percent identity of two nucleotide or amino acid sequences, the sequences are aligned for optimal comparison purposes (e.g., gaps may be introduced in one sequence for optimal alignment with the other sequence). The residues at corresponding positions are then compared and when a position in one sequence is occupied by the same residue as the corresponding position in the other sequence, then the molecules are identical at that position. The percent identity between two sequences, therefore, is a function of the number of identical positions shared by two sequences (i.e., % identity=# of identical positions/total # of positions×100).

Computer algorithms known in the art can be used to optimally align and compare two nucleotide or amino acid sequences to define the percent identity between the two sequences. A preferred, non-limiting example of a mathematical algorithm utilized for the comparison of two sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the NBLAST and XBLAST programs of Altschul, et al. (1990) J. Mol. Biol. 215:403-10. To obtain gapped alignments for comparison purposes, Gapped BLAST can be utilized as described in Altschul et al., (1997) Nucleic Acids Research 25 (17):3389-3402. When utilizing BLAST and Gapped BLAST programs, the default parameters of the respective programs (e.g., XBLAST and NBLAST) can be used. For example, the nucleotide sequences of the invention were blasted using the default Blastn matrix 1-3 with gap penalties set at: existence 5 and extension 2. The amino acid sequences of the invention were blasted using the default settings: the Blosum62 matrix with gap penalties set at existence 11 and extension 1.

Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence aligmnnent software package. When utilizing the ALIGN program for comparing amino acid sequences, a PAM120 weight residue table, a gap length penalty of 12, and a gap penalty of 4 can be used. If multiple programs are used to compare sequences, the program that provides optimal alignment (i.e., the highest percent identity between the two sequences) is used for comparison purposes.

As used herein, a "naturally-occurring" nucleic acid molecule refers to an RNA or DNA molecule having a nucleotide sequence that occurs in nature (e.g., encodes a natural protein).

As used herein, an "antisense" nucleic acid comprises a nucleotide sequence which is complementary to a "sense" nucleic acid encoding a protein, e.g., complementary to the coding strand of a double-stranded cDNA molecule, complementary to an mRNA sequence or complementary to the coding strand of a gene. Accordingly, an antisense nucleic acid can hydrogen bond to a sense nucleic acid.

As used herein, the term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions).

As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the formn of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

As used herein, the term "host cell" is intended to refer to a cell into which a nucleic acid of the invention, such as a recombinant expression vector of the invention, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

As used herein, a "transgenic animal" refers to a non-human animal, preferably a mammal, more preferably a mouse, in which one or more of the cells of the animal includes a "transgene". The term "transgene" refers to exogenous DNA which is integrated into the genome of a cell from which a transgenic animal develops and which remains in the genome of the mature animal, for example directing the expression of an encoded gene product in one or more cell types or tissues of the transgenic animal.

As used herein, a "homologous recombinant animal" refers to a type of transgenic non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

As used herein, an "isolated protein" refers to a protein that is substantially free of other proteins, cellular material and culture medium when isolated from cells or produced by recombinant DNA techniques, or chemical precursors or other chemicals when chemically synthesized.

As used herein, the term "antibody" is intended to include immunoglobulin molecules and immunologically active portions of immunoglobulin molecules, i.e., molecules that contain an antigen binding site which specifically binds (immunoreacts with) an antigen, such as Fab and F(ab')$_2$ fragments. The terms "monoclonal antibodies" and "monoclonal antibody composition", as used herein, refer to a population of antibody molecules that contain only one species of an antigen binding site capable of immunoreacting with a particular epitope of an antigen, whereas the term "polyclonal antibodies" and "polyclonal antibody composition" refer to a population of antibody molecules that contain multiple species of antigen binding sites capable of interacting with a particular antigen. A monoclonal antibody compositions thus typically display a single binding affinity for a particular antigen with which it immunoreacts.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid molecule and the amino acid sequence encoded by that nucleic acid molecule, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA molecule coding for a T-bet protein of the invention (or any portion thereof) can be use to derive the T-bet amino acid sequence, using the genetic code to translate the DNA or RNA molecule into an amino acid sequence. Likewise, for any T-bet-amnino acid sequence, corresponding nucleotide sequences that can encode the T-bet protein can be deduced from the genetic code (which, because of its redundancy, will produce multiple nucleic acid sequences for any given amino acid sequence). Thus, description and/or disclosure herein of a T-bet nucleotide sequence should be considered to also include description and/or disclosure of the amino acid sequence encoded by the nucleotide sequence. Similarly, description and/or disclosure of a T-bet amino acid sequence herein should be considered to also include description and/or disclosure of all possible nucleotide sequences that can encode the amino acid sequence.

Brachyury or T is the founding member of a family of transcription factors that share a 200 amino acid DNA-binding domain called the T-box (reviewed in (Smith, 1997; Papaioannou, 1997; Meisler, 1997)). The Brachyury (Greek for 'short tail') mutation was first described in 1927 in heterozygous mutant animals who had a short, slightly kinked tail (Herrmann et al., 1990). The amino-terminal half (amino acids 1-229) of the Brachyury T-box protein contains a conserved domain known as the T box which has been shown to exhibit sequence-specific DNA-binding activity (Kispert, A. & Herrmann, B. G. 1993. *EMBO J.* 12:3211; Papapetrou, C., et al. 1997. *FEBS Lett.* 409:201; Kispert, A., et al. 1995. *EMBO J.* 14:4763). The C-terminal half contains two pairs of transactivation and repression domains. The similarity of sequence between the T box region in orthologous species can be as high as 99% and is around 40-70% between non-orthologous genes. The T-box domain has recently been co-crystallized with DNA and demonstrates a novel sequence-specific DNA recognition architecture in which the protein contacts DNA in both the major and minor grooves (Müller, C. W. & Herrmann, B. G. 1997. *Nature* 389, 884).

A yeast one hybrid approach was used to identify Th-1 specific transcription factors. Yeast cells were made to express an IL-2 promoter-reporter gene construct and were transformned with a cDNA library made from an anti-CD3 activated Th1 cell clone. Inspection of the IL-2 promoter reveals an excellent T-box binding site at −240 to −220 just 5' of the NFkB site. As described in the appended examples, T-bet was isolated in a yeast one hybrid screening assay based on its ability to bind to the IL-2 promoter.

The nucleotide sequence encoding murine T-bet is shown in SEQ ID NO:3. Murine T-bet is a 530 amino acid protein with a 190 amino acid T-box domain located at residues 136-326. The amino acid sequence of murine T-bet is shown in SEQ ID NO:4. After the murine T-bet sequence was cloned as described herein, it was possible to compile the sequence of the human ortholog of T-bet from nucleic acid fragments which were not previously known to encode any known protein. The nucleotide sequence of human T-bet is shown in SEQ ID NO:1. Human T-bet is a 535 amino acid protein with a 190 amino acid T-box domain located at residues 138-327. The human T-bet gene maps to chromosome 17. The nucleotide and amino acid sequences of two members (human and mouse) of the T-bet family of proteins are shown in FIG. 1 and SEQ ID Nos: 1-4.

The T-bet proteins of the invention have homology to T-box proteins. There are now eight T-box genes in the mouse not including Brachyury. These include Tbx1-6, T-brain-1 (Tbr-1) and now, T-bet, each with a distinct and usually complex expression pattern. T-brain-1 expression, for example is largely restricted to distinct domains within the cerebral cortex (Bulfone, A., et al. 1995. *Neuron* 15, 63. T-bet is most similar in sequence to Tbr-1. Outside of the T-box, the T-bet proteins of the invention bear no similarity to other T-box proteins.

T-bet is T-box protein expressed only in T cells and is most similar in sequence to Tbr-1. Other species also express Brachyury-like genes. Such vertebrate species include Xenopus, zebrafish, chick and humans (Rao, 1994; Horb and Thomsen, 1997; Conlon et al., 1996; Ryan et al., 1996; Schulte-Merker et al., 1994; Edwards et al., 1996; Morrison et al., 1996; Law et al., 1995; Cambell et al., 1998) as well as more distant species such as amphioxus, ascidians, echinoderms, *Caenorhabditis elegans, Drosophila* and other insects (Holland et al., 1995). These genes are conserved both in sequence and in expression pattern.

T-bet is unique in that it is the only T-box protein to be tyrosine phosphorylated. There are two consensus tyrosine phosphorylation sites at aa 328-336 and 526-534 of human T-bet and 327-335 and 521-529 of murine T-bet. A nuclear localization sequence is also present at amino acids 498-501 of human T-bet and 493-496 of murine T-bet. Mapping experiments locate two transactivation domains, one 5' and one 3' of the T-box domain. The data shown herein demonstrate that T-bet binds to a consensus T-box site (defined by target site selection in vitro as 5'-GGGAATTTCACAC-CTAGGTGTGAAATTCCC-3') (SEQ ID NO:5) and to a T-box site in the IL-2 promoter. T-bet is expressed only in the thymus and in the peripheral lymphoid system. In the periphery, T-bet is expressed only in Th1 cells where it is induced both in response to TcR stimulation and to IL-12. In the thymus levels of T-bet are highest in DN and Rag2-/- thymocytes.

These data demonstrate that the selective expression of T-bet, a novel T-box family member, accounts for tissue-specific IFN-γ expression. T-bet is expressed only in Th1 and not in Th2 cells and is induced in the former upon transmission of signals through the T cell receptor. The expression of T-bet correlates with IFN-γ expression in Th1 cells, NK cells and B cells, and T-bet is a potent transactivator of the IFN-γ gene. Most convincing, retroviral mediated transduction of Thp, Th1 and polarized Th2 and Tc2 cells with T-bet results in an impressive induction of IFN-γ expression. This is accompanied by repression of both IL-2 and IL-4 production. Thus, the function of T-bet extends beyond the simple control of IFN-γ gene transcription. T-bet converts both polarized effector Th2 cells and polarized Tc2 cells into the opposing Th1 and Tc1 subsets, respectively. Taken together, these data demonstrate that T-bet is responsible for the genetic program that initiates Th1 lineage development from naïve Thp cells and acts both by initiating Th1 genetic programs and by repressing the opposing programs in Th2 cells.

Various aspects of the invention are described in further detail in the following subsections:

I. Isolated Nucleic Acid Molecules

One aspect of the invention pertains to isolated nucleic acid molecules that encode T-bet. In a preferred embodiment, the nucleic acid molecule of the invention comprises the nucleotide sequence shown in SEQ ID NO:1 or SEQ ID NO:3. In another embodiment, a nucleic acid molecule of the invention comprises at least about 700 contiguous nucleotides of SEQ ID NO:1 or at least about 500 contiguous nucleotides of SEQ ID NO:3. In a preferred embodiment, a nucleic acid molecule of the invention comprises at least about 800, at least about 1000, at east about 1200, at least about 1400 or at least about 1600 contiguous nucleotides of SEQ ID NO: 1. In another preferred embodiment, a nucleic acid molecule of the invention comprises at least about 600, at least about 800, at least about 1000, at least about 1200, or at least about 1400 contiguous nucleotides of SEQ ID NO:3.

In other embodiments, the nucleic acid molecule has at least 70% identity, more preferably 80% identity, and even more preferably 90% identity with a nucleic acid molecule comprising: at least about 700, at least about 800, at least about 1000, at east about 1200, at least about 1400 or at least about 1600 contiguous nucleotides of SEQ ID NO:1. In other embodiments, the nucleic acid molecule has at least 70% identity, more preferably 80% identity, and even more preferably 90% nucleotide identity with a nucleic acid molecule comprising: at least about 600, at least about 800, at least about 1000, at least about 1200, or at least about 1400 contiguous nucleotides of SEQ ID NO:3.

Nucleic acid molecules that differ from SEQ ID NO: 1 or 3 due to degeneracy of the genetic code, and thus encode the same T-bet protein as that encoded by SEQ ID NO: 1 and 3, are encompassed by the invention. Accordingly, in another embodiment, an isolated nucleic acid molecule of the invention has a nucleotide sequence encoding a protein having an amino acid sequence shown in SEQ ID NO: 2 or SEQ ID NO:4.

In addition, nucleic acid molecules encoding T-bet proteins can be isolated from other sources using standard molecular biology techniques and the sequence information provided herein. For example, a T-bet DNA can be isolated from a human genomic DNA library using all or portion of SEQ ID NO:1 or 3 as a hybridization probe and standard hybridization techniques (e.g., as described in Sambrook, J., et al. *Molecular Cloning: A Laboratory Manual. 2nd, ed., Cold Spring Harbor Laboratory*, Cold Spring Harbor, N.Y., 1989). Moreover, a nucleic acid molecule encompassing all or a portion of a T-bet gene can be isolated by the polymerase chain reaction using oligonucleotide primers designed based upon the sequence of SEQ ID NO: 1 or 3. For example, mRNA can be isolated from cells (e.g., by the guanidinium-thiocyanate extraction procedure of Chirgwin et al. (1979) *Biochemistry* 18: 5294-5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed based upon the nucleotide sequence shown in SEQ ID NO: 1 or 3. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to a T-bet nucleotide sequence can be prepared by standard synthetic techniques, e.g., using an automated DNA synthesizer.

In addition to the T-bet nucleotide sequence shown in SEQ ID NO: 1 and 3, it will be appreciated by those skilled in the art that DNA sequence polymorphisms that lead to minor changes in the nucleotide or amino acid sequences of T-bet may exist within a population. Such genetic polymorphism in the T-bet gene may exist among individuals within a population due to natural allelic variation. Such natural allelic variations can typically result in 1-2% variance in the nucleotide sequence of the a gene. Any and all such nucleotide variations and resulting amino acid polymorphisms in T-bet that are the result of natural allelic variation and that do not alter the functional activity of T-bet are intended to be within the scope of the invention.

Nucleic acid molecules corresponding to natural allelic variants of the T-bet DNAs of the invention can be isolated based on their homology to the T-bet nucleic acid molecules disclosed herein using the human DNA, or a portion thereof, as a hybridization probe according to standard hybridization techniques under high stringency hybridization conditions. Accordingly, in another embodiment, an isolated nucleic acid molecule of the invention hybridizes under high stringency conditions to a second nucleic acid molecule comprising the nucleotide sequence of SEQ ID NO: 1 or 3. Preferably, an isolated nucleic acid molecule of the invention that hybridizes under high stringency conditions to the sequence of SEQ ID NO: of SEQ ID NO:1 or 3. In one embodiment, such a nucleic acid molecule is at least about 700, 800, 900, 1000, 1200, 1300, 1400, 1500, or 1600 nucleotides in length. In another embodiment, such a nucleic acid molecule and comprises at least about 700, 800, 900, 1000, 1200, 1300, 1400, 1500, or 1600 contiguous nucleotides of SEQ ID NO: 1 or at least about 500, 600, 700, 800, 900, 1000, 1100, 1200, 1300, 1400, or 1500 contiguous nucleotides of SEQ ID NO: 3. Preferably, an isolated nucleic acid molecule corresponds to a naturally-occurring allelic variant of a T-bet nucleic acid molecule.

In addition to naturally-occurring allelic variants of the T-bet sequence that may exist in the population, the skilled artisan will further appreciate that minor changes may be introduced by mutation into the nucleotide sequence of SEQ ID NO: 1 or 3, thereby leading to changes in the amino acid sequence of the encoded protein, without altering the functional activity of the T-bet protein. For example, nucleotide substitutions leading to amino acid substitutions at "nonessential" amino acid residues may be made in the sequence of SEQ ID NO: 1 or 3. A "non-essential" amino acid residue is a residue that can be altered from the wild-type sequence of T-bet (e.g., the sequence of SEQ ID NO: 1 or 3) without altering the functional activity of T-bet, such as its ability to interact with DNA or its ability to enhance transcription from an IFN-gamma promoter, whereas an "essential" amino acid residue is required for functional activity.

Accordingly, another aspect of the invention pertains to nucleic acid molecules encoding T-bet proteins that contain changes in amino acid residues that are not essential for T-bet activity. Such T-bet proteins differ in amino acid sequence from SEQ ID NO: 2 or 4 yet retain T-bet activity. An isolated nucleic acid molecule encoding a non-natural variant of a T-bet protein can be created by introducing one or more nucleotide substitutions, additions or deletions into the nucleotide sequence of SEQ ID NO: 1 or 3 such that one or more amino acid substitutions, additions or deletions are introduced into the encoded protein. Mutations can be introduced into SEQ ID NO: 1 or 3 by standard techniques, such as site-directed mutagenesis and PCR-mediated mutagenesis. Preferably, conservative amino acid substitutions are made at one or more non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in T-bet is preferably replaced with another amino acid residue from the same side chain family.

Alternatively, in another embodiment, mutations can be introduced randomly along all or part of the T-bet coding sequence, such as by saturation mutagenesis, and the resultant mutants can be screened for their ability to bind to DNA and/or activate transcription, to identify mutants that retain functional activity. Following mutagenesis, the encoded T-bet mutant protein can be expressed recombinantly in a host cell and the functional activity of the mutant protein can be determined using assays available in the art for assessing T-bet activity (e.g., by measuring the ability of the protein to bind to a T-box binding element present in DNA or by measuring the ability of the protein to modulate a Th1 or Th2 phenotype in a T cell.

Another aspect of the invention pertains to isolated nucleic acid molecules that are antisense to the coding strand of a T-bet mRNA or gene. An antisense nucleic acid of the invention can be complementary to an entire T-bet coding strand, or to only a portion thereof. In one embodiment, an antisense nucleic acid molecule is antisense to a coding region of the coding strand of a nucleotide sequence encoding T-bet that is unique to the T-bet family of proteins or which is unique to a T-bet sequence from a particular species. In another embodiment, the antisense nucleic acid molecule is antisense to a noncoding region of the coding strand of a nucleotide sequence encoding T-bet that is unique to T-bet family of proteins or which is unique to a T-bet sequence from a particular species. In preferred embodiments, an antisense molecule of the invention comprises at least about 700 contiguous nucleotides of the noneoding strand of SEQ ID NO: 1, more preferably at least 800, 1000, 1200, 1400, or 1600 contiguous nucleotides of the noncoding strand of SEQ ID NO: 1 or at least about 500 contiguous nucleotides of the noncoding strand of SEQ ID NO: 3, more preferably at least 600, 800, 1000, 1200, or 1400 contiguous nucleotides of the noncoding strand of SEQ ID NO: 3.

Given the coding strand sequences encoding T-bet disclosed herein (e.g., SEQ ID NOs: 1 and 3, antisense nucleic acids of the invention can be designed according to the rules of Watson and Crick base pairing. The antisense nucleic acid molecule may be complementary to the entire coding region of T-bet mRNA, or alternatively can be an oligonucleotide which is antisense to only a portion of the coding or noncoding region of T-bet mRNA. For example, the antisense oligonucleotide may be complementary to the region surrounding the translation start site of T-bet mRNA. An antisense oligonucleotide can be, for example, about 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

In another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. A ribozyme having specificity for a T-bet-encoding nucleic acid can be designed based upon the nucleotide sequence of a T-bet gene disclosed herein. For example, a derivative of a Tetrahymena L-19 IVS RNA can be constructed in which the base sequence of the active site is complementary to the base sequence to be cleaved in a T-bet-encoding mRNA. See for example Cech et al. U.S. Pat. No. 4,987,071; and Cech et al. U.S. Pat. No. 5,116,742. Alternatively, T-bet mRNA can be used to select a catalytic RNA having a specific ribonuclease activity from a pool of RNA molecules. See for example Bartel, D. and Szostak, J. W. (1993) *Science* 261: 1411-1418.

Yet another aspect of the invention pertains to isolated nucleic acid molecules encoding T-bet fusion proteins. Such nucleic acid molecules, comprising at least a first nucleotide sequence encoding a T-bet protein, polypeptide or peptide operatively linked to a second nucleotide sequence encoding a non-T-bet protein, polypeptide or peptide, can be prepared by standard recombinant DNA techniques. T-bet fusion proteins are described in further detail below in subsection III.

II. Recombinant Expression Vectors and Host Cells

Another aspect of the invention pertains to vectors, preferably recombinant expression vectors, containing a nucleic acid encoding T-bet (or a portion thereof). The expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector may depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., T-bet proteins, mutant forms of T-bet proteins, T-bet fusion proteins and the like).

The recombinant expression vectors of the invention can be designed for expression of T-bet protein in prokaryotic or eukaryotic cells. For example, T-bet can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector may be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors can serve one or more purposes: 1) to increase expression of recombinant protein; 2) to increase the solubility of the recombinant protein; 3) to aid in the purification of the recombinant protein by acting as a ligand in affinity purification; 4) to provide an epitope tag to aid in detection and/or purification of the protein; and/or 5) to provide a marker to aid in detection of the protein (e.g., a color marker using □-galactosidase fusions). Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc.; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Recombinant proteins also can be expressed in eukaryotic cells as fusion proteins for the same purposes discussed above.

Examples of suitable inducible non-fusion *E. coli* expression vectors include pTrc (Amann et al., (1988) *Gene* 69:301-315) and pET 11d (Studier et al., *Gene Expression Technology: Methods in Enzymology* 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21 (DE3) or HMS174(DE3) from a resident λ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods inEnzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al., (1992) *Nuc. Acids Res.* 20:2111-2118). Such alteration of nucleic acid sequences of the invention can be carried out by standard DNA synthesis techniques.

In another embodiment, the T-bet expression vector is a yeast expression vector. Examples of vectors for expression in yeast *S. cerivisae* include pYepSec1 (Baldari. et al., (1987) *EMBO J.* 6:229-234), pMFa (Kurjan and Herskowitz, (1982) *Cell* 30:933-943), pJRY88 (Schultz et al., (1987) *Gene* 54:113-123), and pYES2 (Invitrogen Corporation, San Diego, Calif.).

Alternatively, T-bet can be expressed in insect cells using baculovirus expression vectors. Baculovirus vectors available for expression of proteins in cultured insect cells (e.g., Sf 9 cells) include the pAc series (Smith et al., (1983) *Mol. Cell Biol.* 3:2156-2165) and the pVL series (Lucklow, V. A., and Summers, M. D., (1989) *Virology* 170:31-39).

In yet another embodiment, a nucleic acid of the invention is expressed in mammalian cells using a mammalian expression vector. Examples of mammalian expression vectors include pMex-NeoI, pCDM8 (Seed, B., (1987) *Nature* 329: 840) and pMT2PC (Kaufman et al. (1987), *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), the albumin promoter (liver-specific; Pinkert et al. (1987) *Genes Dev.* 1:268-277), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine box promoters (Kessel and Gruss (1990) *Science* 249:374-379)

and the ☐-fetoprotein promoter (Campes and Tilghman (1989) *Genes Dev.* 3:537-546).

Moreover, inducible regulatory systems for use in mammalian cells are known in the art, for example systems in which gene expression is regulated by heavy metal ions (see e.g., Mayo et al. (1982) *Cell* 29:99-108; Brinster et al. (1982) *Nature* 296:39-42; Searle et al. (1985) *Mol. Cell. Biol.* 5:1480-1489), heat shock (see e.g., Nouer et al. (1991) in *Heat Shock Response*, e.d. Nouer, L., CRC, Boca Raton, Fla., pp 167-220), hormones (see e.g., Lee et al. (1981) *Nature* 294:228-232; Hynes et al. (1981) *Proc. Natl. Acad. Sci. USA* 78:2038-2042; Klock et al. (1987) *Nature* 329:734-736; Israel & Kaufman (1989) *Nucl. Acidis Res.* 17:2589-2604; and PCT Publication No. WO 93/23431), FK506-related molecules (see e.g., PCT Publication No. WO 94/18317) or tetracyclines (Gossen, M. and Bujard, H. (1992) *Proc. Natl. Acad. Sci. USA* 89:5547-5551; Gossen, M. et al. (1995) *Science* 268:1766-1769; PCT Publication No. WO 94/29442; and PCT Publication No. WO 96/01313). Accordingly, in another embodiment, the invention provides a recombinant expression vector in which T-bet DNA is operatively linked to an inducible eukaryotic promoter, thereby allowing for inducible expression of T-bet protein in eukaryotic cells.

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to T-bet mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to recombinant host cells into which a vector, preferably a recombinant expression vector, of the invention has been introduced. A host cell may be any prokaryotic or eukaryotic cell. For example, T-bet protein may be expressed in bacterial cells such as *E. coli*, insect cells, yeast or mammalian cells (such as Chinese hamster ovary cells (CHO) or COS cells). Other suitable host cells are known to those skilled in the art. Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (*Molecular Cloning: A Laboratory Manual*, 2nd Edition, Cold Spring Harbor Laboratory press (1989)), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker may be introduced into a host cell on the same vector as that encoding T-bet or may be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) T-bet protein. Accordingly, the invention further provides methods for producing T-bet protein using the host cells of the invention. In one embodiment, the method comprises culturing the host cell of invention (into which a recombinant expression vector encoding T-bet has been introduced) in a suitable medium until T-bet is produced. In another embodiment, the method further comprises isolating T-bet from the medium or the host cell. In its native form the T-bet protein is an intracellular protein and, accordingly, recombinant T-bet protein can be expressed intracellularly in a recombinant host cell and then isolated from the host cell, e.g., by lysing the host cell and recovering the recombinant T-bet protein from the lysate. Alternatively, recombinant T-bet protein can be prepared as a extracellular protein by operatively linking a heterologous signal sequence to the amino-terminus of the protein such that the protein is secreted from the host cells. In this case, recombinant T-bet protein can be recovered from the culture medium in which the cells are cultured.

Certain host cells of the invention can also be used to produce nonhuman transgenic animals. For example, in one embodiment, a host cell of the invention is a fertilized oocyte or an embryonic stem cell into which T-bet-coding sequences have been introduced. Such host cells can then be used to create non-human transgenic animals in which exogenous T-bet sequences have been introduced into their genome or homologous recombinant animals in which endogenous T-bet sequences have been altered. Such animals are useful for studying the function and/or activity of T-bet and for identifying and/or evaluating modulators of T-bet activity. Accordingly, another aspect of the invention pertains to non-human transgenic animals which contain cells carrying a transgene encoding a T-bet protein or a portion of a T-bet protein. In a subembodiment, of the transgenic animals of the invention, the transgene alters an endogenous gene encoding an endogenous T-bet protein (e.g., homologous recombinant animals in which the endogenous T-bet gene has been functionally disrupted or "knocked out", or the nucleotide sequence of the endogenous T-bet gene has been mutated or the transcriptional regulatory region of the endogenous T-bet gene has been altered).

A transgenic animal of the invention can be created by introducing T-bet-encoding nucleic acid into the male pronuclei of a fertilized oocyte, e.g., by microinjection, and allowing the oocyte to develop in a pseudopregnant female foster animal. The T-bet nucleotide sequence of SEQ ID NO: 1 or 3 can be introduced as a transgene into the genome of a non-human animal. Intronic sequences and polyadenylation signals can also be included in the transgene to increase the efficiency of expression of the transgene. A tissue-specific regulatory sequencers) can be operably linked to the T-bet transgene to direct expression of T-bet protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the T-bet transgene in its genome and/or expression of T-bet mRNA in tissues or cells of the animals. A transgenic founder animal can then be used to breed additional animals carrying the transgene. Moreover, transgenic animals carrying a transgene encoding T-bet can further be bred to other transgenic animals carrying other transgenes.

To create a homologous recombinant animal, a vector is prepared which contains at least a portion of a T-bet gene into which a deletion, addition or substitution has been introduced to thereby alter, e.g., functionally disrupt, the endogenous T-bet gene. In one embodiment, a homologous recombination vector is designed such that, upon homologous recombination, the endogenous T-bet gene is functionally disrupted (i.e., no longer encodes a functional protein; also referred to as a "knock out" vector). Alternatively, the vector can be designed such that, upon homologous recombination, the endogenous T-bet gene replaced by the T-bet gene. In the homologous recombination vector, the altered portion of the T-bet gene is flanked at its 5' and 3' ends by additional nucleic acid of the T-bet gene to allow for homologous recombination to occur between the exogenous T-bet gene carried by the vector and an endogenous T-bet gene in an embryonic stem cell. The additional flanking T-bet nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced T-bet gene has homologously recombined with the endogenous T-bet gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by gennline transmission of the transgene. Methods for constructing homologous recombination vectors and homologous recombinant animals are described further in Bradley, A. (1991) *Current Opinion in Biotechnology* 2:823-829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In addition to the foregoing, the skilled artisan will appreciate that other approaches known in the art for homologous recombination can be applied to the instant invention. Enzyme-assisted site-specific integration systems are known in the art and can be applied to integrate a DNA molecule at a predetermined location in a second target DNA molecule. Examples of such enzyme-assisted integration systems include the Cre recombinase-lox target system (e.g., as described in Baubonis, W. and Sauer, B. (1993) *Nucl. Acids Res.* 21:2025-2029; and Fukushige, S. and Sauer, B. (1992) *Proc. Natl. Acad. Sci. USA* 89:7905-7909) and the FLP recombinase-FRT target system (e.g., as described in Dang, D. T. and Perrimon, N. (1992) *Dev. Genet.* 13:367-375; and Fiering, S. et al. (1993) *Proc. Natl. Acad. Sci. USA* 90:8469-8473). Tetracycline-regulated inducible homologous recombination systems, such as described in PCT Publication No. WO 94/29442 and PCT Publication No. WO 96/01313, also can be used.

In another embodiment, transgenic animals can be made in which T-bet is expressed in all T cells, e.g., using the CD4 enhancer (Zheng, W-P. & Flavell, R. A. 1997. *Cell* 89, 587). Recent work suggests the CD2 enhancer can also be used. In fact, it is more powerful in achieving high level expression in T cells, expression is not variegated and transgene expression is copy number-dependent (Zhumabekov, T., et al. 1995. *J. Immunol. Meth.* 185, 133; Sharp, L. L., et al. 1997. *Immunity* 7, 609). Mice with high level expression of T-bet RNA (using the human growth hormone intron as a probe to distinguish transgene driven T-bet RNA from endogenous T-bet) can be identified by screening adequate numbers of founders.

In another approach, a dominant repressor transgenic can be created. For example, a dominant-repressor T-bet can be made by using the proximal lck enhancer (Alberola-Ila, J., et al. 1996 *J. Exp. Med.* 184, 9) driving a fusion of T-bet and engrailed can be made (Taylor, D., 1996. *Genes Dev.* 10, 2732; Li, J., Thurm, H., et al. 1997. *Proc. Natl. Acad. Sci. USA* 94, 10885). This construct specifically represses T-bet transactivation of a multimerized T-bet reporter and does not affect NFAT-dependent reporter transactivation.

Alternatively, null mutations can be generated by targeted mutagenesis in ES cells (Ranger, A. M., et al. 1998. *Nature* 392, 186; Hodge, M. R., et al. 1996. *Immunity* 4:1., 144; Grusby, M. J., et al. 1991. *Science* 253, 1417; Reimold, A. M., et al. 1996. *Nature* 379:262; Kaplan, M. H., 1996. *Immunity:* 313; Kaplan, M. H., et al. 1996. *Nature* 382, 174; Smiley, S. T., et al. 1997. *Science* 275, 977). For example using techniques which are known in the art, a genomic T-bet clone can be isolated from a genomic library, the intron-exon organization delineated, and a targeting construct in the cre-lox vector (see discussion below) created which should delete the first exon and 450 hp of upstream promoter sequence. This construct can be electroporated into an ES cell line, and double drug resistant (e.g., neomycin, gancyclovir) clones identified by Southern blot analysis. Clones bearing homologous recombinant events in the T-bet locus can then be identified and injected into blastocysts obtained from day 3.5 BALB/c pregnant mice. Chimeric mice can then be produced and mated to wildtype BALB/c mice to generate germline transmission of the disrupted T-bet gene.

In another embodiment, implantation into RAG2-deficient blastocysts (Chen, J., et al. 1993. *Proc. Natl. Acad. Sci. USA* 90, 4528) or the cre-lox inducible deletion approach can be used to develop mice that are lacking T-bet only in the immune system. For example, the targeting construct can be made in the cre-lox vector. The blastocyst complementation system has been used to study NFATc, an embryonic lethal phenotype (Ranger, A. M., et al. 1998. *Immunity* 8:125). This approach requires disrupting the T-bet gene on both chromosomes in ES cells, which can be accomplished, e.g., by using a mutant neomycin gene and raising the concentration of G418 in the ES cultures, as described (Chen, J., 1993. *Proc. Natl. Acad. Sci. USA* 90; 4528) or by flanking the neo gene with cre-lox sites. To disrupt the second allele, the neomycin gene can be deleted by transfecting the ES clone with the cre recombinase, and then the ES clone can be retransfected with the same targeting construct to select clones with T-bet deletions on both alleles. A third transfection with cre-recombinase yields the desired doubly-deficient ES cells. Such doubly targeted ES cells are then implanted into RAG2 blastocysts and the lymphoid organs of the chimeric mice thus generated will be entirely colonized by the transferred ES cells. This allows assessment of the effect of the absence of T-bet on cells of the lymphoid system without affecting other organ systems where the absence of T-bet might cause lethality.

The conditional ablation approach employing the cre-lox system can also be used. Briefly, a targeting construct is generated in which lox recombination sequences are placed in intronic regions flanking the exons to be deleted. This construct is then transfected into ES cells and mutant mice are generated as above. The resulting mutant mice are then mated to mice transgenic for the cre recombinase driven by an inducible promoter. When cre is expressed, it induces recombination between the introduced lox sites in the T-bet gene, thus effectively disrupting gene function. The key feature of this approach is that gene disruption can be induced in the adult animal at will by activating the cre recombinase.

A tissue-specific promoter can be used to avoid abnormalities in organs outside the immune system. The cre-expressing transgene may be driven by an inducible promoter. Several inducible systems are now being used in cre-lox recombination strategies, the most common being the tetracycline and eedysone systems. A tissue-specific inducible promoter can be used if there is embryonic lethality in the T-bet null mouse.

An alternative approach is to generate a transgenic mouse harboring a regulated T-bet gene (for example using the tetracycline off promoter; e.g., St-Onge, et al. 1996. *Nuc. Acid Res.* 24, 3875-3877) and then breed this transgenic to the T-bet deficient mouse. This approach permits creation of mice with normal T-bet function; tetracycline can be administered to adult animals to induce disruption of T-bet function in peripheral T cells, and then the effect of T-bet deficiency can be examined over time. Repeated cycles of provision and then removal of drug (tetracycline) permits turning the T-bet gene on and off at will.

III. Isolated T-bet Proteins and Anti-T-bet Antibodies

Another aspect of the invention pertains to isolated T-bet proteins. Preferably, the T-bet protein comprises the amino acid sequence encoded by SEQ ID NO:1 or 3. In another preferred embodiment, the protein comprises the amino acid sequence of SEQ ID NO: 2 or 4. In other embodiments, the protein has at least 60% amino acid identity, more preferably 70% amino acid identity, more preferably 80%, and even more preferably, 90% or 95% amino acid identity with the amino acid sequence shown in SEQ ID NO: 2 or 4.

In other embodiments, the invention provides isolated portions of the T-bet protein. For example, the invention further encompasses an amino-terminal portion of T-bet that includes a T-box domain. In various embodiments, this amino terminal portion encompasses at least amino acids 138-327 of human T-bet or at least amino acids 137-326 of mouse T-bet. Another isolated portion of T-bet provided by the invention is a portion encompassing a tyrosine phosphorylation site. This portion encompasses at least amino acids 324-366 and/or 523-534 of human T-bet or amino acids 323-335 or 518-529 of murine T-bet. Yet another isolated portion of T-bet provided herein is a portion encompassing a nuclear localization sequence shown in amino acids 498-501 of human T-bet or 493-496 of murine T-bet.

T-bet proteins of the invention are preferably produced by recombinant DNA techniques. For example, a nucleic acid molecule encoding the protein is cloned into an expression vector (as described above), the expression vector is introduced into a host cell (as described above) and the T-bet protein is expressed in the host cell. The T-bet protein can then be isolated from the cells by an appropriate purification scheme using standard protein purification techniques. Alternative to recombinant expression, a T-bet polypeptide can be synthesized chemically using standard peptide synthesis techniques. Moreover, native T-bet protein can be isolated from cells (e.g., from T cells), for example by immunoprecipitation using an anti-T-bet antibody.

The present invention also pertains to variants of the T-bet proteins which function as either T-bet agonists (mimetics) or as T-bet antagonists. Variants of the T-bet proteins can be generated by mutagenesis, e.g., discrete point mutation or truncation of a T-bet protein. An agonist of the T-bet proteins can retain substantially the same, or a subset, of the biological activities of the naturally occurring form of a T-bet protein. An antagonist of a T-bet protein can inhibit one or more of the activities of the naturally occurring form of the T-bet protein by, for example, competitively modulating a cellular activity of a T-bet protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the T-bet protein. In one embodiment, the invention pertains to derivatives of T-bet which may be formed by modifying at least one amino acid residue of T-bet by oxidation, reduction, or other derivatization processes known in the art.

In one embodiment, variants of a T-bet protein which function as either T-bet agonists (mimetics) or as T-bet antagonists can be identified by screening combinatorial libraries of mutants, e.g, truncation mutants, of a T-bet protein for T-bet protein agonist or antagonist activity. In one embodiment, a variegated library of T-bet variants is generated by combinatorial mutagenesis at the nucleic acid level and is encoded by a variegated gene library. A variegated library of T-bet variants can be produced by, for example, enzymatically ligating a mixture of synthetic oligonucleotides into gene sequences such that a degenerate set of potential T-bet sequences is expressible as individual polypeptides, or alternatively, as a set of larger fusion proteins (e.g., for phage display) containing the set of T-bet sequences therein. There are a variety of methods which can be used to produce libraries of potential T-bet variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential T-bet sequences. Methods for synthesizing degenerate oligonucleotides are known in the art (see, e.g., Narang, S. A., 1983, *Tetrahedron* 39:3, Itakura et al., 1984, *Annu. Rev. Biochem.* 53:323; Itakura et al., 1984, *Science* 198:1056; Ike et al., 1983, *Nucleic Acid Res.* 11:477).

In addition, libraries of fragments of a T-bet protein coding sequence can be used to generate a variegated population of T-bet fragments for screening and subsequent selection of variants of a T-bet protein. In one embodiment, a library of coding sequence fragments can be generated by treating a double stranded PCR fragment of a T-bet coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-termninal and internal fragments of various sizes of the T-bet protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of T-bet proteins. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify T-bet variants (Arkin and Yourvan, 1992, *Proc. Natl. Acad. Sci. USA* 89:7811-7815; Delgrave et al., 1993, *Protein Engineering* 6(3):327-331).

The invention also provides T-bet fusion proteins. As used herein, a T-bet "fusion protein" comprises a T-bet polypeptide operatively linked to a polypeptide other than T-bet. A "T-bet polypeptide" refers to a polypeptide having an amino acid sequence corresponding to T-bet protein, or a peptide fragment thereof which is unique to T-bet protein whereas a "polypeptide other than T-bet" refers to a polypeptide having an amino acid sequence corresponding to another protein. Within the fusion protein, the term "operatively linked" is intended to indicate that the T-bet polypeptide and the other polypeptide are fused in-frame to each other. The other polypeptide may be fused to the N-terminus or C-terminus of the T-bet polypeptide. For example, in one embodiment, the fusion protein is a GST-T-bet fusion protein in which the T-bet sequences are fused to the C-terminus of the GST sequences. In another embodiment, the fusion protein is a T-bet-HA fusion protein in which the T-bet nucleotide sequence is inserted in a vector such as pCEP4-HA vector (Herrscher, R. F. et al. (1995) *Genes Dev.* 9:3067-3082) such that the T-bet sequences are fused in frame to an influenza hemagglutinin epitope tag. Such fusion proteins can facilitate the purification of recombinant T-bet.

Preferably, a T-bet fusion protein of the invention is produced by standard recombinant DNA techniques. For example, DNA fragments coding for the different polypeptide sequences are ligated together in-frame in accordance with conventional techniques, for example employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide or an HA epitope tag). A T-bet-encoding nucleic acid can be cloned into such an expression vector such that the fusion moiety is linked in-frame to the T-bet protein.

An isolated T-bet protein, or fragment thereof, can be used as an immunogen to generate antibodies that bind specifically to T-bet using standard techniques for polyclonal and monoclonal antibody preparation. The T-bet protein can be used to generate antibodies. For example, polyclonal antisera, can be produced in rabbits using full-length recombinant bacterially produced T-bet as the immunogen. This same immunogen can be used to produce mAb by immunizing mice and removing spleen cells from the immunized mice. Spleen cells from mice mounting an immune response to T-bet can be fused to myeloma cells, e.g., SP2/O—Ag14 myeloma. As described in the appended examples, this methods were used to make polyclonal and monoclonal antibodies which bind to T-bet.

Alternatively, an antigenic peptide fragment of T-bet can be used as the immunogen. An antigenic peptide fragment of T-bet typically comprises at least 8 amino acid residues of the amino acid sequence shown in SEQ ID NO: 2 or 4 and encompasses an epitope of T-bet such that an antibody raised against the peptide forms a specific immune complex with T-bet. Preferably, the antigenic peptide comprises at least 10 amino acid residues, more preferably at least 15 amino acid residues, even more preferably at least 20 amino acid residues, and most preferably at least 30 amino acid residues. Preferred epitopes encompassed by the antigenic peptide are regions of T-bet that are located on the surface of the protein, e.g., hydrophilic regions, and that are unique to T-bet. In one embodiment such epitopes can be specific for T-bet proteins from one species, such as mouse or human (i.e., an antigenic peptide that spans a region of T-bet that is not conserved across species is used as immunogen; such non conserved residues can be determined using an alignment such as that provided herein). A standard hydrophobicity analysis of the T-bet protein can be performed to identify hydrophilic regions.

A T-bet immunogen typically is used to prepare antibodies by immunizing a suitable subject, (e.g., rabbit, goat, mouse or other mammal) with the immunogen. An appropriate immunogenic preparation can contain, for examples, recombinantly expressed T-bet protein or a chemically synthesized T-bet peptide. The preparation can further include an adjuvant, such as Freund's complete or incomplete adjuvant, or similar immunostimulatory agent. Immunization of a suitable subject with an immunogenic T-bet preparation induces a polyclonal anti-T-bet antibody response.

Accordingly, another aspect of the invention pertains to anti-T-bet antibodies. Polyclonal anti-T-bet antibodies can be prepared as described above by immunizing a suitable subject with a T-bet immunogen. The anti-T-bet antibody titer in the immunized subject can be monitored over time by standard techniques, such as with an enzyme linked immunosorbent assay (ELISA) using imnmobilized T-bet. If desired, the antibody molecules directed against T-bet can be isolated from the mammal (e.g., from the blood) and further purified by well known techniques, such as protein A chromatography to obtain the IgG fraction. At an appropriate time after immunization, e.g., when the anti-T-bet antibody titers are highest, antibody-producing cells can be obtained from the subject and used to prepare monoclonal antibodies by standard techniques, such as the hybridoma technique originally described by Kohler and Milstein (1975, *Nature* 256:495-497) (see also, Brown et al. (1981) *J. Immunol* 127:539-46; Brown et al. (1980) *J Biol Chem* 255:4980-83; Yeh et al. (1976) *PNAS* 76:2927-31; and Yeh et al. (1982) *Int. J. Cancer* 29:269-75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77-96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387-402; M. L. Gefter et al. (1977) *Somatic Cell Genet.*, 3:231-36). Briefly, an immortal cell line (typically a myeloma) is fused to lymphocytes (typically splenocytes) from a mammal immunized with a T-bet immnunogen as described above, and the culture supernatants of the resulting hybridoma cells are screened to identify a hybridoma producing a monoclonal antibody that binds specifically to T-bet.

Any of the many well known protocols used for fusing lymphocytes and immortalized cell lines can be applied for the purpose of generating an anti-T-bet monoclonal antibody (see, e.g., G. Galfre et al. (1977) *Nature* 266:55052; Gefter et al. *Somatic Cell Genet.*, cited supra; Lemner, *Yale J. Biol. Med.*, cited supra; Kenneth, *Monoclonal Antibodies*, cited supra). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, amninopterin and thymidine ("HAT medium"). Any of a numnber of myeloma cell lines may be used as a fusion partner according to standard techniques, e.g., the P3-NS1/1-Ag4-1, P3-x63-Ag8.653 or Sp2/O—Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind T-bet, e.g., using a standard ELISA assay.

As an alternative to preparing monoclonal antibody-secreting hybridomas, a monoclonal anti-T-bet antibody can be identified and isolated by screening a recombinant combinatorial immunoglobulin library (e.g., an antibody phage display library) with T-bet to thereby isolate immunoglobulin library members that bind T-bet. Kits for generating and screening phage display libraries are commercially available (e.g., the Pharmacia *Recombinant Phage Antibody System*, Catalog No. 27-9400-01; and the *Stratagene* SURF-ZAP™ *Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffiths et al. (1993) *EMBO J* 12:725-734; Hawkins et al. (1992) *J Mol Biol* 226: 889-896; Clarkson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; Barbas et al. (1991) *PNAS* 88:7978-7982, and McCafferty et al. *Nature (*1990) 348:552-554.

Additionally, recombinant anti-T-bet antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Patent Publication PCT/US86/02269; Akira, et al. European Patent Application 184, 187; Taniguchi, M., European Patent Application 171,496; Morrison et al. European Patent Application 173,494; Neuberger et al. PCT Application WO 86/01533; Cabilly et al. U.S. Pat. No. 4,816,567; Cabilly et al. European Patent Application 125,023; Better et al. (1988) *Science* 240:1041-1043; Liu et al. (1987) *PNAS* 84:3439-3443; Liu et al. (1987) *J. Immunol.* 139:3521-3526; Sun et al. (1987) *PNAS* 84:214-218; Nishimura et al. (1987) *Canc. Res.* 47:999-1005; Wood et al. (1985) *Nature* 314:446-449; and Shaw et al. (1988) *J. Natl Cancer Inst.* 80:1553-1559); Morrison, S. L. (1985) *Science* 229:1202-1207; Oi et al. (1986) *BioTechniques* 4:214; Winter U.S. Pat. No. 5,225,539; Jones et al. (1986) *Nature* 321:552-525; Verhoeyan et al. (1988) *Science* 239: 1534; and Beidler et al. (1988) *J. Immunol.* 141:4053-4060.

An anti-T-bet antibody (e.g., monoclonal antibody) can be used to isolate T-bet by standard techniques, such as affinity chromatography or immunoprecipitation. An anti-T-bet antibody can facilitate the purification of natural T-bet from cells and of recombinantly produced T-bet expressed in host cells. Moreover, an anti-T-bet antibody can be used to detect T-bet protein (e.g., in a cellular lysate or cell supernatant). Detection may be facilitated by coupling (i.e., physically linking) the antibody to a detectable substance. Accordingly, in one embodiment, an anti-T-bet antibody of the invention is labeled with a detectable substance. Examples of detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase, examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}$I, $^{131}$I, $^{35}$S or $^{3}$H.

Yet another aspect of the invention pertains to anti-T-bet antibodies that are obtainable by a process comprising:

(a) immunizing an animal with an immunogenic T-bet protein, or an immunogenic portion thereof unique to T-bet protein; and (b) isolating from the animal antibodies that specifically bind to a T-bet protein.

Methods for immunization and recovery of the specific anti-T-bet antibodies are described further above.

IV. Pharmaceutical Compositions

T-bet modulators of the invention (e.g., T-bet inhibitory or stimulatory agents, including T-bet nucleic acid molecules, proteins, antibodies, or compounds identified as modulators of T-bet activity) can be incorporated into pharmaceutical compositions suitable for administration. Such compositions typically comprise the modulatory agent and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. For example, solutions or suspensions used for parenteral, intraden-nal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These may be prepared according to methods known to those skilled in the art, for example, as described in U.S. Pat. No. 4,522,811.

V. Methods of the Invention

Another aspect of the invention pertains to methods of using the various T-bet compositions of the invention. For example, the invention provides a method for detecting the presence of T-bet activity in a biological sample. The method involves contacting the biological sample with an agent capable of detecting T-bet activity, such as T-bet protein or T-bet mRNA, such that the presence of T-bet activity is detected in the biological sample.

A preferred agent for detecting T-bet mRNA is a labeled nucleic acid probe capable of specifically hybridizing to T-bet mRNA. The nucleic acid probe can be, for example, the T-bet DNA of SEQ ID NO: 1 or 3, such as an oligonucleotide of at least about 500, 600, 800, 900, 1000, 1200, 1400, or 1600 nucleotides in length and which specifically hybridizes under stringent conditions to T-bet mRNA.

A preferred agent for detecting T-bet protein is a labeled antibody capable of binding to T-bet protein. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids. For example, techniques for detection of T-bet mRNA include Northern hybridizations and in situ hybridizations. Techniques for detection of T-bet protein include enzyme linked immunosorbent assays (ELISAs), Western blots, immunoprecipitations and immunofluorescence.

Such assays are useful in detecting syndromes characterized by developmental defects. For example, mutations in the human T-box genes TBX5 and TBX3 (orthologs of mouse Tbx5 and Tbx3) are responsible for the autosomal dominant genetic diseases Holt-Oram syndrome and ulnar-mammary syndrome respectively (Bamshad, M., et al. 1997. *Nature Genetics* 16:311; Basson, C. T., et al. 1997. *Nature Genetics* 15:30, Li, Q. Y., et al. 1997. *Nature Genetics* 15: 21; Spranger, S., et al. 1997. *J. Med. Genet.* 3:978). These syndromes are characterized by developmental defects and might have been predicted by the patterns of expression of Tbx5 and Tbx3 respectively. Holt-Oram syndrome affects the heart and upper limbs while ulnar-mammary syndrome affects limb, apocrine gland, tooth and genital development. Both syndromes are characterized by developmental defects and might have been predicted by the patterns of expression of Tbx5 and Tbx3 respectively. The mutations in these patients involve only one allele of the T-box gene—thus it has been postulated that haploinsufficiency of Tbx3 and Tbx5 cause these two diseases. Recently it has been demonstrated that provision of Tbx4 and Tbx5 to developing chick embryos controls limb bud identity (Rodriguez-Esteban et al., 1999; Takeuchi et al., 1999). These discoveries emphasize the critical importance of this family in vertebrate development.

In addition, the existence of T gene homologs in many species provides strong evidence for its function as a transcription factor that regulates a set of as yet unknown target genes involved in mesoderm development. The recent prominence of the T-box family arises from its clear importance in diverse developmental processes, exemplified most dramatically by the T-box mutations in human disease. The generation of mature T cells from thymocyte stem cells and of differentiated Th cells from naive precursors can also be viewed as tightly regulated developmental processes. This discovery that T-bet is responsible for the development of the Th1 lineage demonstrates an important role for this newest T-box family member in the lymphoid system.

The invention further provides methods for identifying compounds that modulate the activity of a T-bet protein. For example, the invention provides a method for identifying a compound that modulates the activity of a T-bet protein, comprising
providing an indicator composition that comprises a T-bet protein;
contacting the indicator composition with a test compound; and
determining the effect of the test compound on the activity of the T-bet protein in the indicator composition to thereby identify a compound that modulates the activity of a T-bet protein.

Specific embodiments of the screening methods of the invention exploit the ability of T-bet proteins to bind to DNA (e.g., the ability to bind to an IL-2 or IFN-gamma promoter) and/or to regulate gene expression (e.g., regulate expression of a Th1-associated cytokine gene, e.g., by repressing the IL-2 gene, transactivate the IFN-γ gene) and/or to redirect polarized Th2 cells into the Th1 pathway.

In a preferred embodiment of the screening assays of the invention, the indicator composition comprises an indicator cell, wherein said indicator cell comprises: (i) the a T-bet protein and (ii) a reporter gene responsive to the T-bet protein. Preferably, the indicator cell contains:
  i) a recombinant expression vector encoding the T-bet; and
  ii) a vector comprising regulatory sequences of a Th1-associated cytokine gene operatively linked a reporter gene; and said method comprising:
    a) contacting the indicator cell with a test compound;
    b) determining the level of expression of the reporter gene in the indicator cell in the presence of the test compound; and
    c) comparing the level of expression of the reporter gene in the indicator cell in the presence of the test compound with the level of expression of the reporter gene in the indicator cell in the absence of the test compound to thereby identify a compound that modulates the activity of T-bet.

In another preferred embodiment, the indicator composition comprises a preparation of: (i) a T-bet protein and (ii) a DNA molecule to which the T-bet binds, and said method comprising:
  a) contacting the indicator composition with a test compound;
  b) determining the degree of interaction of the T-bet protein and the DNA molecule in the presence of the test compound; and
  c) comparing the degree of interaction of the T-bet and the DNA molecule in the presence of the test compound with the degree of interaction of the T-bet protein and the DNA molecule in the absence of the test compound to thereby identify a compound that modulates the activity of T-bet.

Preferably, the DNA molecule to which T-bet binds comprises a T-box binding sequence.

In another preferred embodiment, the method identifies proteins that interact with T-bet. In this embodiment,
the indicator composition is an indicator cell, which indicator cell comprises:
  i) a reporter gene operably linked to a transcriptional regulatory sequence; and
  ii) a first chimeric gene which encodes a first fusion protein, said first fusion protein including T-bet;
the test compound comprises a library of second chimeric genes, which library encodes second fusion proteins;
expression of the reporter gene being sensitive to interactions between the first fusion protein, the second fusion protein and the transcriptional regulatory sequence; and
wherein the effect of the test compound on T-bet in the indicator composition is determined by determining the level of expression of the reporter gene in the indicator cell to thereby identify a test compound comprising a protein that interacts with T-bet.

In a preferred embodiment, the library of second chimeric genes is prepared from cDNA library from Th2 cells.

In a preferred embodiment of the screening assays of the invention, once a test compound is identified as modulating the activity of T-bet, the effect of the test compound on an immune response is then tested. Accordingly, the screening methods of the invention can further comprise determining the effect of the compound on an immune response to thereby identify a compound that modulates an immune response. In one embodiment, the effect of the compound on an immune response is determined by determining the effect of the compound on expression of a Th1-associated cytokine gene, such as an interferon-gamma gene. As used herein, the term "Th1-associated cytokine" is intended to refer to a cytokine that is produced preferentially or exclusively by Th1 cells rather than by Th2 cells. Examples of Th1-associated cytokines include IFN-gamma, IL-2, TNF, and lymphtoxin (LT). In another embodiment, the effect of the compound of interest on an immune response is determined by determining the effect of the compound on development of T helper type 1 (Th1) or T helper type 2 (Th2) cells.

Recombinant expression vectors that can be used for expression of T-bet in the indicator cell are known in the art (see discussions above). In one embodiment, within the expression vector the T-bet-coding sequences are operatively linked to regulatory sequences that allow for constitutive expression of T-bet in the indicator cell (e.g., viral regulatory sequences, such as a cytomegalovirus promoter/enhancer, can be used). Use of a recombinant expression vector that allows for constitutive expression of T-bet in the indicator cell is preferred for identification of compounds that enhance or inhibit the activity of T-bet. In an alternative embodiment, within the expression vector the T-bet-coding sequences are operatively linked to regulatory sequences of the endogenous T-bet gene (i.e., the promoter regulatory region derived from the endogenous T-bet gene). Use of a recombinant expression vector in which T-bet expression is controlled by the endogenous regulatory sequences is preferred for identification of compounds that enhance or inhibit the transcriptional expression of T-bet.

In methods in which a Th1-associated cytokine gene is utilized (e.g., as a reporter gene), preferably, the Th1-associated cytokine is interferon-gamma or IL-2. For example, the IL-2 promoter reveals a T-box binding site at −240 to −220 just 5' of the NF□B site. As described in the appended examples, T-bet was isolated in a yeast one hybrid screening assay based on its ability to bind to the IL-2 promoter. Accordingly, in one embodiment, a method of the invention utilizes a reporter gene construct containing this region of the proximal IL-2 promoter, most preferably nucleotides −240 to −220 of the IL-2 promoter.

A variety of reporter genes are known in the art and are suitable for use in the screening assays of the invention. Examples of suitable reporter genes include those which encode chloramphenicol acetyltransferase, beta-galactosidase, alkaline phosphatase or luciferase. Standard methods for measuring the activity of these gene products are known in the art.

A variety of cell types are suitable for use as an indicator cell in the screening assay. Preferably a cell line is used which does not normally express T-bet, such as a B cell or a Th2 cell clone. Nonlymphoid cell lines can also be used as indicator cells, such as the HepG2 hepatoma cell line. Yeast cells also can be used as indicator cells.

In one embodiment, the level of expression of the reporter gene in the indicator cell in the presence of the test compound is higher than the level of expression of the reporter gene in the indicator cell in the absence of the test compound and the test compound is identified as a compound that stimulates the expression or activity of T-bet. In another embodiment, the level of expression of the reporter gene in the indicator cell in the presence of the test compound is lower than the level of expression of the reporter gene in the indicator cell in the absence of the test compound and the test compound is identified as a compound that inhibits the expression or activity of T-bet.

Alternative to the use of a reporter gene construct, compounds that modulate the expression or activity of T-bet can be identified by using other "read-outs." For example, an indicator cell can be transfected with a T-bet expression vector, incubated in the presence and in the absence of a test compound, and Th1-associated cytokine production can be assessed by detecting cytokine mRNA (e.g., interferon-gamma mRNA) in the indicator cell or cytokine secretion (i.e., interferon-gamma) into the culture supernatant. Standard methods for detecting cytokine mRNA, such as reverse transcription-polymerase chain reaction (RT-PCRt) are known in the art. Standard methods for detecting cytokine protein in culture supernatants, such as enzyme linked immunosorbent assays (ELISA) are also known in the art.

As described above, the invention provides a screening assay for identifying proteins (e.g., proteins in Th1 cells) that interact with T-bet.

In one embodiment, such assays can be designed based on the two-hybrid assay system (also referred to as an interaction trap assay) known in the art (see e.g., Field U.S. Pat. No. 5,283,173; Zervos et al. (1993) Cell 72:223-232; Madura et al. (1993) J. Biol. Chem. 268:12046-12054; Bartel et al. (1993) Biotechniques 14:920-924; and Iwabuchi et al. (1993) Oncogene 8:1693-1696). The two-hybrid assay is generally used for identifying proteins that interact with a particular target protein. The assay employs gene fusions to identify proteins capable of interacting to reconstitute a functional transcriptional activator. The transcriptional activator consists of a DNA-binding domain and a transcriptional activation domain, wherein both domains are required to activate transcription of genes downstream from a target sequence (such as an upstream activator sequence (UAS) for GAL4). DNA sequences encoding a target "bait" protein are fused to either of these domains and a library of DNA sequences is fused to the other domain. "Fish" fusion proteins (generated from the fusion library) capable of binding to the target-fusion protein (e.g., a target GAL4-fusion "bait") will generally bring the two domains (DNA-binding domain and transcriptional activation domain) into close enough proximity to activate the transcription of a reporter gene inserted downstream from the target sequence. Thus, the "fish" proteins can be identified by their ability to reconstitute a functional transcriptional activator (e.g., a functional GAL4 transactivator).

This general two-hybrid system can be applied to the identification of proteins in cells (e.g., Th1 cells) that interact with T-bet by construction of a target T-bet fusion protein (e.g., a T-bet/GAL4 binding domain fusion as the "bait") and a cDNA library of "fish" fusion proteins (e.g., a cDNA/GAL4 activation domain library), wherein the cDNA library is prepared from mRNA of a cell type of interest (e.g., Th1 cells), and introducing these constructs into a host cell that also contains a reporter gene construct linked to a regulatory sequence responsive to T-bet (e.g., an IL-2 promoter sequence, for example, as discussed above). Preferably, the transactivation domain(s) of T-bet will be (which have been mapped to both the 5' and 3' ends) will be deleted in the "bait" construct. In a preferred embodiment, the bait construct will include the T-box domain. In one embodiment, at least one site of tyrosine phosphorylation will also be included. Dominant negative T-bet proteins can also be used to screen for interactors to further localize sites of T-bet which are required for interaction. cDNAs encoding proteins that interact with T-bet can be identified based upon transactivation of the reporter gene construct.

Alternatively, a "single-hybrid" assay, such as that described in Sieweke, M. H. et al. (1996) Cell 85:49-60, can be used to identify proteins that interact with T-bet. This assay is a modification of the two-hybrid system discussed above. In this system, the "bait" is a transcription factor from which the transactivation domain has been removed (e.g., T-bet from which a transactivation domain has been removed) and the "fish" is a non-fusion cDNA library (e.g., a cDNA library prepared from Th1 cells). These constructs are introduced into host cells (e.g., yeast cells) that also contains a reporter gene construct linked to a regulatory sequence responsive to T-bet (e.g., comprising a T-box binding a region, such as a region of the IL-2 promoter responsive to T-bet). cDNAs encoding proteins that interact with T-bet can be identified based upon transactivation of the reporter gene construct.

In another embodiment, representational difference analysis (RDA) and microchip DNA array analysis to isolate T-bet target genes. For example, differential display or subtraction methods coupled with PCR (RDA; see e.g., Hubank, M. & Schatz, D. G. 1994. *Nuc. Acid Res.* 22, 5640-5648; Chang, Y., et al. 1994. *Science* 266, 1865; von Stein, O. D., et al. 1997. *Nuc. Acid Res.* 25, 2598; Lisitsyn, N. & Wigler, M. 1993. *Science* 259, 946) employing subtracted or unsubtracted probes or, most recently, DNA microchip array hybridization (Welford et al. 1998. Nucl. Acids. Res. 15:3059) can be used. In performing such assays, a variety of cells can be used, e.g., normal cells, cells engineered to express T-bet, or cells from mice lacking T-bet or overexpressing T-bet (e.g., from a transgenic non-human animal) can be used.

As described above, the invention provides a screening assay for identifying compounds that modulate the interaction of T-bet and a T-box binding region (e.g., an IL-2 gene regulatory region). Assays are known in the art that detect the interaction of a DNA binding protein with a target DNA sequence (e.g., electrophoretic mobility shift assays, DNAse I footprinting assays and the like). By performing such assays in the presence and absence of test compounds, these assays can be used to identify compounds that modulate (e.g., inhibit or enhance) the interaction of the DNA binding protein with its target DNA sequence.

In one embodiment, the amount of binding of T-bet to the DNA fragment in the presence of the test compound is greater than the amount of binding of T-bet to the DNA fragment in the absence of the test compound, in which case the test compound is identified as a compound that enhances binding of T-bet. In another embodiment, the amount of binding of T-bet to the DNA fragment in the presence of the test compound is less than the amount of binding of T-bet to the DNA fragment in the absence of the test compound, in which case the test compound is identified as a compound that inhibits binding of T-bet.

Yet another aspect of the invention pertains to methods of modulating T-bet activity in a cell. The modulatory methods of the invention involve contacting the cell with an agent that modulates T-bet activity such that T-bet activity in the cell is modulated. The agent may act by modulating the activity of T-bet protein in the cell or by modulating transcription of the T-bet gene or translation of the T-bet mRNA. As used herein, the term "modulating" is intended to include inhibiting or decreasing T-bet activity and stimulating or increasing T-bet activity. Accordingly, in one embodiment, the agent inhibits T-bet activity. In another embodiment, the agent stimulates T-bet activity.

In yet another aspect, the invention provides a method for modulating amount of T helper-type 2 and/or T helper-type 1 cytokines by a cell. The method involves contacting a cell with an agent that modulates the activity of T-bet. For example, agents which stimulate T-bet activity upregulate the Th1 cytokine IFN-gamma, while these same agents down regulate the Th2 cytokine IL-4.

In a further aspect, the invention provides a method for modulating the pattern of cytokines which is produced by a cell. The method involves contacting a cell with an agent that modulates the activity of T-bet. For example, agents which stimulate T-bet activity can induce IFN-gamma production in a cell which does not normally produce IFN-gamma and can repress IL-4 production; such agents can be used, e.g., to redirect the cytokine secretion profile of a Th2 cell to that of a Th1 cell.

A. Inhibitory Agents

According to a modulatory method of the invention, T-bet activity is inhibited in a cell by contacting the cell with an inhibitory agent. Inhibitory agents of the invention can be, for example, intracellular binding molecules that act to inhibit the expression or activity of T-bet. As used herein, the term "intracellular binding molecule" is intended to include molecules that act intracellularly to inhibit the expression or activity of a protein by binding to the protein itself, to a nucleic acid (e.g., an mRNA molecule) that encodes the protein or to a target with which the protein normally interacts (e.g., to a DNA target sequence to which T-bet binds). Examples of intracellular binding molecules, described in further detail below, include antisense T-bet nucleic acid molecules (e.g., to inhibit translation of T-bet mRNA), intracellular anti-T-bet antibodies (e.g., to inhibit the activity of T-bet protein) and dominant negative mutants of the T-bet protein.

In one embodiment, an inhibitory agent of the invention is an antisense nucleic acid molecule that is complementary to a gene encoding T-bet or to a portion of said gene, or a recombinant expression vector encoding said antisense nucleic acid molecule. The use of antisense nucleic acids to downregulate the expression of a particular protein in a cell is well known in the art (see e.g., Weintraub, H. et al., Antisense RNA as a molecular tool for genetic analysis, *Reviews—Trends in Genetics*, Vol. 1(1) 1986; Askari, F. K. and McDonnell, W. M. (1996) *N. Eng. J. Med.* 334:316-318, Bennett, M. R. and Schwartz, S. M. (1995) *Circulation* 92:1981-1993; Mercola, D. and Cohen, J. S. (1995) *Cancer Gene Ther.* 2:47-59; Rossi, J. J. (1995) *Br. Med. Bull* 51:217-225; Wagner, R. W. (1994) *Nature* 372:333-335). An antisense nucleic acid molecule comprises a nucleotide sequence that is complementary to the coding strand of another nucleic acid molecule (e.g., an mRNA sequence) and accordingly is capable of hydrogen bonding to the coding strand of the other nucleic acid molecule. Antisense sequences complementary to a sequence of an mRNA can be complementary to a sequence found in the coding region of the mRNA, the 5' or 3' untranslated region of the mRNA or a region bridging the coding region and an untranslated region (e.g., at the junction of the 5' untranslated region and the coding region). Furthermore, an antisense nucleic acid can be complementary in sequence to a regulatory region of the gene encoding the mRNA, for instance a transcription initiation sequence or regulatory element. Preferably, an antisense nucleic acid is designed so as to be complementary to a region preceding or spanning the initiation codon on the coding strand or in the 3' untranslated region of an mRNA. An antisense nucleic acid for inhibiting the expression of T-bet protein in a cell can be designed based upon the nucleotide sequence encoding the T-bet protein (e.g., SEQ ID NO: 1 or 3), constructed according to the rules of Watson and Crick base pairing.

An antisense nucleic acid can exist in a variety of different formns. For example, the antisense nucleic acid can be an oligonucleotide that is complementary to only a portion of a T-bet gene. An antisense oligonucleotides can be constructed using chemical synthesis procedures known in the art. An antisense oligonucleotide can be chemically synthesized using naturally occurring nucleotides or variously modified nucleotides designed to increase the biological stability of the molecules or to increase the physical stability of the duplex formed between the antisense and sense nucleic acids, e.g. phosphorothioate derivatives and acridine substituted nucleotides can be used. To inhibit T-bet expression in cells in culture, one or more antisense oligonucleotides can be added to cells in culture media, typically at about 200 □g oligonucleotide/ml.

Alternatively, an antisense nucleic acid can be produced biologically using an expression vector into which a nucleic acid has been subcloned in an antisense orientation (i.e., nucleic acid transcribed from the inserted nucleic acid will be of an antisense orientation to a target nucleic acid of interest). Regulatory sequences operatively linked to a nucleic acid cloned in the antisense orientation can be chosen which direct the expression of the antisense RNA molecule in a cell of interest, for instance promoters and/or enhancers or other regulatory sequences can be chosen which direct constitutive, tissue specific or inducible expression of antisense RNA. For example, for inducible expression of antisense RNA, an inducible eukaryotic regulatory system, such as the Tet system (e.g., as described in Gossen, M. and Bujard, H. (1992) *Proc. Natl. Acad. Sci. USA* 89:5547-5551; Gossen, M. et al. (1995) *Science* 268:1766-1769; PCT Publication No. WO 94/29442; and PCT Publication No. WO 96/01313) can be used. The antisense expression vector is prepared as described above for recombinant expression vectors, except that the cDNA (or portion thereof) is cloned into the vector in the antisense orientation. The antisense expression vector can be in the formn of, for example, a recombinant plasmid, phagemid or attenuated virus. The antisense expression vector is introduced into cells using a standard transfection technique, as described above for recombinant expression vectors.

In another embodiment, an antisense nucleic acid for use as an inhibitory agent is ribozyme. Ribozymes are catalytic RNA molecules with ribonuclease activity which are capable of cleaving a single-stranded nucleic acid, such as an mRNA, to which they have a complementary region (for reviews on ribozymes see e.g., Ohkawa, J. et al. (1995) *J. Biochem.* 118:251-258; Sigurdsson, S. T. and Eckstein, F. (1995) *Trends Biotechnol.* 13:286-289; Rossi, J. J. (1995) *Trends Biotechnol.* 13:301-306; Kiehntopf, M. et al. (1995) *J. Mol. Med.* 73:65-71). A ribozyme having specificity for T-bet mRNA can be designed based upon the nucleotide sequence of the T-bet cDNA. For example, a derivative of a Tetrahymena L-19 IVS RNA can be constructed in which the base sequence of the active site is complementary to the base sequence to be cleaved in a T-bet mRNA. See for example U.S. Pat. Nos. 4,987,071 and 5,116,742, both by Cech et al. Alternatively, T-bet mRNA can be used to select a catalytic RNA having a specific ribonuclease activity from a pool of RNA molecules. See for example Bartel, D. and Szostak, J. W. (1993) *Science* 261:1411-1418.

Another type of inhibitory agent that can be used to inhibit the expression and/or activity of T-bet in a cell is an intracellular antibody specific for the T-bet protein. The use of intracellular antibodies to inhibit protein function in a cell is known in the art (see e.g., Carlson, J. R. (1988) *Mol. Cell. Biol.* 8:2638-2646; Biocca, S. et al. (1990) *EMBO J.* 9:101-108; Werge, T. M. et al. (1990) *FEBS Letters* 274: 193-198; Carlson, J. R. (1993) *Proc. Natl. Acad. Sci. USA* 90:7427-7428; Marasco, W. A. et al. (1993) *Proc. Natl. Acad. Sci. USA* 90:7889-7893; Biocca, S. et al. (1994) *Bio/Technology* 12:396-399; Chen, S-Y. et al. (1994) *Human Gene Therapy* 5:595-601; Duan, L et al. (1994) *Proc. Natl. Acad. Sci. USA* 91:5075-5079; Chen, S-Y. et al. (1994) *Proc. Natl. Acad. Sci. USA* 91:5932-5936; Beerli, R. R. et al. (1994) *J. Biol. Chem.* 269:23931-23936; Beerli, R. R. et al. (1994) *Biochem. Biophys. Res. Commun.* 204:666-672; Mhashilkar, A. M. et al. (1995) *EMBO J.* 14:1542-1551; Richardson, J. H. et al. (1995) *Proc. Natl. Acad. Sci. USA* 92:3137-3141; PCT Publication No. WO 94/02610 by Marasco et al.; and PCT Publication No. WO 95/03832 by Duan et al.).

To inhibit protein activity using an intracellular antibody, a recombinant expression vector is prepared which encodes the antibody chains in a form such that, upon introduction of the vector into a cell, the antibody chains are expressed as a functional antibody in an intracellular compartment of the cell. For inhibition of T-bet activity according to the inhibitory methods of the invention, an intracellular antibody that specifically binds the T-bet protein is expressed in the cytoplasm of the cell. To prepare an intracellular antibody expression vector, antibody light and heavy chain cDNAs encoding antibody chains specific for the target protein of interest, e.g., T-bet, are isolated, typically from a hybridoma that secretes a monoclonal antibody specific for the T-bet protein. Hybridomas secreting anti-T-bet monoclonal antibodies, or recombinant anti-T-bet monoclonal antibodies, can be prepared as described above. Once a monoclonal antibody specific for T-bet protein has been identified (e.g., either a hybridoma-derived monoclonal antibody or a recombinant antibody from a combinatorial library), DNAs encoding the light and heavy chains of the monoclonal antibody are isolated by standard molecular biology techniques. For hybridoma derived antibodies, light and heavy chain cDNAs can be obtained, for example, by PCR amplification or cDNA library screening. For recombinant antibodies, such as from a phage display library, cDNA encoding the light and heavy chains can be recovered from the display package (e.g., phage) isolated during the library screening process. Nucleotide sequences of antibody light and heavy chain genes from which PCR primers or cDNA library probes can be prepared are known in the art. For example, many such sequences are disclosed in Kabat, E. A., et al. (1991) *Sequences of Proteins of Immunological Interest, Fifth Edition*, U.S. Department of Health and Human Services, NIH Publication No. 91-3242 and in the "Vbase" human germline sequence database.

Once obtained, the antibody light and heavy chain sequences are cloned into a recombinant expression vector using standard methods. To allow for cytoplasmic expression of the light and heavy chains, the nucleotide sequences encoding the hydrophobic leaders of the light and heavy chains are removed. An intracellular antibody expression vector can encode an intracellular antibody in one of several different forms. For example, in one embodiment, the vector encodes full-length antibody light and heavy chains such that a full-length antibody is expressed intracellularly. In another embodiment, the vector encodes a full-length light chain but only the VH/CH1 region of the heavy chain such that a Fab fragment is expressed intracellularly. In the most preferred embodiment, the vector encodes a single chain antibody (scFv) wherein the variable regions of the light and heavy chains are linked by a flexible peptide linker (e.g., $(Gly_4Ser)_3$) and expressed as a single chain molecule. To inhibit T-bet activity in a cell, the expression vector encoding the anti-T-bet intracellular antibody is introduced into the cell by standard transfection methods, as discussed hereinbefore.

Yet another form of an inhibitory agent of the invention is an inhibitory form of T-bet, also referred to herein as a dominant negative inhibitor, e.g., a form of T-bet in which the tyrosine phosphorylation sites have been mutated or, for example, a mutated form of T-bet in which the transactivation domain has been removed. Such dominant negative T-bet proteins can be expressed in cells using a recombinant expression vector encoding the T-bet protein, which is introduced into the cell by standard transfection methods. To express a mutant form of T-bet lacking tyrosine phosphorylation sites or a transactivation domain, nucleotide sequences encoding a transactivation domain of T-bet are mutated or removed from the T-bet coding sequences by standard recombinant DNA techniques. The truncated DNA is inserted into a recombinant expression vector, which is then introduced into a cell to allow for expression of the altered form of T-bet, in the cell.

Other inhibitory agents that can be used to inhibit the activity of a T-bet protein are chemical compounds that directly inhibit T-bet activity or inhibit the interaction between T-bet and target DNA or another protein. Such compounds can be identified using screening assays that select for such compounds, as described in detail above.

B. Stimulatory Agents

According to a modulatory method of the invention, T-bet activity is stimulated in a cell by contacting the cell with a stimulatory agent. Examples of such stimulatory agents include active T-bet protein and nucleic acid molecules encoding T-bet that are introduced into the cell to increase T-bet activity in the cell. A preferred stimulatory agent is a nucleic acid molecule encoding a T-bet protein, wherein the nucleic acid molecule is introduced into the cell in a form suitable for expression of the active T-bet protein in the cell. To express a T-bet protein in a cell, typically a T-bet-encoding DNA is first introduced into a recombinant expression vector using standard molecular biology techniques, as described herein. A T-bet-encoding DNA can be obtained, for example, by amplification using the polymerase chain reaction (PCR), using primers based on the T-bet nucleotide sequence. Following isolation or amplification of T-bet-encoding DNA, the DNA fragment is introduced into an expression vector and transfected into target cells by standard methods, as described herein.

Other stimulatory agents that can be used to stimulate the activity of a T-bet protein are chemical compounds that stimulate T-bet activity in cells, such as compounds that directly stimulate T-bet protein and compounds that promote the interaction between T-bet and target DNA or other proteins. Such compounds can be identified using screening assays that select for such compounds, as described in detail above.

The modulatory methods of the invention can be performed in vitro (e.g., by culturing the cell with the agent or by introducing the agent into cells in culture) or, alternatively, in vivo (e.g., by administering the agent to a subject or by introducing the agent into cells of a subject, such as by gene therapy). For practicing the modulatory method in vitro, cells can be obtained from a subject by standard methods and incubated (i.e., cultured) in vitro with a modulatory agent of the invention to modulate T-bet activity in the cells. For example, peripheral blood mononuclear cells (PBMCs) can be obtained from a subject and isolated by density gradient centrifugation, e.g., with Ficoll/Hypaque. Specific cell populations can be depleted or enriched using standard methods. For example, T cells can be enriched for example, by positive selection using antibodies to T cell surface markers, for example by incubating cells with a specific primary monoclonal antibody (mAb), followed by isolation of cells that bind the mAb using magnetic beads coated with a secondary antibody that binds the primary mAb. Specific cell populations can also be isolated by fluorescence activated cell sorting according to standard methods. If desired, cells treated in vitro with a modulatory agent of the invention can be readministered to the subject. For administration to a subject, it may be preferable to first remove residual agents in the culture from the cells before administering them to the subject. This can be done for example by a Ficoll/Hypaque gradient centrifugation of the cells. For further discussion of ex vivo genetic modification of cells followed by readministration to a subject, see also U.S. Pat. No. 5,399,346 by W. F. Anderson et al.

For practicing the modulatory method in vivo in a subject, the modulatory agent can be administered to the subject such that T-bet activity in cells of the subject is modulated. The term "subject" is intended to include living organisms in which an immune response can be elicited. Preferred subjects are mammals. Examples of subjects include humans, monkeys, dogs, cats, mice, rats, cows, horses, goats and sheep.

For stimulatory or inhibitory agents that comprise nucleic acids (including recombinant expression vectors encoding T-bet protein, antisense RNA, intracellular antibodies or dominant negative inhibitors), the agents can be introduced into cells of the subject using methods known in the art for introducing nucleic acid (e.g., DNA) into cells in vivo. Examples of such methods encompass both non-viral and viral methods, including:

Direct Injection: Naked DNA can be introduced into cells in vivo by directly injecting the DNA into the cells (see e.g., Acsadi et al. (1991) *Nature* 332:815-818, Wolff et al. (1990) *Science* 247:1465-1468). For example, a delivery apparatus (e.g., a "gene gun") for injecting DNA into cells in vivo can be used. Such an apparatus is commercially available (e.g., from BioRad).

Cationic Lipids: Naked DNA can be introduced into cells in vivo by complexing the DNA with cationic lipids or encapsulating the DNA in cationic liposomes. Examnples of suitable cationic lipid formulations include N-[-1-(2,3-dioleoyloxy)propyl]N,N,N-triethylammonium chloride (DOTMA) and a 1:1 molar ratio of 1,2-dimyristyloxy-propyl-3-dimethylhydroxyethylammonium bromide (DMRIE) and dioleoyl phosphatidylethanolamine (DOPE) (see e.g., Logan, J. J. et al. (1995) *Gene Therapy* 2:38-49; San, H. et al. (1993) *Human Gene Therapy* 4:781-788).

Receptor-Mediated DNA Uptake: Naked DNA can also be introduced into cells in vivo by complexing the DNA to a cation, such as polylysine, which is coupled to a ligand for a cell-surface receptor (see for example Wu, G. and Wu, C. H. (1988) *J. Biol. Chem.* 263:14621; Wilson et al. (1992) *J. Biol. Chem.* 267:963-967; and U.S. Pat. No. 5,166,320). Binding of the DNA-ligand complex to the receptor facilitates uptake of the DNA by receptor-mediated endocytosis. A DNA-ligand complex linked to adenovirus capsids which naturally disrupt endosomes, thereby releasing material into the cytoplasm can be used to avoid degradation of the complex by intracellular lysosomes (see for example Curiel et al. (1991) *Proc. Natl. Acad. Sci. USA* 88:8850; Cristiano et al. (1993) *Proc. Natl. Acad. Sci. USA* 90:2122-2126).

Retroviruses: Defective retroviruses are well characterized for use in gene transfer for gene therapy purposes (for a review see Miller, A. D. (1990) *Blood* 76:271). A recombinant retrovirus can be constructed having a nucleotide sequences of interest incorporated into the retroviral genome. Additionally, portions of the retroviral genome can be removed to render the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines include ψCrip, ψCre, ψ2 and ψAm. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) *Science* 230:1395-1398; Danos and Mulligan (1988) *Proc. Natl. Acad. Sci. USA* 85:6460-6464; Wilson et al. (1988) *Proc. Natl. Acad. Sci. USA* 85:3014-3018; Armentano et al. (1990) *Proc. Natl. Acad. Sci. USA* 87:6141-6145; Huber et al. (1991) *Proc. Natl. Acad. Sci. USA* 88:8039-8043; Ferry et al. (1991) *Proc. Natl. Acad. Sci. USA* 88:8377-8381; Chowdhury et al. (1991) *Science* 254:1802-1805; van Beusechem et al. (1992) *Proc. Natl. Acad. Sci. USA* 89:7640-7644; Kay et al. (1992) *Human Gene Therapy* 3:641-647; Dai et al. (1992) *Proc. Natl. Acad. Sci. USA* 89:10892-10895; Hwu et al. (1993) *J. Immunol.* 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573). Retroviral vectors require target cell division in order for the retroviral genome (and foreign nucleic acid inserted into it) to be integrated into the host genome to stably introduce nucleic acid into the cell. Thus, it may be necessary to stimulate replication of the target cell.

Adenoviruses: The genome of an adenovirus can be manipulated such that it encodes and expresses a gene product of interest but is inactivated in terms of its ability to replicate in a normal lytic viral life cycle. See for example Berkner et al. (1988) *BioTechniques* 6:616; Rosenfeld et al. (1991) *Science* 252:431-434; and Rosenfeld et al. (1992) *Cell* 68:143-155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) *Proc. Natl. Acad. Sci. USA* 89:6482-6486), hepatocytes (Herz and Gerard (1993) *Proc. Natl. Acad. Sci. USA* 90:2812-2816) and muscle cells (Quantin et al. (1992) *Proc. Natl. Acad. Sci. USA* 89:2581-2584). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267). Most replication-defective adenoviral vectors currently in use are deleted for all or parts of the viral E1 and E3 genes but retain as much as 80% of the adenoviral genetic material.

Adeno-Associated Viruses: Adeno-associated virus (AAV) is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97-129). It is also one of the few viruses that may integrate its DNA into non-dividing cells, and exhibits a high frequency of stable integration (see for example Flotte et al. (1992) *Am. J. Respir. Cell. Mol. Biol.* 7:349-356; Samulski et al. (1989) *J. Virol.* 63:3822-3828; and McLaughlin et al. (1989) *J. Virol.* 62:1963-1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251-3260 can be used to introduce DNA into cells. A variety of nucleic acids have been introduced into different cell types using AAV vectors (see for example Hennonat et al. (1984) *Proc. Natl. Acad. Sci. USA* 81:6466-6470; Tratschin et al. (1985) *Mol. Cell. Biol.* 4:2072-2081; Wondisford et al. (1988) *Mol. Endocrinol.* 2:32-39; Tratschin et al. (1984) *J. Virol.* 51:611-619; and Flotte et al. (1993) *J. Biol. Chem.* 268:3781-3790).

The efficacy of a particular expression vector system and method of introducing nucleic acid into a cell can be assessed by standard approaches routinely used in the art. For example, DNA introduced into a cell can be detected by a filter hybridization technique (e.g., Southern blotting) and RNA produced by transcription of introduced DNA can be detected, for example, by Northern blotting, RNase protection or reverse transcriptase-nolymerase chain reaction (RT-PCR). The gene product can be detected by an appropriate assay, for example by immunological detection of a produced protein, such as with a specific antibody, or by a functional assay to detect a functional activity of the gene product.

In a prefer-red embodiment, a retroviral expression vector encoding T-bet is used to express T-bet protein in cells in vivo, to thereby stimulate T-bet protein activity in vivo. Such retroviral vectors can be prepared according to standard methods known in the art (discussed further above).

A modulatory agent, such as a chemical compound, can be administered to a subject as a pharmaceutical composition. Such compositions typically comprise the modulatory agent and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Pharmaceutical compositions can be prepared as described above in subsection IV.

The identification of T-bet as a key regulator of the development of Th1 cells described herein, and in the repression of the Th2 phenotype, allows for selective manipulation of T cell subsets in a variety of clinical situations using the modulatory methods of the invention. The stimulatory methods of the invention (i.e., methods that use a stimulatory agent to enhance T-bet activity) result in production of IFN-gamma, with concomitant promotion of a Th1 response and downregulation of both IL-2 and IL-4, thus dowrnmodulating the Th2 response. In contrast, the inhibitory methods of the invention (i.e., methods that use an inhibitory agent to downtodulate T-bet activity) inhibit the production of IFN-gamma, with concomitant downregulation of a Th1 response and promotion of a Th2 response. Thus, to treat a disease condition wherein a Th1 response is beneficial, a stimulatory method of the invention is selected such that Th1 responses are promoted while downregulating Th2 responses. Alternatively, to treat a disease condition wherein a Th2 response is beneficial, an inhibitory method of the invention is selected such that Th1 responses are downregulated while promoting Th2 responses. Application of the methods of the invention to the treatment of disease conditions may result in cure of the condition, a decrease in the type or number of symptoms associated with the condition, either in the long term or short term (i.e., amelioration of the condition) or simply a transient beneficial effect to the subject.

Numerous disease conditions associated with a predominant Th1 or Th2-type response have been identified and could benefit from modulation of the type of response mounted in the individual suffering from the disease condition. Application of the immunomodulatory methods of the invention to such diseases is described in further detail below.

A. Allergies

Allergies are mediated through IgE antibodies whose production is regulated by the activity of Th2 cells and the cytokines produced thereby. In allergic reactions, IL-4 is produced by Th2 cells, which further stimulates production of IgE antibodies and activation of cells that mediate allergic reactions, i.e., mast cells and basophils. IL-4 also plays an important role in eosinophil mediated inflammatory reactions. Accordingly, the stimulatory methods of the invention can be used to inhibit the production of Th2-associated cytokines, and in particular IL-4, in allergic patients as a means to downregulate production of pathogenic IgE antibodies. A stimulatory agent may be directly administered to the subject or cells (e.g., Thp cells or Th2 cells) may be obtained from the subject, contacted with a stimulatory agent ex vivo, and readministered to the subject. Moreover, in certain situations it may be beneficial to coadminister to the subject the allergen together with the stimulatory agent or cells treated with the stimulatory agent to inhibit (e.g., desensitize) the allergen-specific response. The treatment may be further enhanced by administering other Th1-promoting agents, such as the cytokine IL-12 or antibodies to Th2-associated cytokines (e.g., anti-IL-4 antibodies), to the allergic subject in amounts sufficient to further stimulate a Th1-type response.

B. Cancer

The expression of Th2-promoting cytokines has been reported to be elevated in cancer patients (see e.g., Yamamura, M., et al. (1993) *J. Clin. Invest.* 91:1005-1010; Pisa, P., et al. (1992) *Proc. Natl. Acad. Sci. USA* 89:7708-7712) and malignant disease is often associated with a shift from Th1 type responses to Th2 type responses along with a worsening of the course of the disease. Accordingly, the stimulatory methods of the invention can be used to inhibit the production of Th2-associated cytokines in cancer patients, as a means to counteract the Th1 to Th2 shift and thereby promote an ongoing Th1 response in the patients to ameliorate the course of the disease. The stimulatory method can involve either direct administration of an stimulatory agent to a subject with cancer or ex vivo treatment of cells obtained from the subject (e.g., Tbp or Tb2 cells) with a stimulatory agent followed by readministration of the cells to the subject. The treatment may be further enhanced by administering other Th1-promoting agents, such as the cytokine IL-12 or antibodies to Th2-associated cytokines (e.g., anti-IL-4 antibodies), to the recipient in amounts sufficient to further stimulate a Th1-type response.

C. Infectious Diseases

The expression of Th2-promoting cytokines also has been reported to increase during a variety of infectious diseases, including HIV infection, tuberculosis, leishmaniasis, schistosomiasis, filarial nematode infection and intestinal nematode infection (see e.g.; Shearer, G. M. and Clerici, M. (1992) *Prog. Chem. Immunol.* 54:21-43; Clerici, M and Shearer, G. M. (1993) *Immunology Today* 14:107-111; Fauci, A. S. (1988) *Science* 239:617-623; Locksley, R. M. and Scott, P. (1992) *Immunoparasitology Today* 1:A58-A61; Pearce, E. J., et al. (1991) *Exp. Med.* 173:159-166; Grzych, J-M., et al. (1991) *J. Immunol.* 141:1322-1327; Kullberg, M. C., et al. (1992) *J. Immunol.* 148:3264-3270; Bancroft, A. J., et al. (1993) *J. Immunol.* 150:1395-1402; Pearlman, E., et al. (1993) *Infect. Immun.* 61:1105-1112; Else, K. J., et al. (1994) *J. Exp. Med.* 179:347-351) and such infectious diseases are also associated with a Th1 to Th2 shift in the immune response. Accordingly, the stimulatory methods of the invention can be used to inhibit the production of Th2-associated cytokines in subjects with infectious diseases, as a means to counteract the Th1 to Th2 shift and thereby promote an ongoing Th1 response in the patients to ameliorate the course of the infection. The stimulatory method can involve either direct administration of an inhibitory agent to a subject with an infectious disease or ex vivo treatment of cells obtained from the subject (e.g., Thp or Th2 cells) with a stimulatory agent followed by readministration of the cells to the subject. The treatment may be further enhanced by administering other Th1-promoting agents, such as the cytokine IL-12 or antibodies to Th2-associated cytokines (e.g., anti-IL-4 antibodies), to the recipient in amounts sufficient to further stimulate a Th1-type response.

D. Autoimmune Diseases

The inhibitory methods of the invention can be used therapeutically in the treatment of autoimmune diseases that are associated with a Th2-type dysfunction. Many autoimmune disorders are the result of inappropriate activation of T cells that are reactive against self tissue and that promote the production of cytokines and autoantibodies involved in the pathology of the diseases. Modulation of T helper-type responses can have an effect on the course of the autoimmune disease. For example, in experimental allergic encephalomyelitis (EAE), stimulation of a Th2-type response by administration of IL-4 at the time of the induction of the disease diminishes the intensity of the autoimmune disease (Paul, W. E., et al. (1994) *Cell* 76:241-251). Furthermore, recovery of the animals from the disease has been shown to be associated with an increase in a Th2-type response as evidenced by an increase of Th2-specific cytokines (Koury, S. J., et al. (1992) *J. Exp. Med.* 176:1355-1364). Moreover, T cells that can suppress EAE secrete Th2-specific cytokines (Chen, C., et al. (1994) *Immunity* 1:147-154). Since stimulation of a Th2-type response in EAE has a protective effect against the disease, stimulation of a Th2 response in subjects with multiple sclerosis (for which EAE is a model) is likely to be beneficial therapeutically. The inhibitory methods of the invention can be used to affect such a decrease.

Similarly, stimulation of a Th2-type response in type I diabetes in mice provides a protective effect against the disease. Indeed, treatment of NOD mice with IL-4 (which promotes a Th2 response) prevents or delays onset of type I diabetes that normally develops in these mice (Rapoport, M. J., et al. (1993) *J. Exp. Med.* 178:87-99). Thus, stimulation of a Th2 response in a subject suffering from or susceptible to diabetes may ameliorate the effects of the disease or inhibit the onset of the disease.

Yet another autoimmune disease in which stimulation of a Th2-type response may be beneficial is rheumatoid arthritis (RA). Studies have shown that patients with rheumatoid arthritis have predominantly Th1 cells in synovial tissue (Simon, A. K., et al., (1994) *Proc. Natl. Acad. Sci. USA* 91:8562-8566). By stimulating a Th2 response in a subject with RA, the detrimental Th1 response can be concomitantly downmodulated to thereby ameliorate the effects of the disease.

Accordingly, the inhibitory methods of the invention can be used to stimulate production of Th2-associated cytokines in subjects suffering from, or susceptible to, an autoimmune disease in which a Th2-type response is beneficial to the course of the disease. The inhibitory method can involve either direct administration of an inhibitory agent to the subject or ex vivo treatment of cells obtained from the subject (e.g., Thp, Th1 cells, B cells, non-lymphoid cells) with an inhibitory agent followed by readministration of the cells to the subject. The treatment may be further enhanced by administering other Th2-promoting agents, such as IL-4 itself or antibodies to Th1-associated cytokines, to the subject in amounts sufficient to further stimulate a Th2-type response.

In contrast to the autoimmune diseases described above in which a Th2 response is desirable, other autoimmune diseases may be ameliorated by a Th1-type response. Such diseases can be treated using a stimulatory agent of the invention (as described above for cancer and infectious diseases). The treatment may be further enhanced by administrating a Th1-promoting cytokine (e.g., IFN-γ) to the subject in amounts sufficient to further stimulate a Th1-type response.

The efficacy of agents for treating autoimmune diseases can be tested in the above described animal models of human diseases (e.g., EAE as a model of multiple sclerosis and the NOD mice as a model for diabetes) or other well characterized animal models of human autoimmnune diseases. Such animal models include the mrl/lpr/lpr mouse as a model for lupus erythematosus, murine collagen-induced arthritis as a model for rheumatoid arthritis, and murine experimental myasthenia gravis (see Paul ed., *Fundamental Immunology*, Raven Press, New York, 1989, pp. 840-856). A modulatory (i.e., stimulatory or inhibitory) agent of the invention is administered to test animals and the course of the disease in the test animals is then monitored by the standard methods for the particular model being used. Effectiveness of the modulatory agent is evidenced by amelioration of the disease condition in animals treated with the agent as compared to untreated animals (or animals treated with a control agent).

Non-limiting examples of autoimmune diseases and disorders having an autoimmune component that may be treated according to the invention include diabetes mellitus, arthritis (including rheumatoid arthritis, juvenile rheumatoid arthritis, osteoarthritis, psoriatic arthritis), multiple sclerosis, myasthenia gravis, systemic lupus erythematosus, autoimmune thyroiditis, dermatitis (including atopic dermatitis and eczematous dermatitis), psoriasis, Sjögren's Syndrome, including keratoconjunctivitis sicca secondary to Sjögren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Crohn's disease, Graves ophthalmopathy, sarcoidosis, primary biliary cirrhosis, uveitis posterior, and interstitial lung fibrosis.

E. Transplantation

While graft rejection or graft acceptance may not be attributable exclusively to the action of a particular T cell subset (i.e., Th1 or Th2 cells) in the graft recipient (for a discussion see Dallman, M. J. (1995) *Curr. Opin. Immunol.* 7:632-638), numerous studies have implicated a predominant Th2 response in prolonged graft survival or a predominant Th2 response in graft rejection. For example, graft acceptance has been associated with production of a Th2 cytokine pattern and/or graft rejection has been associated with production of a Th1 cytokine pattern (see e.g., Takeuchi, T. et al. (1992) *Transplantation* 53:1281-1291; Tzakis, A. G. et al. (1994) *J. Pediatr. Surg* 29:754-756; Thai, N. L. et al. (1995) *Transplantation* 5 9:274-2 81). Additionally, adoptive transfer of cells having a Th2 cytokine phenotype prolongs skin graft survival (Maeda, H. et al. (1994) *Int. Immunol.* 6:855-862) and reduces graft-versus-host disease (Fowler, D. H. et al. (1994) *Blood* 84:3540-3549; Fowler, D. H. et al. (1994) *Prog. Clin. Biol. Res.* 389:533-540). Still further, administration of IL-4, which promotes Th2 differentiation, prolongs cardiac allograft survival (Levy, A. E. and Alexander, J. W. (1995) *Transplantation* 60:405-406), whereas administration of IL-12 in combination with anti-IL-10 antibodies, which promotes Th1 differentiation, enhances skin allograft rejection (Gorczynski, R. M. et al. (1995) *Transplantation* 60:1337-1341).

Accordingly, the inhibitory methods of the invention can be used to stimulate production of Th2-associated cytokines in transplant recipients to prolong survival of the graft. The inhibitory methods can be used both in solid organ transplantation and in bone marrow transplantation (e.g., to inhibit graft-versus-host disease). The inhibitory method can involve either direct administration of an inhibitory agent to the transplant recipient or ex vivo treatment of cells obtained from the subject (e.g., Thp, Th1 cells, B cells, non-lymphoid cells) with an inhibitory agent followed by readministration of the cells to the subject. The treatment may be further enhanced by administering other Th2-promoting agents, such as IL-4 itself or antibodies to Th 1-associated cytokines, to the recipient in amounts sufficient to further inhibit a Th2-type response.

In addition to the foregoing disease situations, the modulatory methods of the invention also are useful for other purposes. For example, the stimulatory methods of the invention (i.e., methods using a stimulatory agent) can be used to stimulate production of Th1-promoting cytokines (e.g., interferon-gamma) in vitro for commercial production of these cytokines (e.g., cells can be contacted with the stimulatory agent in vitro to stimulate interferon-gamma production and the interferon-gamma can be recovered from the culture supernatant, further purified if necessary, and packaged for commercial use).

Furthermore, the modulatory methods of the invention can be applied to vaccinations to promote either a Th1 or a Th2 response to an antigen of interest in a subject. That is, the agents of the invention can serve as adjuvants to direct an immune response to a vaccine either to a Th1 response or a Th2 response. For example, to promote an antibody response to an antigen of interest (i.e., for vaccination purposes), the antigen and an inhibitory agent of the invention can be coadministered to a subject to promote a Th2 response to the antigen in the subject, since Th2 responses provide efficient B cell help and promote IgG1 production. Alternatively, to promote a cellular immune response to an antigen of interest, the antigen and a stimulatory agent of the invention can be coadministered to a subject to promote a Th1 response to the antigen in a subject, since Th1 responses favor the development of cell-mediated immune responses (e.g., delayed hypersensitivity responses). The antigen of interest and the modulatory agent can be formulated together into a single pharmaceutical composition or in separate compositions. In a preferred embodiment, the antigen of interest and the modulatory agent are administered simultaneously to the subject. Alternatively, in certain situations it may be desirable to administer the antigen first and then the modulatory agent or vice versa (for example, in the case of an antigen that naturally evokes a Th1 response, it may be beneficial to first administer the antigen alone to stimulate a Th1 response and then administer an inhibitory agent, alone or together with a boost of antigen, to shift the immune response to a Th2 response).

This invention is further illustrated by the following example, which should not be construed as limiting. The contents of all references, patents and published patent applications cited throughout this application are hereby incorporated by reference. Additionally, all nucleotide and amino acid sequences deposited in public databases referred to herein are also hereby incorporated by reference.

A nucleic acid molecule comprising a mouse T-bet cDNA cloned into the EcoRI site of the pJG4-5 vector was deposited with the American Type Culture Collection (Manassas, Va.) on Nov. 9, 1999 and assigned Deposit Number PTA-930. A nucleic acid molecule comprising a human T-bet cDNA (prepared from RNA from the human Th1 clone ROT-10) cloned into the PCR 2.1-TOPO vector was deposited with the American Type Culture Collection (Manassas, Va.) on Jan. 28, 2000 and assigned Deposit Number PTA-1339. Both deposits were made under the provisions of the Budapest Treaty.

EXAMPLES

The following experimental procedures were used in the examples:

Mice, Cell Lines, Cytokines, Antibodies and Plasmids

BALB/c mice were obtained from Jackson Laboratories, DO11.10 TcR-transgenic mice (Jacobson, N. G., et al. 1995. J. Exp. Med. 181, 1755-1762), and MBP TcR-transgenic mice (Lafaille, J. J., 1994. Cell 78, 399-408.) have been described. Mice were used at 5-6 weeks of age. Cell lines and primary cells were maintained in complete medium containing RPMI 1640 supplemented with 10% fetal calf serum (HyClone Laboratories), glutamine (2 mM), penicillin (50 units/ml), streptomycin (50 □g/ml), Hepes (100 mM) and □-ME (50 □M). Jurkat is a human Th1 lymphoma, EL4 a mouse Th0 thymoma, NK3.3 a human NK cell line (Ye, J., 1995. J. Leuko. Biol. 58, 225-233., Kornbluth, J., 1982. J. Immunol. 129, 2831-2837), YT a human NK cell line (Yodoi, J., 1985. J. of Immuno. 134, 1623-1630), AE7 a mouse Th1 clone, D10 a mouse Th2 clone and M12 is a B cell lymphoma line. Recombinant IL-4 was obtained from DNAX, human rIL-2 was obtained from Chiron Corp., rIL-12 was obtained from Hoffman LaRoche, and rIL-18 was purchased from Peprotech, Inc. Monoclonal anti-IL-12, monoclonal anti-IFN-γ and monoclonal anti-IL-4 (11B11) were also used (Ohara, J. and Paul, W. E. 1985. Nature 315, 333-336). Both the T-bet polyclonal antisera, produced in rabbits, and the mAb were raised against full-length recombinant bacterially produced T-bet. The mAb was produced by fusion of spleen cells from mice to the SP2/O-Ag14 myleoma and is of the IgG1 subtype. Expression plasmids included c-Maf (pMex-maf)(Ho, I-C., et al. 1996. Cell 85, 973-983.). NFATp (Hodge, M. R., et al. 1996. Immunity 4, 1-20) and p65, the latter two cloned into the pCDNA vector.

CD4+ T Cell Purification and In Vitro Cultures

CD4+ T cells were purified from lymph nodes (LN) by flow cytometry using PE-conjugated anti CD4 (RM4-4) (Pharmingen) and sorted using FACS (Mo Flo, Becton Dickenson) to 98-99% purity. For in vitro activation $2 \times 10^6$/ml CD4+ cells were resuspended in complete medium and activated with plate-bound 1 □g/ml anti CD3 (2C11) and 20 g/ml anti CD928 (Pharmingen) for 3 days in the presence of 100 units/ml IL2. Cells were then split 1:4 in complete medium and cultured for 4 days in the presence of 100 units/ml IL2. On day 7 after primary stimulation, cells were harvested, washed twice and restimulated at $1 \times 10^6$ cells/ml with 1 □g/ml plate-bound anti CD3 for 1, 3 and 6 hours. For Th1 and Th2 differentiation cultures, non-transgenic or DO11.10 LN and spleen cells were pooled, resuspended in $1 \times 10^6$ cells/ml complete medium and cultured under Th1 (10 mg/ml anti IL4 [11B11], 10 ng/ml rIL 12) or Th2 (10 mg/ml anti IFNγ, 10 ng/ml IL4) conditions with 1 ug/mi plate-bound anti CD3. Cells were split 1:4 on day 3 with complete medium+100 u/ml IL2. On day 7, cells were restimulated with 1 □g/ml anti CD3 for 4 hours and harvested for RNA preparation (Jacobson, N. G., et al. 1995). J. Exp. Med. 181, 1755-1762). Supernatants were taken at 24 hours to test for cytokines.

Northern and Western Blot Analysis

Total RNA was isolated from resting and stimulated cells using TRIZOL reagent (Gibco/BRL) and 10 □g of each sample separated on 1.2% agarose 6% formaldehyde gels, transferred onto Genescreen membrane (NEN) in 20× SSC overnight and covalently bound using a UV Stratalinker (Stratagene). Hybridization of blots was carried out at 42° C. as described (Hodge, M. R., et al. 1996. Immunity 4, 1-20) using the following cDNA probes labeled with 32P: T-bet, □-actin. Nuclear and cytoplasmic extracts for western blot analysis were prepared from AE7, D10 and NK3.3 cells. Nuclei were isolated as described (Dolmetsch, R. E., et al. 1997. Nature 386, 855-858). Extracted proteins were separated by 8% PAGE followed by electrotransfer to nitrocellulose membranes and probed with a mAb specific for T-bet followed by horseradish peroxidase-conjugated goat anti-mouse IgG and enhanced chemiluminescence according to the instructions of the manufacturer (Amersham).

Transient Transfection Assays

EL4 and Jurkat cells were transfected using a Bio Rad electroporator (280V, 975 □□F) using $5 \times 10^6$ cells in 0.4 ml RPMI per transfection with 5 □g reporter plasmid and 5-10 □□g expression plasmid. Luciferase assays were perforrned after 24 hrs with the luciferase activity in 20% of each sample measured as per instructions (Promega). The IFN-γ reporter-luciferase construct is derived from the plasmid pB9 which contains the entire human IFN-gamma gene (P. Gray and D. V. Goeddel. 1982. Nature. 298:859). The pGL2 luciferase gene was inserted into the first exon of pB9. IL-2-promoter-reporter construct The IL-4 promoter reporter construct, IL-4Luc, contains 807 bp upstream of the murine IL-4 gene.

Retroviral Constructs and Transduction

The GFP-RV bicistronic vector has been described (Ouyang, W., et al. 1998. Immunity 9:745-755) as has the Phoenix-Eco packaging cell line (Kinoshita, S., et al. 1998. Cell 95, 595-604). The GFP-RV vector was constructed by inserting the encephalomyocarditis virus internal ribosomal entry sequence (IRES) and the GFP allele into the MSCV2.2 retroviral vector (Ouyang, W., et al. 1998. Immunity 9.-745-755) or IL-2-MSCV vector. Both vectors express two cDNAs, T-bet and the cDNA encoding GFP, simultaneously using an IRES to initiate translation of each mRNA separately. Transfection of the packaging cell line and retroviral transductions of primary r cells were performed essentially as described (Ouyang, W., et al. 1998. Immunity 9:745-755).

Intracellular Cytokine Staining and FACS Analysis

Intracellular staining for cytokines was performed as described (Ouyang, W., et al. 1998. Immunity 9:745-755). Primary transgenic or non-transgenic T cells that had been infected with retrovirus for various time periods as indicated were restimulated with PMA (50 ng/ml and ionomycin (1 uM) for 2 hours and 10 ug/ml Brefeldin A added for an additional 2 hours.

Disease Characterization

Hematoxylin and eosin staining of formalin-fixed tissue sections, immunofluorescent studies on OCT-embedded frozen sections, flow cytometry of lymphoid cells, and assays for serum autoantibodies were performed as described[7]. Specific antibodies used in this study included R4-6A2 and XMG1.2 (anti-mouse IFN-γ), BVD4-1D11 and BVD6-24G2 (anti-mouse IL-4), MP5-20F3 and MP5-32C11 (anti-mouse IL-6), JES5-2A5 and SXC-1 (anti-mouse IL-10), MP1-22E9 and MP1-31G6 (anti-mouse GM-CSF), TN3-19.12 (anti-mouse TNF-□), rabbit anti-TNF-□, HM40-3 (anti-mouse CD40), 1D3 (anti-mouse CD19), and PE-R3-34 (rat IgG1, □) (BD Pharmingen, San Diego, Calif.); PE-H106.771 (rat IgG1, □ anti-mouse IgG2a) (Southern Biotechnology Associates, Inc., Birmingham, Ala.); FITC-goat F(ab')$_2$ anti-mouse IgG (Sigma, St. Louis, Mo.). Anti-DNA activity was determined by ELISA using high molecular weight mouse DNA (Sigma), and confirmed by immunofluorescence on *Crithidia lucilliae* kinetoplasts (Antibodies Incorporated, Davis, Calif.).

T Cell Assays

Naive CD4+ T cells were purified from spleen and lymph nodes by negative selection (R&D Systems, Minneapolis, Minn.) and stimulated for 48-72 hours in RPMI/10% with 1 μg/mL anti-murine CD28 (37.51) antibody and 1 μg/mL plate-bound anti-murine CD3 (145-2C11) antibody (BD Pharmingen). Cytokine production was evaluated in culture supernatants by ELISA (BD Pharmingen, San Diego, Calif.). Proliferation was measured by BrdU incorporation (Amersham Pharmacia Biotech, Piscataway, N.J.). Apoptosis was evaluted by exposing the cells for 24 hours to 20 μg/mL soluble anti-mouse CD3 and anti-mouse CD28, 51 μg/mL dexamethasone (Sigma), or 1200J UV irradiation in a Stratalinker (Stratagene, La Jolla, Calif.), followed by evaluation by the CASPACE™ Assay System (Promega Corporation, Madison, Wis.).

Immunoglobulin Assays

For in vitro analyses, purified mature B cells were isolated from spleen and lymph nodes by magnetic CD43 depletion (Miltenyi Biotec, Auburn, Calif.) and stimulated in RPMI/10% with 25 μg/mL LPS (Sigma) supplemented with recombinant murine IL-4 at 10 ng/mL, IFN-γ at 100 ng/mL, human TGF-β1 at 1 ng/mL (PeproTech, Rocky Hill, N.J.), or murine IFN-γ at 100U/mL (R&D Systems, Minneapolis, Minn.). For retroviral infection studies, purified CD43-depleted mature B cells were stimulated by 25 μg/mL LPS for 24 hours, followed by infection by a T-bet-GFP or control-GFP retrovirus[2]. Quantitation of serum immunoglobulin isotypes in serum or culture supernatants was performed as previously described. Germline and postswitch transcripts were determined by RT-PCR as described previously.

Example 1

Cloning of a Novel Transcription Factor, T-bet

Since the Th1-specific region of the IL-2 promoter had been well localized (Brombacher, F., et al. 1994. Int. Immunol. 6:189-197.; Rooney, J., et al. 1995. Mol. Cell. Biol. 15, 6299-6310; Lederer, J. A., et al. 1994. J. Immunol. 152, 77-86; Durand, D., et al. 1988. Mol. Cell. Biol. 8, 1715-1724; Hoyos, B., et al. 1989. Science 244, 457-450), a yeast one hybrid approach using an IL-2 promoter-reporter and a cDNA library made from the OF6 Th1 clone was chosen to identify Th1 specific transcription factors. To validate this approach, the Th2-specific region of the IL-4 promoter was expressed in yeast and demonstrated to be transactivated by the introduction of c-Maf, but not by several other transcription factors (eg NFAT). C-Maf transactivation did not occur when the c-Maf response element (MARE) was mutated. Thus, the yeast one hybrid approach was utilized.

The EGY48 yeast strain was stably integrated with the IL-2 promoter/histidine construct and transformed with a cDNA library made from an anti-CD3 activated Th1 cell clone, OF6. Of $5.6 \times 10^6$ clones screened, 488 were positive in primary screening. Of the 210 clones tested during the secondary screen, 72 proved to be specific for the IL-2 promoter. To reduce the number of positive clones, we hybridized the yeast clone cDNA with cDNAs that were differentially expressed in Th1 and Th2 cell lines. These Th1-Th2 and Th2-Th1 cDNAs were made using the Clontech PCR select kit, radiolabeled and initially used in a pilot experiment to screen the 16 most strongly positive yeast clones. Of those 16 clones, 8 were positive with the Th1 (PL 17) specific cDNA product probe and not with the Th2 (D10) specific cDNA product probe. Representational difference analysis (RDA; e.g., Lisitsyn. 1993. Science. 259:946; O'Neill and Sinclair. 1997. Nucleic Acids Res. 25:2681; Hubank and Schatz. 1994. Nucleic Acids Research. 22:5640; Welford et al. 1998. Nucleic Acids Research. 26:3059) with Th1-Th2 probe on 16 positive clones with control hybridization of the probe to IL-2, IFN-gamma and IL-4 was performed. The specificity of the Th1 and Th2 subtracted cDNA probes is demonstrated by their detection of IL-2 and IFN-γ versus IL-4 respectively.

Restriction enzyme analyses and sequencing data revealed that all 8 of the clones were related. They fell into three groupings based on differences in the 5' and 3' untranslated regions, each of these categories representing an independent cDNA molecule. Comparing the sequence of these clones with the NCBI GenBank Sequence Database yielded homology with the T-box family of transcription factors. FIG. 1 shown the nucleotide and amino acid sequences of T-bet.

Example 2

T-bet Shares a Region of Homology with the T-box Family Members T-brain and Eomesodermin Brachyury or T is the founding member of a family of transcription factors that share a 200 amino acid DNA-binding domain called the T-box (reviewed in (Smith, J. 1997. Current Opinion in Genetics & Development 7, 474-480; Papaioannou, and Silver. 1998. Bioessay. 20:9; Meisler, M. H. 1997. Mammalian Genome 8, 799-800.). The Brachyury (Greek for 'short tail') mutation was first described in 1927 in heterozygous mutant animals who had a short, slightly kinked tail (Herrann, B. G., 1990. Nature 343, 617-622). There are now eight T-box genes in the mouse not including Brachyury. These include Tbx1-6, T-brain-1 (Tbr-1) and now, T-bet, each with a distinct and usually complex expression pattern. The T-box family of transcription factors is defined by homology of family members in the DNA binding domain. The T-bet DNA binding domain (residues 138-327 of murine T-bet) is most similar to the T-box domains of murine T-brain and Xenopus eomesodermin and thus places T-bet in the Tbr1 subfamily of the T-box gene family. The human homologue of the murine T-bet protein is approximately 88% identical to the mouse T-bet. FIG. 1A was derived using a Lipman-Pearson protein aligmnment (with G penalty set at 4 and gap length penalty set at 12. The similarity index was calculated to be 86.6; the gap number2, the gap length5, and the consensus length 535). T-bet shares a region of homology with the T-box family members T-brain and eomesodenuin. The murine T-bet DNA binding domain is most similar to the T-box domains of murine T-brain and Xenopus eomesodermnin. There is approximately 69% amino acid identity between the three T-box regions. T-bet bears no sequence homology to other T-box family members outside of the T-box domain.

Example 3

Figure 2B:
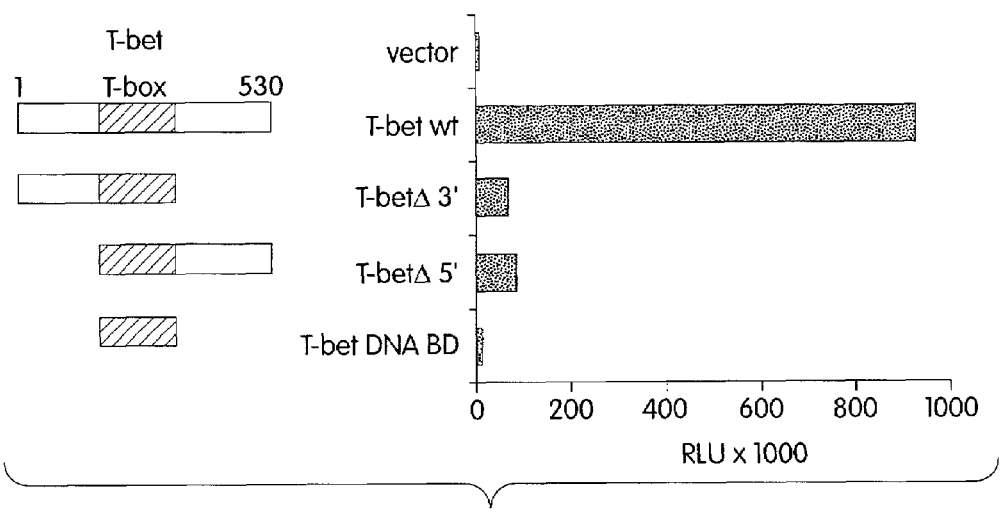

T-bet Binds to and Transactivates Consensus T-box Sites and has Functionally Important Domains that Map to Both 5' and 3' Regions Recombinant T-bet protein binds to consensus T-box sites and to the T-bet site in the IL-2 promoter, and a complex present in nuclear extracts from anti-CD3-stimulated AE7 Th1 cells binds specifically to a consensus (GGGAATTTCA-CACCTAGGTGAAATTCC) SEQ ID NO:5 T-box oligonucleotide probe. To test for activity of T-bet in T cells, the following experiments were performed. Jurkat Th1 cells were cotransfected with T-bet and a luciferase reporter construct. FIG. 2A shows the basal level (open bars) and the PMA (50 ng/ml) plus ionomycin (1 uM) induced (closed bars) promoter activity in Jurkat cells of a luciferase reporter construct containing a minimal thymidine kinase (TK) promoter with or without 4 copies of the consensus T-box site. Each reporter construct was co-transfected with empty pCDNA vector or pCDNA containing the full-length T-bet cDNA as indicated in the figure. The data shown are representative of three independent experiments. FIG. 2B shows Jurkat cells transiently transfected with the luciferase reporter construct containing the minimal TK promoter and multimerized consensus T-box sites and pCDNA vector containing the indicated regions of the T-bet cDNA diagrammed at the left of the bar graph. Luciferase activity was measured 24 hours post-transfection. The experiment was repeated three times with similar results. The basal level (open bars) and the PMA (50 ng/ml) plus ionomycin (1 uM) induced (closed bars) promoter activity obtained demonstrate that T-bet is active in T cells, and that its activity can be further increased upon stimulation.

Example 4

T-bet Expression in T Cells is Restricted to the Th1 Subset and Regulated by Signals Transmitted Via the TeR T-bet was isolated from a Th1 cDNA library and a multiple organ Northern blot analysis revealed T-bet transcripts only in lung, thymus and in peripheral lymphoid organs.

Figure 3A:
FIG. 3A shows that T-bet is preferentially expressed in double negative thymocytes.
Figure 3B:
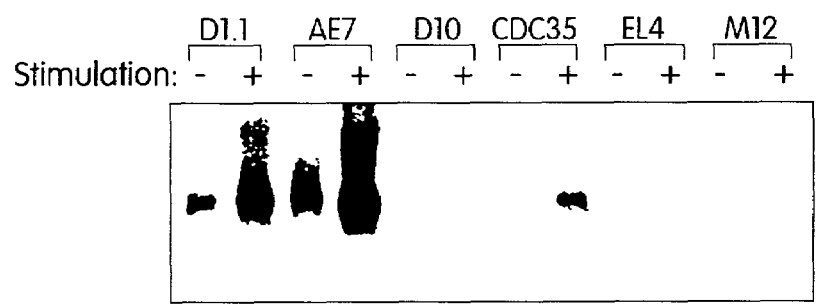
FIG. 3B shows that in a survey of Th clones, T-bet expression is restricted to Th1 cells.

FIG. 3A shows that T-bet is preferentially expressed in double negative (DN) thymocytes, not in double positive (DP) or single positive (SP) cells. Northern blot analysis of total cellular RNA isolated from Th1 cell clones (AE7 and D1.1) or Th2 clones (D10 and CDC35) that were treated with media or with plate-bound anti-CD3 (2C11) for 6 hours revealed T-bet transcripts only in the Th1 clones. Total cellular RNA was isolated from Th1 cell clones (AE7 and D1.1) or Th2 clones (D10 and CDC35) that were treated with media or with plate-bound anti-CD3 (2C11) for 6 hours. Total RNA was also isolated from M12 (B-cell lymphoma and EL4 (T-cell thymoma) treated with media or with PMA (50 ng/ml) and ionomycin (1 uM) for 6 hours. Northern blot analysis was performed with 10 ug of total RNA per lane using standard procedures and probed using the full-length T-bet cDNA.

T-bet is preferentially expressed in Th1 clones. Further, the level of T-bet expression was augmented by signals transmitted via the TcR as evidenced by the induction of T-bet transcripts by anti-CD3. T-bet transcripts were not detected in M12, a B-cell lymphoma, in the Th1 lymphoma Jurkat or in EL4, a Th0-cell thymoma either when these cells were treated with media or with PMA (50 ng/ml) and ionomycin (1 uM) for 6 hours.

Figure 3C:
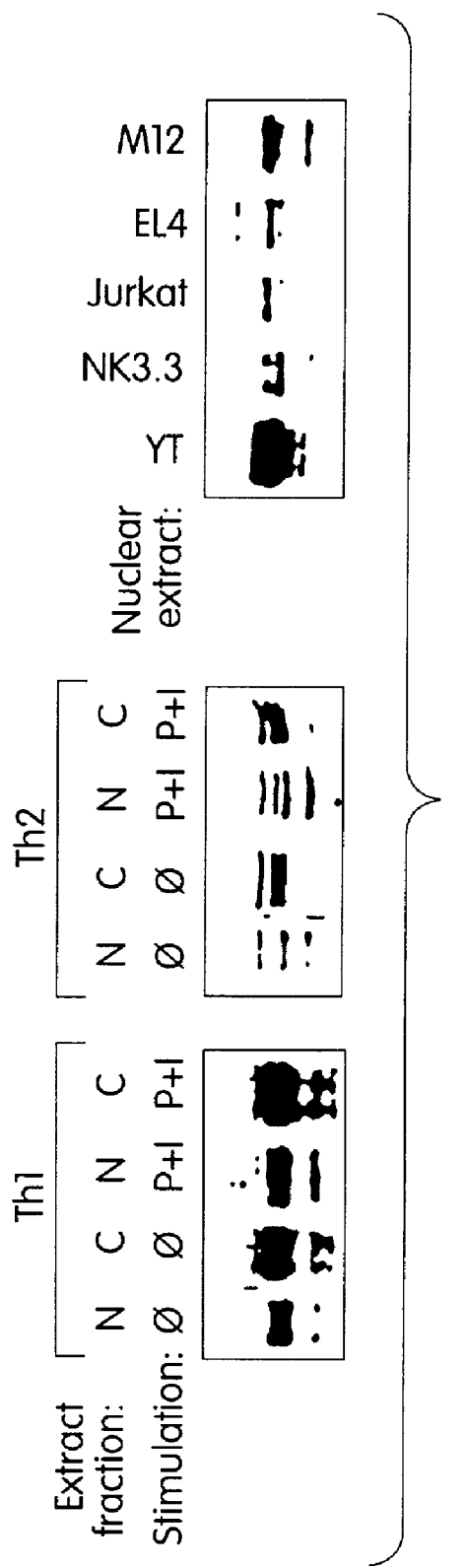
FIG. 3C shows western blot analysis of T-bet.

To determnine protein levels of T-bet in primary Tcells, DO11.10 TcR transgenic splenocytes were cultured under Th1 or Th2 polarizing conditions. At 72 hours the cells were expanded 3-fold in fresh medium with 200 U/ml IL-2. On day 7 after primary stimulation, nuclear and cytosolic extracts were prepared from resting or PMA/ionomycin activated (1 hr) bulk culture DO11.10 Th1 and Th2 cells. Nuclear extracts were also prepared from resting M12, EL4, Jurkat, NK3.3, and YT cells. As shown in FIG. 3C, among the cell lines, T-bet protein was present in YT cells only. FIG. 3C shows T-bet protein is restricted to Th1 cells and NK cells. Western blot analysis was performed on nuclear and cytosolic extracts prepared from resting or PMA/ionomycin activated (1 hr) bulk culture DO11.10 Th1 and Th2 cells as above. Briefly, D011.10 TcR transgenic splenocytes were activated with OVA peptide (323-339) at 3×106 cells/ml in the presence of 10 ng/ml IL-12 and 10 ug/ml anti-IL-4 (11B11) to promote Th1 phenotype development, or 10 ng/ml IL-4 and 10 ug/ml anti-IFN-gamma to promote Th2 phenotype development. At 72 hours the cells were expanded 3-fold in fresh medium with 200 U/ml IL-2. On day 7 after primary stimulation, nuclear and cytosolic extracts were prepared from resting or PMA/ionomycin activate (1 hr) bulk culture D011.10 Th1 and Th2 cells. Nuclear extracts were also prepared from resting M12 cells, EL4, Jurkat, NK3.3, and YT. 30 ug of nuclear and cytosolic extracts were separated by SDS-PAGE (8% gel), transferred to nitrocellulose, and probed with an anti T-bet antisera. In primary T cells, T-bet protein is selectively expressed in T cells driven along a Th1 but not a Th2 pathway, consistent with the Northern blot analysis of T cell clones and primary T cells shown above.

Figure 3D:
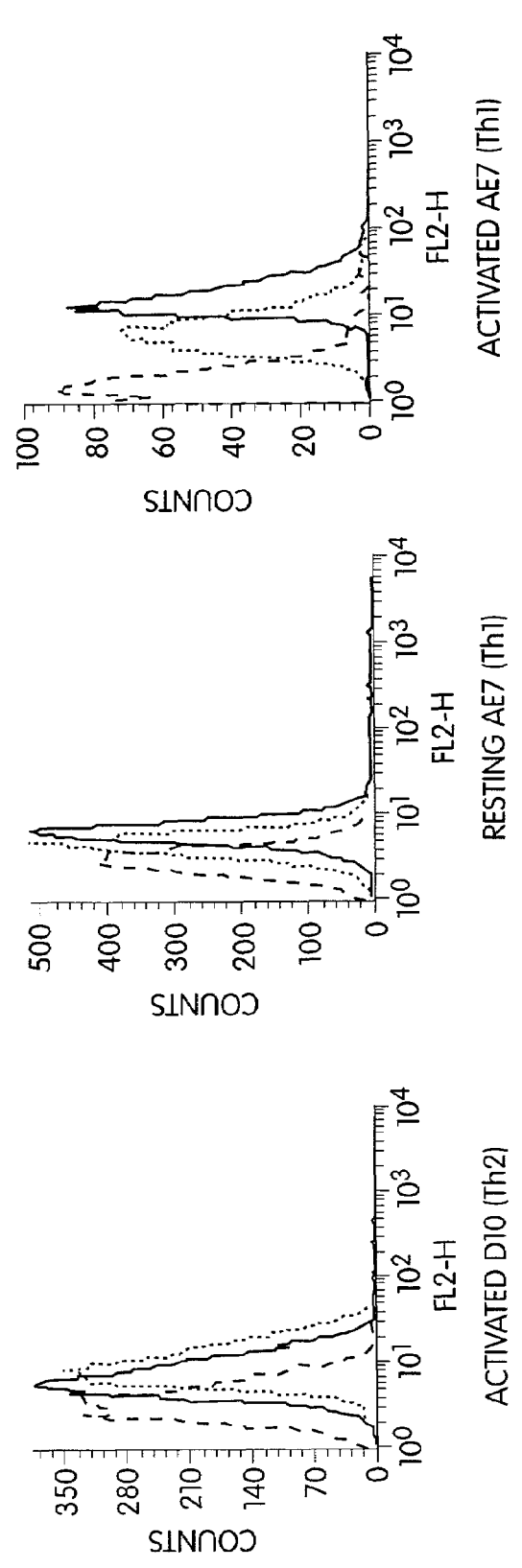
FIG. 3D shows FACS analysis of T-bet expression.

A monoclonal antibody (mAb) specific for T-bet allowed the direct visualization of T-bet protein by FACS analysis. FIG. 3D shows that T-bet can be visualised by FACS in activated AE7 Th1 cells. D10 (Th2) or AE7 (Th1) cells were treated with media or PMA (50 ng/ml) plus ionomycin (1 uM) for 2 hours and 2 uM monensin for an additional 3 hours. Cells were washed with PBS, fixed in 4% paraformaldehyde, permeabilized with 0.5% saponin, and stained with media (dashed line) or an IgG1 isotype control antibody (dotted line) or an affinity-purified anti-T-bet monoclonal antibody ☐3D10 (solid line) followed by goat anti-mouse IgG1-PE staining. Cells were analyzed by flow cytometry on a FACS-Calibur. Mouse monoclonal antibodies were raised against bacterially produced T-bet. T-bet protein was not detectable in D10 cells, was present at low levels in unstimulated AE7 cells and was present at increased levels in stimulated AE7. Taken together, the experiments detailed here demonstrate that in T cells, T-bet is selectively expressed in Th1 cells where its level of expression is regulated by signals stemming from the TcR.

Example 5

T-bet Expression Correlates with IFN-γ Induction in NK and B Cells

The Th1-limited expression of T-bet coupled with its isolation by virtue of binding to a T-box site in the IL-2 promoter suggested that T-bet might activate the transcription of the IL-2 gene. However, it was puzzling that two IL-2-producing cell lines, Jurkat and EL4, did not express T-bet, while the NK cell line YT, which produces IFN-γ but not IL-2, did express T-bet. Further, preliminary experiments did not demonstrate transactivation of the IL-2 gene by T-bet, despite the presence of an excellent T-box site in the IL-2 promoter. Other Th1-specific cytokines include IFN-γ, TNFα and LT. The expression of T-bet correlated well with the expression of IFN-γ. Further, a T-box site was found to be present in the third intron of the human IFN-γ gene. This was especially noteworthy since a Th1-specific DNaseI hypersensitivity site had recently been mapped to this region.

Figure 4A:
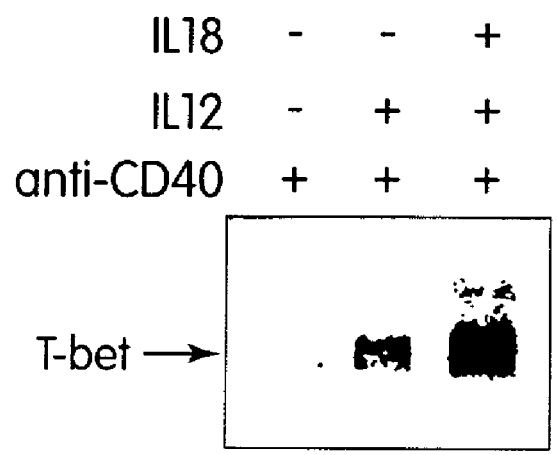
FIGS. 4A and B show that T-bet expression correlates with IFN-γ induction in NK and B cells.
Figure 4B:
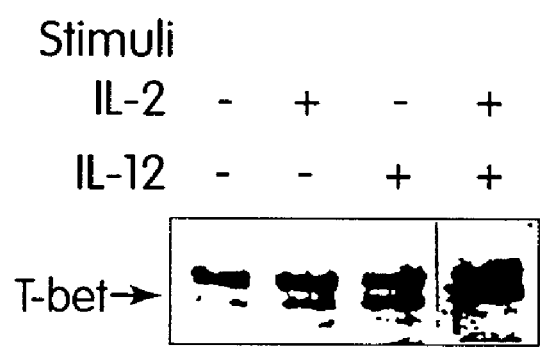

To examine the possibility that T-bet controlled the expression of the IFN-γ gene, the expression of T-bet and the expression of IFN-γ in cells other than Th1 cells was measured. IFN-γ is expressed in natural killer (NK) cells at low levels and is induced to high levels upon treatment with IL-2 and IL-12 (Kornbluth, J., et al. 1982. J. Immunol. 129:2831, Ye et al. 1995. J. Leuko. Biol. 58:225). Therefore, the NK3.3 cell line was treated for 24 h with IL-2, IL-12 and IL-2 plus IL-12, lysates prepared and western blot analysis performed with T-bet rnab as above. FIG. 4b demonstrates coordinate induction of T-bet protein and secretion of IFN-γ in NK3.3 cells. The NK3.3 cell line was treated for 24 h with reagents, IL-2, IL-12 and IL-2 plus IL-12, known to induce IFN-γ in NK cells, lysates prepared and western blot analysis performed with T-bet mAb as above. ELISA was performed on supernatants harvested from the cells.

B cells, which do not produce IFN-γ at baseline, can be driven to produce large amounts of IFN-γ upon treatment with anti-CD40 antibody and a combination of IL-12 and IL-18 (Yoshimoto, T., 1997. Proc. Natl. Acad. Sci. USA 94, 3948-3953). Purified B cells were treated for 72 h with anti-CD40 mAb, rIL-12 and rIL-18, RNA isolated and Northern blot performed using the T-bet cDNA as above. FIG. 4A shows induction of T-bet mRNA in B cells treated with this combination of reagents, and the induction of IFN-γ transcripts in these cells was confirmed. In conclusion, while neither cell type expresses T-bet constitutively, both NK3.3 cells and B cells can be induced to do so under conditions which also result in IFN-γ production. Thus, the pattern of expression of T-bet correlates well with the transcription of the IFN-γ gene.

Example 6

T-bet Transactivates the IFN-γ Gene in Th Cells

Very little is yet known about the regulatory regions of the IFN-γ gene. In particular, the regions of the gene that direct its tissue-specific expression have not been identified in vitro or in vivo. It has been demonstrated that reporter constructs containing 500 bp or 3 kb of upstream sequence are expressed in both Th1 and Th2 cells (Young, H. A., 1994. J. of Immuno. 153, 3603-3610). ATF-2, NF☐B, AP-1 and Stat4 sites in the IFN-γ promoter or introns are thought to be functionally important, but clearly are not responsible for tissue-specific expression (Young, H. A., 1994. J. of Immuno. 153, 3603-3610; Sica, A., 1997. J. Biol. Chem. 272, 30412-30420; Penix, L., 1993. J. Exp. Med. 178, 1483-1496; Penix, L. A., 1996. J. Biol. Chem. 271, 31964-31972). Similarly, although Th1-preferential DNaseI hypersensitive sites have been noted both in the first and third introns, the relevant cis elements located in these introns have not been identified (Young, H. A., et al. 1994. J. of Immnuno. 153, 3603-3610; Agarwal, S. and Rao, A. 1998. Immunity 9, 765-775). Therefore, a reporter construct containing the entire IFN-γ gene was utilized for these studies. The IFN-γ reporter gene used includes 3 kb of upstream sequence, the entire coding sequence with all three introns, and 1.5 kb of downstream (Xu, X., et al. 1996. Science 273, 794-796).

The activity of a luciferase reporter construct containing 9 kb of the IFN-gamma gene in the Jurkat human Th1 lymphoma and the mouse EL4 Th0 tymoma was tested. Each reporter construct (10 ug) was co-transfected with empty pCDNA vector or pCDNA containing the full-length T-bet cDNA, c-Maf, NFATP or p65 (10 ug). The constructs also include the −400 to −40 IL-2 and IL-4 promoter luciferase reporters.

Figure 5:
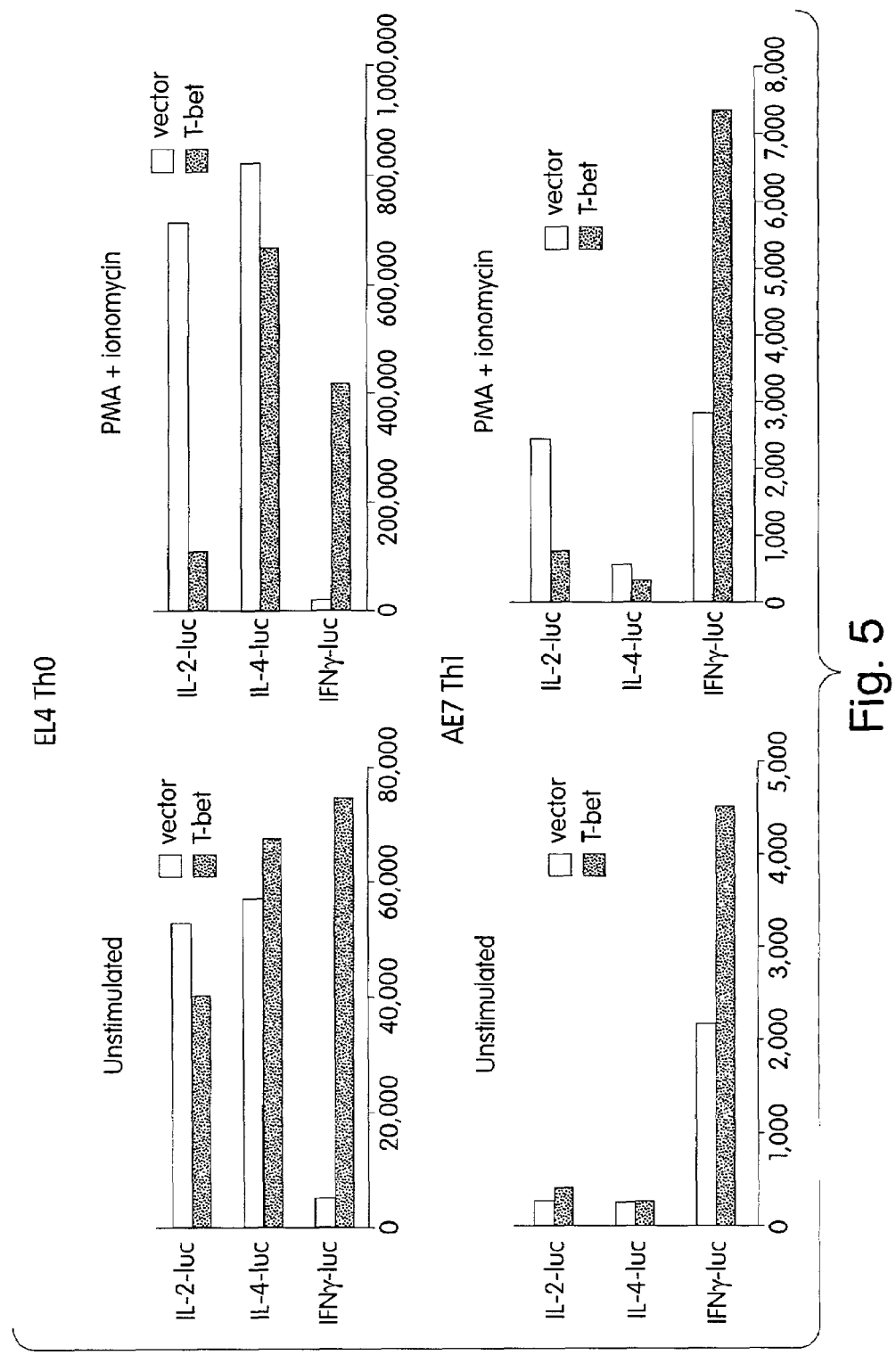
FIG. 5 shows that T-bet transactivates the IFN-γ gene in Th cells.

The Th0 mouse T cell thymoma EL4, which produces IL-2 and IL-4 but not IFN-γ was transfected with a T-bet cDNA expression plasmid and the IFN-γ-luciferase reporter (FIG. 5). Introduction of the T-bet expression plasmid resulted in (approximately 20-30 fold) transactivation of the IFN-γ gene compared to empty vector alone. This was in contrast to the absence of transactivation by two other factors, the Th2-specific transcription factor c-Maf and the Th non-selective transcription factor NFAT. Interestingly, although the NF EIB family member, p6 5, did not transactivate the IFN-γ reporter on its own, cotransfection of T-bet and p65 resulted in a synergistic activation.

Examination of the IL-2 promoter was also made using a region of the promoter known to be Th1-specific (Lederer, J. A., et al. 1994. J. Immunol. 152, 77-86). T-bet repressed the activity of the IL-2 promoter approximately 10 fold. This was especially apparent upon activation of the promoter by PMA and ionomycin. As before, substantial transactivation of the IFN-γ gene was noted. T-bet activity was specific for the IL-2 and IFN-γ genes since no effect on transactivation of an IL-4 promoter (FIG. 5) or a TNF-☐ promoter was present. These data demonstrate that T-bet specifically activates the transcription of the IFN-γ gene, and represses the transcription of the IL-2 gene.

To examine endogenous gene expression, EL4 cells were transiently transfected with T-bet or empty vector, and IFN-γ production measured by ELISA 48 hours after stimulation with PMA/ionomycin (FIG. 5). Consistent with the transactivation data shown above, ectopic expression of T-bet in EL4 cells led to measurable IFN-γ production while transfection with vector control did not result in detectable IFN-γ.

Example 7

Retroviral Gene Mediated Rransfer of T-bet into Primary Th Cells Results in Increased IFN-γ Production The experiments described above argue strongly for a critical role of T-bet in controlling the transcription of the IFN-γ gene.

Figure 6:
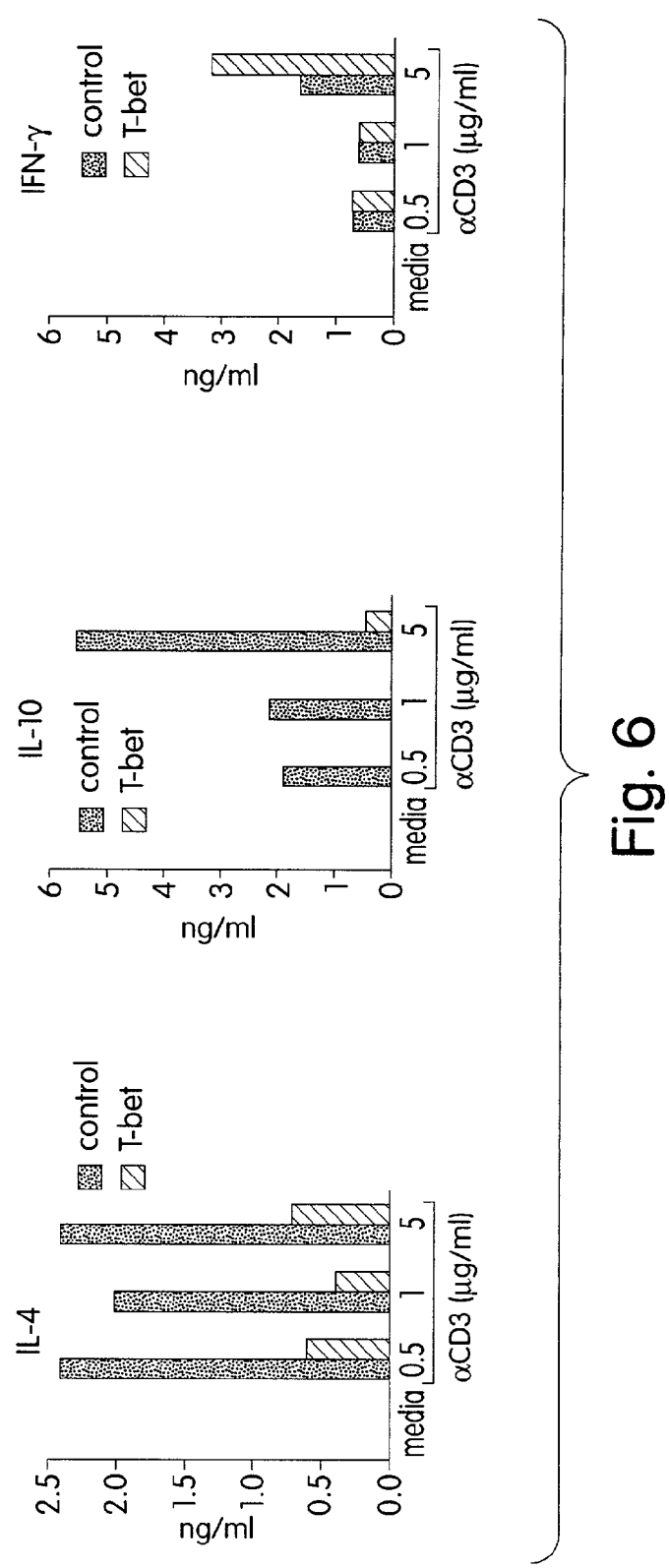
FIG. 6 shows that retroviral gene transduction of T-bet reduces increases IFN-gamma production and represses IL-2 production.

A bovine collagen-specific Th0 hybrid was transduced with retroviral constructs containing T-bet GFP or GFP only under the control of the TcR inducible IL-2 promoter. Transduced populations were FACS sorted on GFP twice, rested and then stimulated with anti-CD3 and supernatants collected at 60 hours to measure cytokine production by ELISA. (FIG. 6). Control retroviral vectors which had not affect included anti-sense T-bet.

To further test whether T-bet is responsible for the tissue-specific expression of IFN-γ, retroviral gene mediated transfer of T-bet into primary T cells, both non-transgenic and TcR transgenic, was performed. Two different bicistronic retroviruses expressing both T-bet and GFP were used. The first expresses T-bet under the control of an IL-2 inducible promoter, and the second expresses T-bet under control of an MSCV LTR. Similar results were obtained with both constructs.

BALB/c CD4 T cells were infected after 36 hours of primary activation by anti-CD3 plus anti-CD28, harvested on day 7 and intracellular IFN-gamma and IL-2 staining performed 5 hours after stimulation with PMA and ionomycin as described in Experimental Procedures. Data are shown as two-color plots showing GFP expression (FL1) versus intracellular cytokine (FL2) of events gated on expression of CD4. Primary T cells from MBP TcR transgenic mice were stimulated using MBP (Ac1-11) at 6 uM and infection performed on day 1 with IL-2/GFP and IL-2/T-bet/GFP. On day 7, cells were sorted for GFP expression, rested for 1 day and then intracellular cytokine analysis performed after a 5 hour stimulation with PMA and ionomycin.

Naive MBP-transgenic or non-transgenic BALB/c CD4 T cells were activated with MBP 1-11 and anti-CD3 under non-polarizing conditions and were infected with retrovirus on day 1 after primary activation as described (Ouyang, W., et al. 1998. Immunity 9:745-755). Cells were cultured for 7 days and then GFP expression measured to determine percentage of cells infected. GFP positive cells were sorted and cytokine production measured by intracellular staining after an additional 4 hours stimulation with PMA plus ionomycin.

Figure 7:
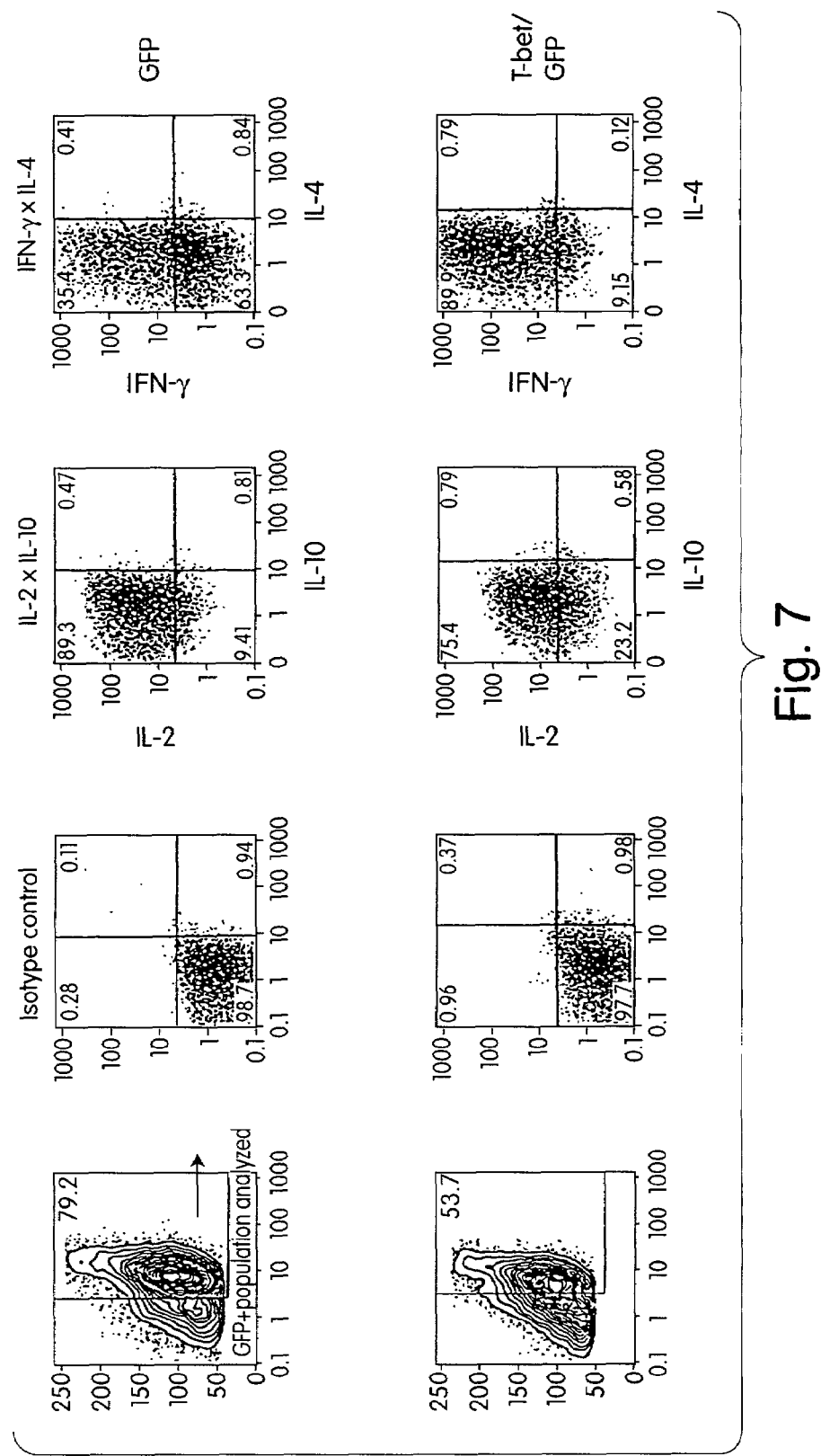
FIG. 7 shows that T-bet activates IFN-γ and represses IL-2 production in primary T cells.

Transduction of both MBP-TcR transgenic and non-transgenic T cells with T-bet resulted both in an impressive increase in the number of cells producing IFN-γ and in the amount of IFN-γ produced per cell as compared to cells transduced with GFP alone. (FIG. 7).

Naive Thp cells, early after stimulation, produce large amounts of IL-2, which is then gradually replaced in polarized Th cells by the effector cytokines IFN-γ and IL-4. Polarized Th1 cells do continue to produce IL-2 but at amounts considerably less than naïve Thp. Polarized Th2 cells shut off the production of IL-2. T-bet transduced Th cells produced somewhat less IL-2 than GFP/RV control transduced cells, consistent with the repression of IL-2 promoter transactivation by T-bet that we observed in EL4 cells. The repression of IL-2 by T-bet is consistent with a function for T-bet in driving lineage commitment from a naive precursor cell into a fully differentiated effector cell.

Example 8

T-bet Activates IFN-γ and Represses IL-4 Production in Developing Th2 Cells

Figure 8A:
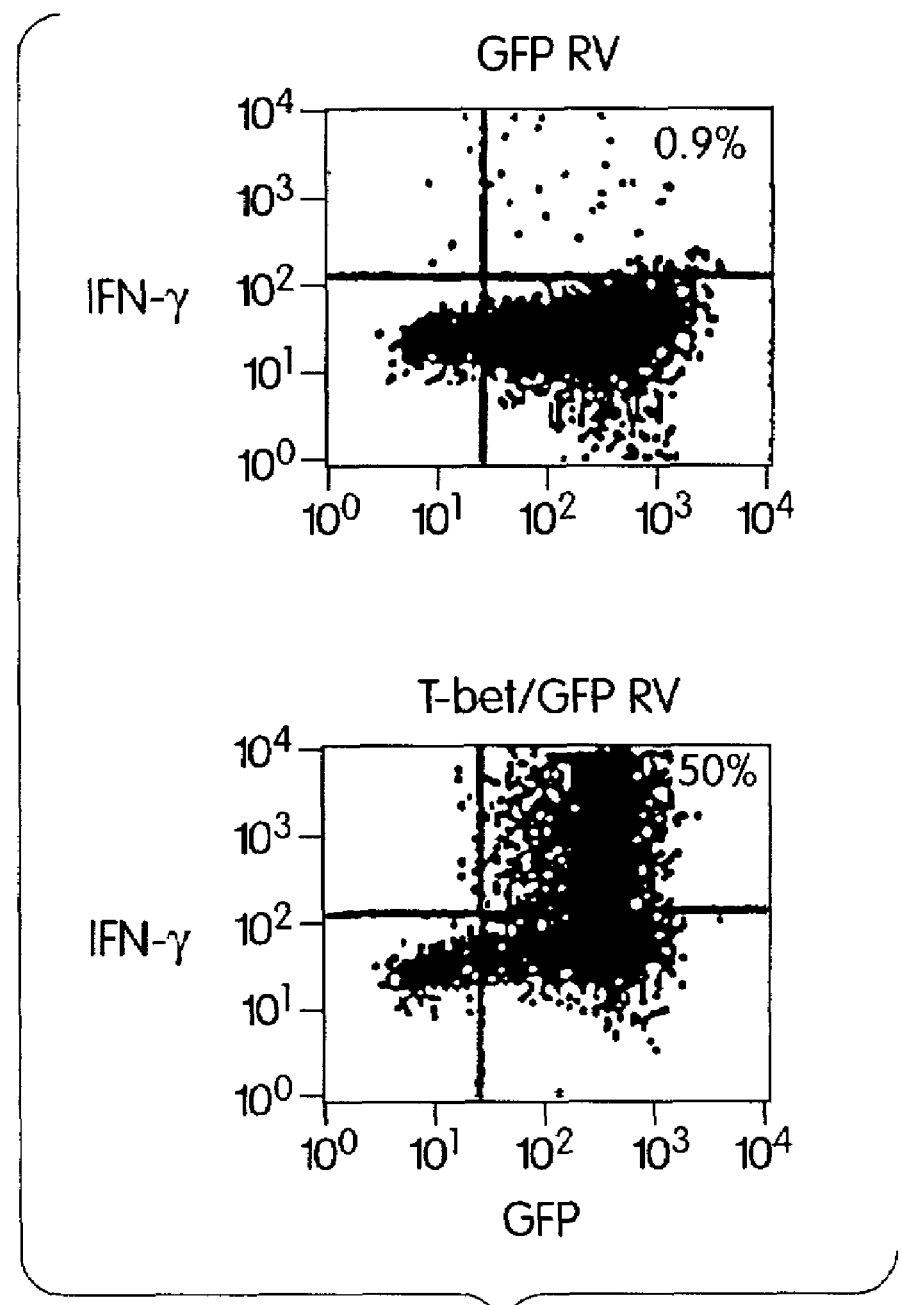
FIG. 8 shows that T-bet induces IFN-gamma and inhibits IL-4 production in developing Th2 cells.
Figure 8B:
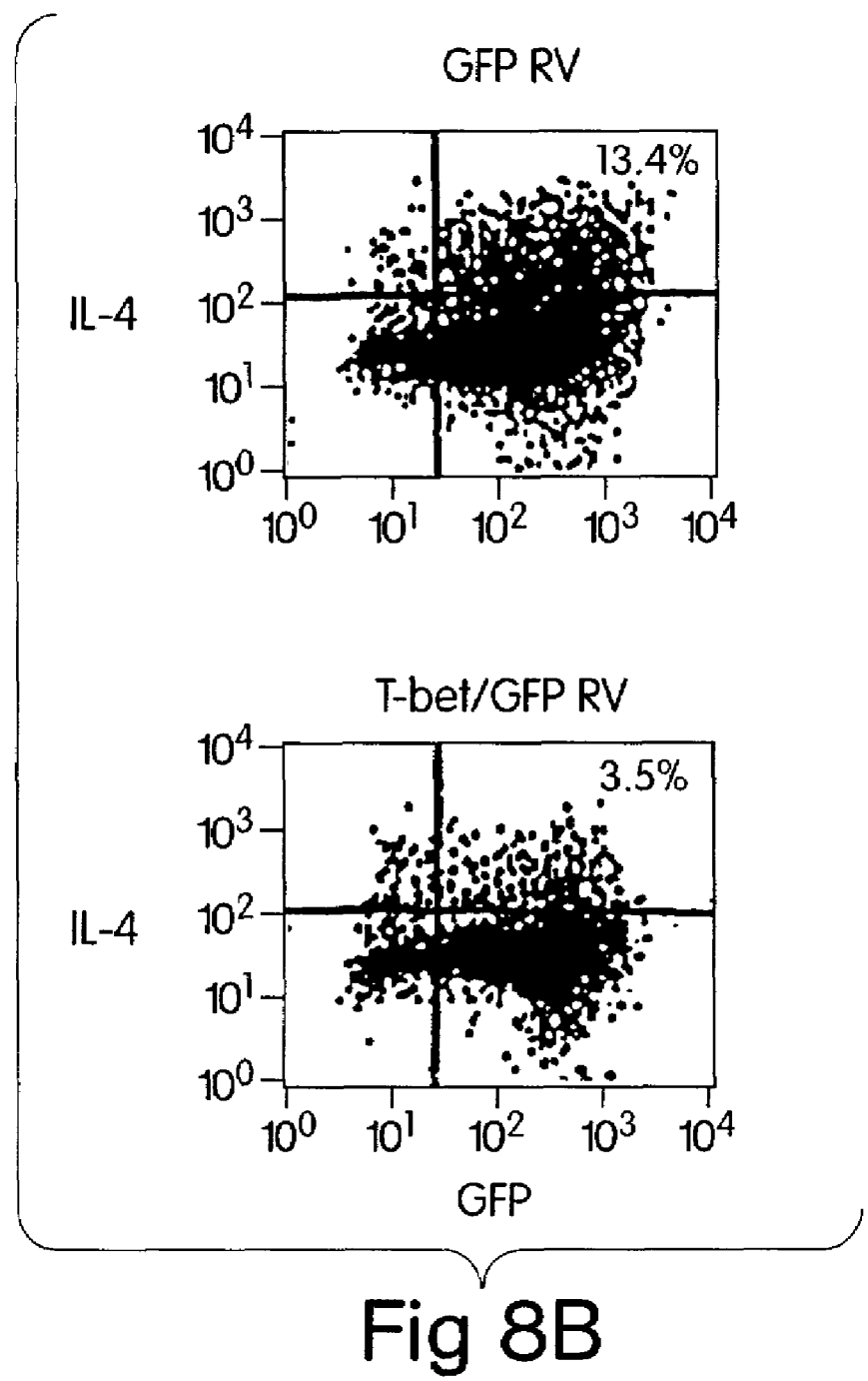
Figure 9A:
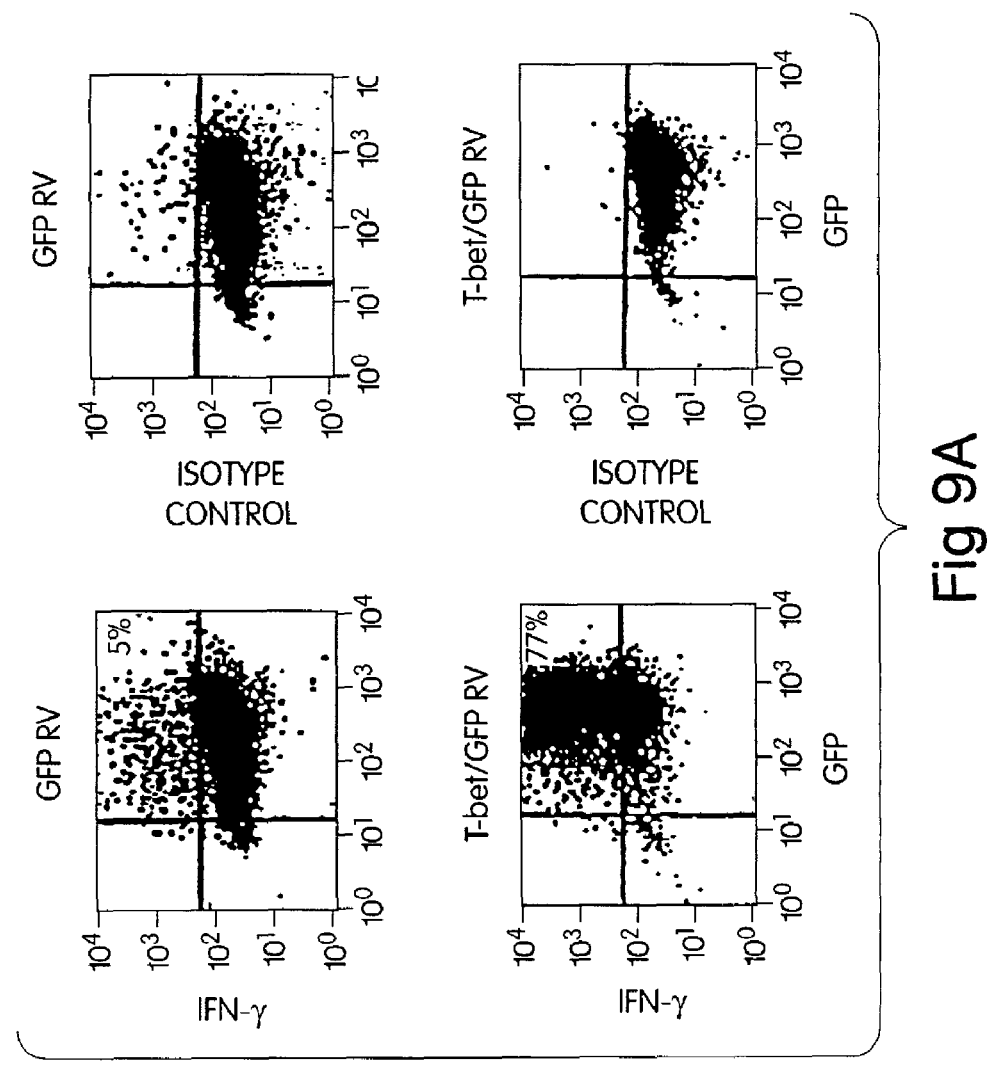
FIG. 9 shows that T-bet redirects polarized Th2 cells into the Th1 pathway. Th-skewing was carried out as above and retroviral infections were performed on day 9 of culture.
Figure 9B:
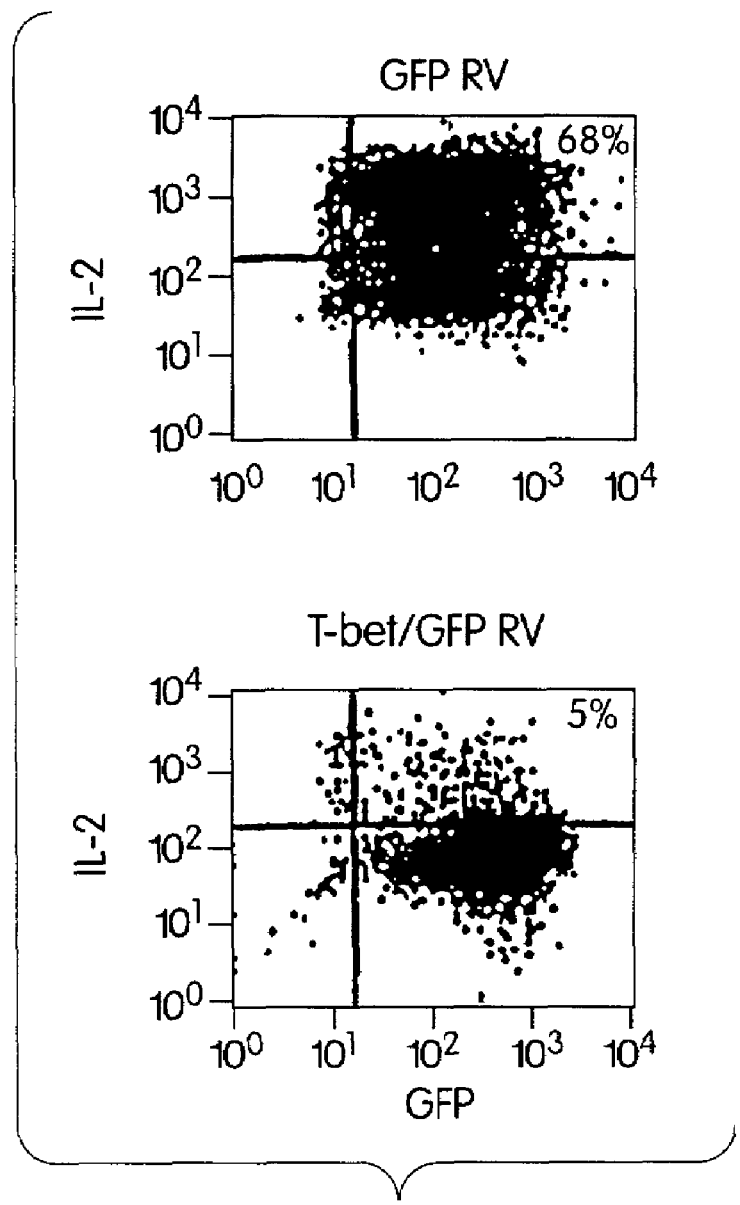
Figure 9C:
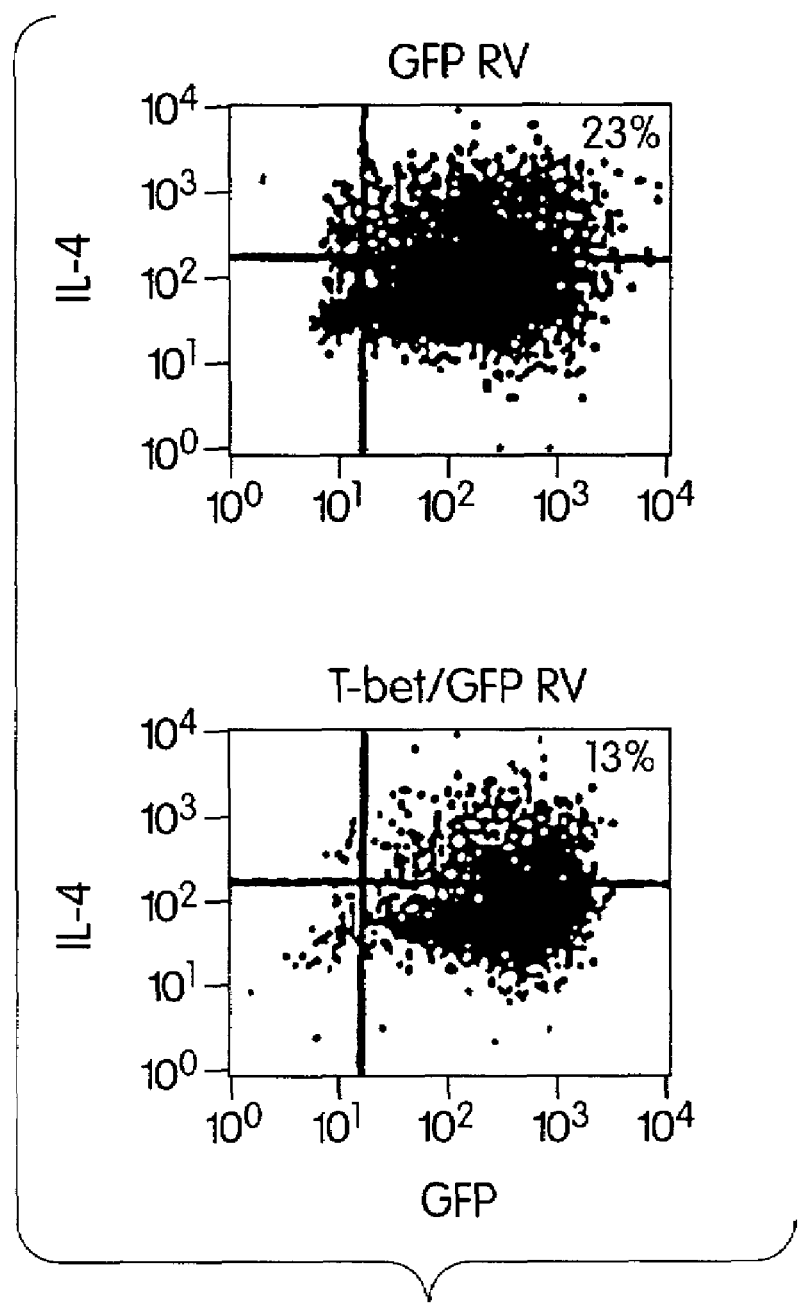
Figure 9D:
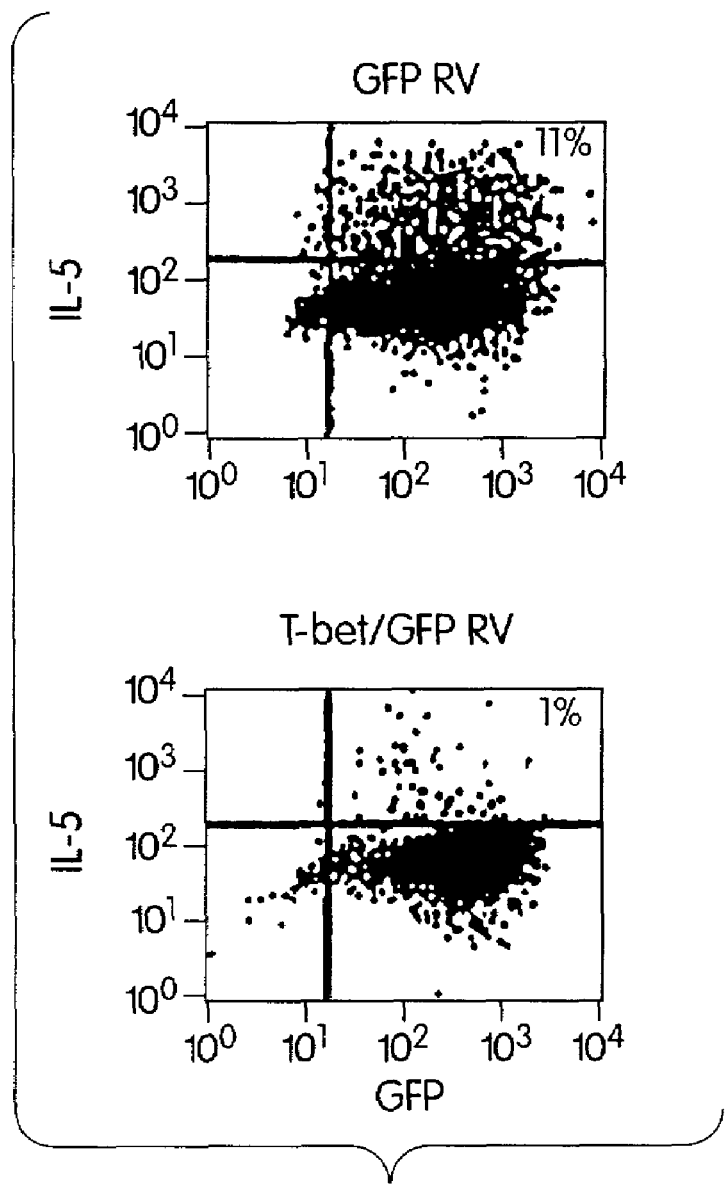

The experiments above demonstrate that T-bet can direct unskewed Th cells into the Th1 pathway. The T-bet could force Th cells to direct their genetic program along a Th1 pathway even in the presence of stimuli that would ordinarily drive them into the Th2 pathway was tested. In the experiments in FIG. 8, BALB/c CD4+ T cells were activated with anti-CD3 and anti-CD28 in the presence of rIL-4 and antibodies to IFN-γ and IL-12, retroviral infection performed at 36 hours, cells expanded with IL-2, GFP positive cells sorted on day 7 and cytokine production measured by intracellular staining after an additional 4 hours stimulation with PMA plus ionomycin. Transduction with GFP-RV alone resulted in a population that contained 13.4% IL-4-producing cells and 0.9% IFN-γ producers (FIG. 8). As expected, the Thp cells are not yet fully polarized at this time. Introduction of T-bet/GFP/RV produced a substantial shift of Thp into the Th1 pathway as evidenced by the large number of cells (50%) producing IFN-γ and the reduced number of cells producing IL-4 (3.5%), even under conditions (rIL-4 and anti-IL-12) that inhibit Th1 differentiation. Thus, T-bet can overcome the Th2-promoting signals delivered by cytokines to drive developing Th cells into the Th1 pathway.

Example 9

T-bet Redirects Polarized Th2 Cells into the Th1 Pathway

It has been demostrated that reversibility of Th1 and Th2 populations is lost after long-term stimulation under polarizing conditions. Reversibility is largely abrogated after one week and is completely lost after 3 weeks (Murphy, E., et al. 1996. J. Exp. Med. 183, 901-913). To determine whether T-bet could redirect the commitment of a pure population of already polarized Th2 cell, CD4+ T cells were cultured as above and retroviral gene transduction performed at day 9 of culture. In Th cells cultured for 9 days under Th2 polarizing conditions, control GFP/RV-transduced cells are virtually all IL-4 and IL-5 producers (23% and 11%) with barley dectable IFN-γ producer cells (6%) (FIG. 9). Thus, as expected, almost complete polarization had occurrred. Remarkably, introduction of T-bet into these fully polarized Th2 cells redirected or converted them into polarized Th1 cells as evidenced both by the induction of IFN-γ expression and the loss of IL-4 and IL-5 expression. This conversiopn occurred in the presence of exogenous IL-4. Fully 77% of T-bet-transduced Th2 cell now produced IFN-γ while the percentage of cells producing IL-4 and IL-5 has been reduced to 13% and 1% respectively. These T-bet-transduced cells are therefore not Th0 cells that produce both IFN-γ and IL-4. Therefore, T-bet has not simply induced IFN-γ expression in Th2 cells but has actually reprogrammed Th2 cells into the opposing Th1 subset.

Example 10

T-bet also Redirects Polarized Tc2 [Cells] into the Th1 Pathway

Figure 10B:
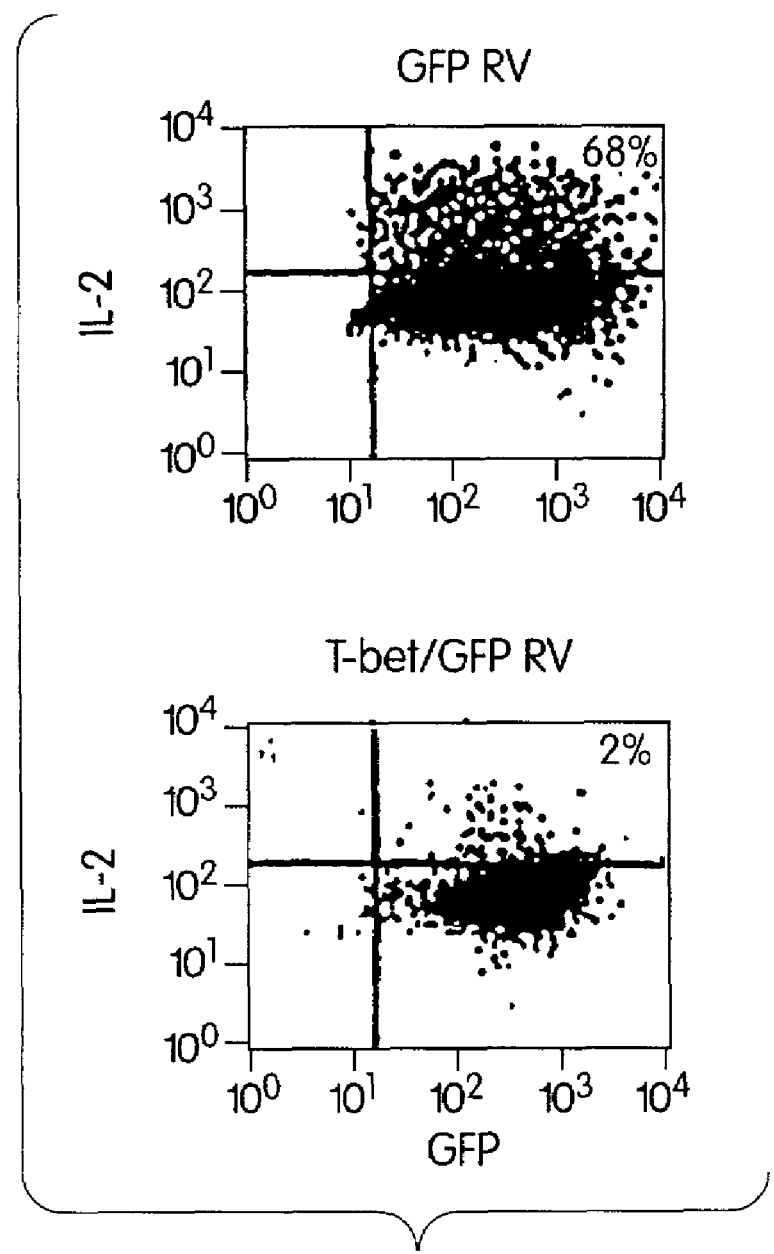
FIG. 10 shows that T-bet redirects polarized Tc2 cells into the Tc1 pathway. CD8+ T cells were purified by MoFlo and cultured under Th2 skewing conditions as above and retroviral transductions performed on day 8 of culture.
Figure 10C:
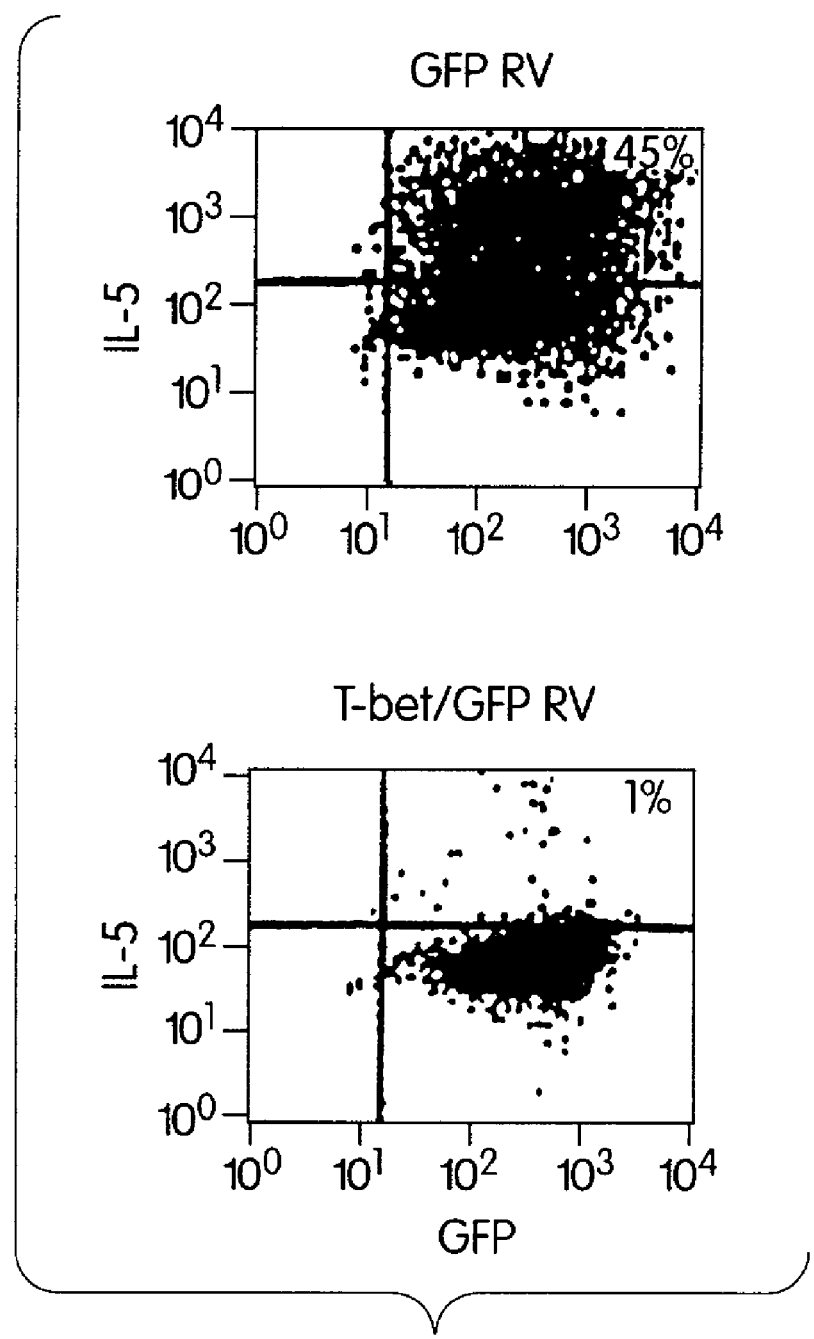
Figure 10D:
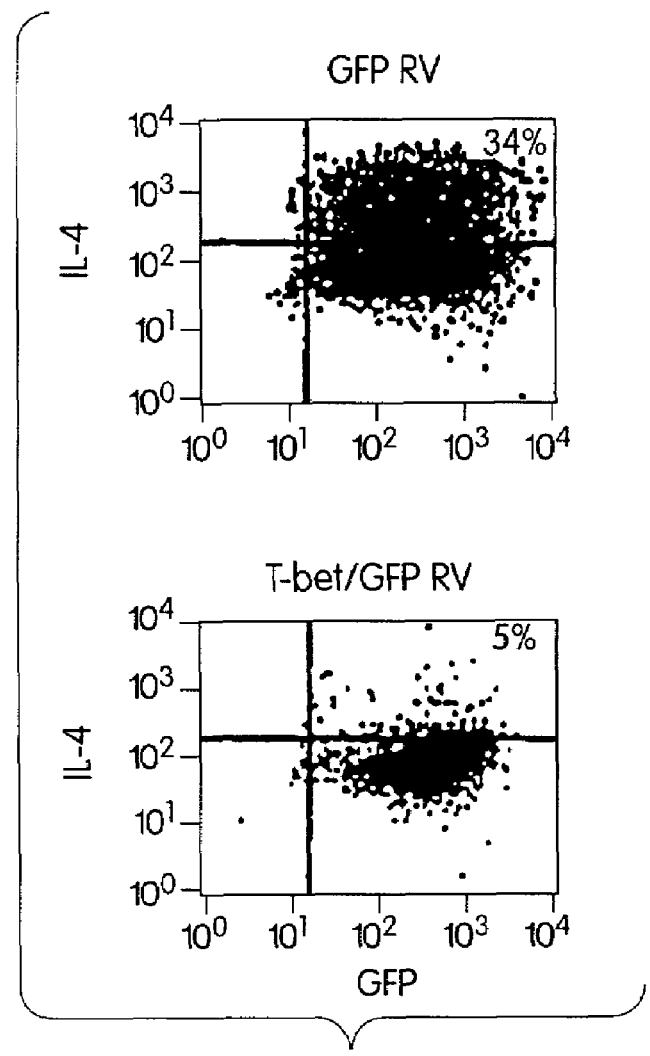

Although most attention has focused on the CD4+ T lymphocyte, it is apparent that cytotoxic CD8+ T cells also may also be divided into IFN-γ-producing (Tc1) and IL-4-producing (Tc2) subsets. The ability of T-bet to redirect fully polarized Tc2 cells into a Tc1 pathway was tested. Purified CD8+ T cells were therefore differentiated in culture under Tc2 polarizing conditions for 9 days to accomplish full differentiation. FIG. 10 demonstrates that T-bet transduced Tc2 cells, similar to T-bet transduced CD4 Th2 cells have been reprogrammed to produce IFN-γ (85% versus 15%) and to repress the production of IL-4 and IL-5 (3% versus 34% and 1% versus 45% respectively). Thus, T-bet can convert fully differentiated CD8+ Tc2 cells to Tc1 cells.

Example 11

T-Bet is Tyrosine Phosphorylated

Figure 11:
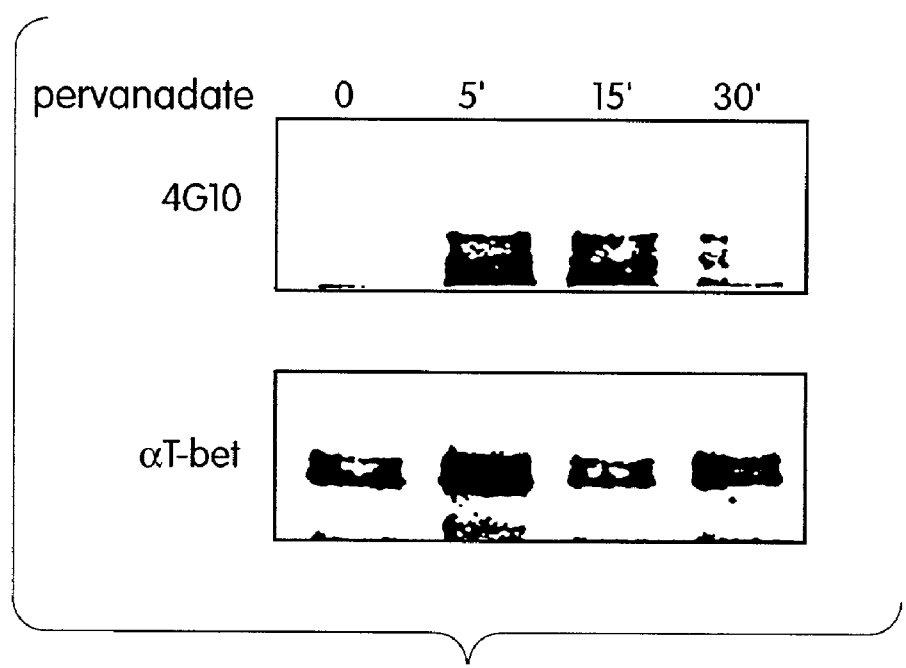
FIG. 11 shows that T-bet is tyrosine phosphorylated.

To determine whether T-bet is a tyrosine phosphorylated protein, whole cell lysates from AE7 Th1 cells were prepared after incubation for 0, 5, 10, 30 minutes with pervanadate. Lysates were immunoprecipitated with anti-T-bet antiserum, separated by SDS-PAGE (8% gel), transferred to nitrocellulose, and probed with an anti-phosphotyrosine mAB 4G10. Following exposure, blots were stripped and reprobed with anti-T-bet antisera. As shown in FIG. 11, T-bet is clearly a tyrosine phosphorylated protein in T cells.

Example 12

Creation of a Dominant Negative T-bet Molecule

Figure 12:
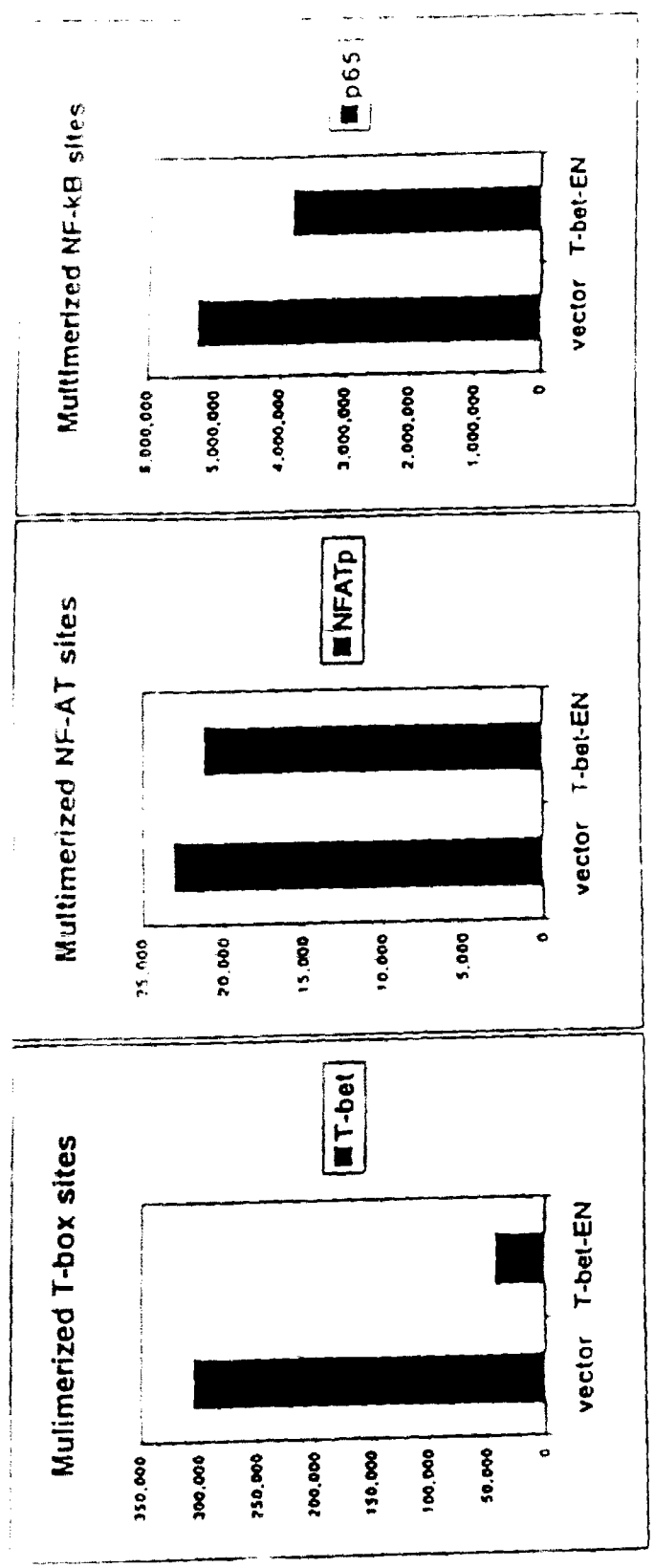
FIG. 12 shows the activity of a T-bet dominant negative mutant.

Chimeric cDNA molecules were made with the T-bet DNA binding domain (residues 138-327) and the repressor domain of the Drosphilia protein engrailed. The engrailed protein is a powerful, active repressor of transcription (Taylor, D., 1996. *Genes Dev.* 10, 2732; Li, J., Thurm, H., et al. 1997. *Proc. Natl. Acad. Sci. USA* 94, 10885). The T-bet-engrailed construct in vitro using a multimerized T-box consensus site/TK minimal promoter luciferase reporter construct. As shown in FIG. 12, T-bet/engrailed specifically and significantly represses the ability of wt T-bet to transactivate a T-box reporter construct at a 5:1 ratio, and does not repress transactivation of an NFAT or NFkB reporter by NFATp and p65 expression constructs respectively.

Example 13

Mutations of the T Box of the IL-2 Promoter Decrease IL-2 Promoter Activity

Figure 13:
FIG. 13 shows that mutations of the T-box element of the IL-2 promoter reduce IL-2 promoter activity.

Recently, the crystal structure of the T-box region of the Brachyury gene bound to DNA was solved and the amino acid moieties essential for specific DNA contacts or for minor contacts deduced. Examination of the human and murine IL-2 proximal promoter shows that the critical nucleotides for binding a T-box family member are present. Specifically −240 to −220 bp of the murine IL-2 promoter has strong similarity to the consensus T-box site. The consensus T-box site is AATTTCACACCTAGGTGTGAAATT. (SEQ ID NO:6). The human IL-2 promoter comprises: gAgcTatCAC-CTAaGTGTGggcTa (SEQ ID NO:7). The murine IL-2 promoter comprises: AAacTgcCACCTAaGTGTGggcTa (SEQ ID NO:8). The mutated T-box mIL-2 promoter comprises: AAacTgctgtCTAaacaTGggcTa (SEQ ID NO:9). (DNA contacts are in bold, minor contacts are underlined). Transversional nucleotide substitutions shown by crystal structure to be essential for DNA-protein interactions were made within this putative T-box site in the context of the murine −440 to −40 bp IL-2 promoter. The basal level (open bars) and the PMA (50 ng/ml) plus ionomycin (1 uM) induced (closed bars) promoter activity in Jurkat cells (left) or AE7 Th1 clone (right) of IL-2 luciferase reporter constructs is shown (FIG. 13).

The role of T-bet is to drive differentiation of Th cells as evidenced by its ability to simultaneously induce the IFNγ gene and repress the IL-2 gene. The antigen-inexperienced Thp cell produces only IL-2. Upon stimulation, IL-2 production declines and is replaced by production of the Th mature effector cytokines. In particular, Th2 cells cease to make IL-2 as they acquire the ability to make IL-4, and the function of T-bet in simultaneously inducing IFN-γ and repressing IL-2 was especially obvious in Th2 cells. The ability of T-bet to simultaneously transactivate the IFN-γ promoter and repress the IL-2 promoter is therefore consistent with a role for T-bet in propelling differentiation of the naïve Thp. T-bet has been shown to transactivate a construct containing only 3 kb of upstream promoter sequence, consistent with the presence of two T-box sites at positions −2300 to −2291 and −1957 to −1948. However, since this region of the promoter is not Th1-specific, it is likely that the T-box site in the third intron is also important and there may well be additional T-box sites elsewhere in the gene.

The T-box domain has recently been co-crystallized with DNA and demonstrates a novel sequence-specific DNA recognition architecture in which the protein contacts DNA in both the major and minor grooves (Müller, C. W. and Herrmann, B. G. 1997. Nature 389, 884-888). The consensus T box binding site as defined by target site selection in vitro is a palindrome 5'-GGGAATTTCACACCTAGGTGTGAAAT-TCCC-3'. (SEQ ID NO:5). Inspection of the IL-2 promoter reveals an excellent T-box site at −240 to −220 just 5' of the NF☐B site to which recombinant T-bet protein binds. The binding of T-bet to the IL-2 promoter explains its isolation in the yeast one hybrid screen where the readout depended simply on binding of T-bet to the T box site in the IL-2 promoter to drive an artificial reporter. Despite the clear repression of IL-2 promoter activity by T-bet, a decrease in IL-2 promoter activity upon mutation of the T-box site has been observed. However, that T-bet can still repress the transactivation of an IL-2 promoter construct in which that T-box site has been mutated. This suggests either the presence of another T-box site in the IL-2 promoter, or interference with another positively acting factor that binds close by. A good candidate for this factor is an activity described by Rothenberg and colleagues that binds to a site TGGGCC just adjacent to the T-box site (Chen, D. and Rothenberg, E. V. 1994. J. Exp. Med. 179, 931-942).

In addition, T-bet represses the Th2 program in Thp and Th2 cells. This is unlikely to be the direct result of an imbalance between IFN-γ and IL-4 in favor of the former. The effect of T-bet in repressing the Th2 program while simultaneously enhancing the Th1 program is reminiscent of GATA-3 and c-Maf, both of which indirectly repress IFN-γ expression, the former through influencing expression of the IL-12 receptor ☐2 chain (Ho, I-C., et al. 1998. J. Exp. Med. 188:1859-1866.; Ouyang, et al. 1998. Inhibition of Th1 developmental mediated by GATA-3 through an IL-4 independent mechanism. Immunity 9:745-755). However, unlike GATA-3 and c-Maf, T-bet can actually convert fully polarized effector Th cells into the opposing pathway.

Example 14

T-bet is Required for Interferon-γ Production and Th1 Lineage Commitment

A. Generation of T-bet Deficient Mice

To definitively address the role of T-bet in IFN-γ production and Th1 lineage commitment, T-bet deficient mice were generated. The T-bet gene was disrupted by homologous recombination by replacing the first exon, 500 bp of upstream sequence, 1 kb of intronic sequence with the neomycin resistance gene. Germline chimeric animals generated from the targeted TC1 embryonic stem cell clone produced heterozygous mice which were then intercrossed to obtain mice homozygous for the T-bet mutation (T-bet$^{-/-}$). T-bet deficient mice were born at the expected Mendelian ratios and were phenotypically normal and fertile. To confirm that the T-bet mutation inactivated the T-bet gene, total RNA or total protein lysates were isolated from resting or PMA/ionomycin activated CD4$^+$ T cells from wild type littermate controls, and heterozygous or homozygous mutant mice. T-bet expression was not detected by Northern or Western blot analysis in T-bet$^{-/-}$ CD4$^+$ T cells and was present at a reduced level on T-bet$^{+/-}$ heterozygotes.

Flow cytometric analysis of thymocytes, splenocytes and lymph node cells from littermate controls and T-bet$^{-/-}$ mice revealed no abnormalities in expression of CD3, CD4, CD8, B220 nor in the composition of lymphocyte populations within each peripheral lymphoid organ. Thus, T-bet is not required for normal thymocyte maturation or mature T/B cell homing to peripheral organs.

B. T-bet Controls IFN-γ Production and Th1 Lineage Commitment

The cytokine production profiles from CD4+ T cells from T-bet deficient mice were examined. CD4+ T cells were purified from the lymph nodes of T-bet$^{-/-}$, T-bet$^{+/-}$ and T-bet$^{+/+}$ mice to yield apopulation of 95% pure naïve CD4+/Mel14+ T cells. A striking decrease in IFN-γ production by T-bet$^{-/-}$ CD4+ T cells was observed as measured by ELISA 72 hrs after anti-CD3/CD28 stimulation as compared to wt littermate control T-bet$^{+/+}$ CD4+ T cells. A corresponding increase in IL-4 production was observed in T-bet$^{-/-}$ CD4+ T cells. These results demonstrate that T-bet deficient cells produce Th2 type cytokines during a primary stimulation under neutral conditions (in which no cytokines or anti-cytokine abs were added).

To determine if this was an immediate effect on cytokine production or an effect on T helper cell differentiation, CD4+ T cells were purified from the lymph nodes of T-bet$^{-/-}$, T-bet$^{+/-}$ and T-bet$^{+/+}$ mice and stimulated through the TCR under neutral conditions or under Th1 or Th2 inducing conditions to generate effector T helper cells. Upon restimulation with anti-CD3, cytokine production was measured by ELISA. T-bet$^{-/-}$ CD4+ T cells produced dramatically less IFN-γ than the control T-bet$^{+/+}$ CD4+ T cells with a concomitant increase in IL-4 and IL-5 production. This effect was seen even when the cells were stimulated in the presence of Th1 inducing conditions. Upon restimulation, these cells produced very low levels of IFN-γ and could not suppress production of IL-4 and IL-5. Thus, even under Th1 inducing conditions, T-bet$^{-/-}$ CD4+ T cells default toward the Th2 lineage. These results were confirmed by ICC, an assay that allows for the examination of each IFN-γ producing cell, which showed a striking decrease in the number of IFN-γ producing cells in the absence of T-bet. We conclude that T-bet controls not only immediate cytokine production but also has a profound effect on T helper effector function.

Interestingly, heterozygous T-bet$^{+/-}$ CD4+ T cells displayed an intermediate phenotype of cytokine production. It is possible that the absence of one allele of T-bet, with a corresponding decrease in T-bet protein, resulted in all CD4 T cells producing half as much IFN-γ as wild-type cells. Alternatively, there might be an exquisite sensitivity to threshhold levels of T-bet with half as many cells producing wildtype levels of IFN-γ. To distinguish between these possibilities, ICC assays were performed. Cells were stimulated under Th1 inducing conditions for 7 days, then restimulated with PMA/ionomycin and analyzed for intracellular IFN-γ. This revealed that 85% of wildtype Th1 cells were IFN-γ producers while a striking decrease was observed in T-bet deficient Th1 cells (9%) and an intermediate phenotype observed in the heterozygous T cells (46%). Therefore the function of T-bet in controlling IFN-γ production is highly dosage sensitive, a finding that is consistent with the known function of other T-box family genes in which haploid insufficiency of Tbx3 and Tbx5 leads to the genetic disorders, Ulnar Mammary and Holt-Oram syndromes, respectively. Another possibility is monoallelic, rather than biallelic expression of T-bet as documented for certain cytokine genes (e.g. IL-2 and IL-4).

D. Conclusion

The analysis of the immune system in mice that lack T-bet, as described above, firmly establishes T-bet as a transcription factor that is required for Th1 lineage commitment. Further, it is clear that one mechanism by which this occurs is the control, of IFN-γ gene transcription by T-bet in vivo. Mice that lack T-bet do not develop a robust Th1 compartment as evidenced by the failure of CD4⁻T cells to produce the hallmark Th1 cytokine, IFN-γ even upon deliberate polarization. A large number of transcription factors have been implicated in the control of the IFN-γ gene. ATF-2, NFκB, AP-1, YY1, NF-AT and Stat sites in the IFN-γ promoter or introns are functionally important in vitro, but are not responsible for the tissue-specific expression of IFN-γ (Young et al., 1994, Sica et al., 1997; Penix et al., 1996; Xu et al., 1996; Sweetser et al., 1998), nor do they selectively control IFN-γ in vivo. Here we have demonstrated that T-bet is selectively required for IFN-γ production in CD4+ T cells and NK cells in vivo. Given the pathogenic role of Th1 cells in autoimmunity and cancer, and their protective role in asthma, these observations have clear implications for the treatment of human disease.

Example 15

T-bet is Required for Interferon-γ Production and Lineage Commitment in CD4 but not CD8 T Cells T-bet is expressed in both CD4 and CD8 T cells. To determine whether T-bet is involved with IFN-γ production in both CD4 and CD8 T cells, the following experiments were performed. Purified CD4 and CD8 T cells were stimulated for 72 hrs with plate bound anti-CD3, anti-CD28, rIL-12 and rIL-18, RNA prepared and northern blot analysis performed using T-bet, IFN-γ, and HPRT probes. CD8 T cells and CD4 T cells purified from T-bet$^{-/-}$, T-bet$^{+/-}$ and T-bet$^{+/+}$ LN were stimulated with plate-bound anti-CD3 and anti-CD28 for 7 days. ICC analysis was performed after 5 hours stimulation with PMA (50 ng/ml) and ionomycin (1 uM). IFN-γ production was measured by ELISA 24 hrs after restimulation with anti-CD3/anti-CD28. CTL precursors from T-bet$^{+/+}$ or $^{-/-}$ splenocytes were primed in vitro with Concanavalin A (5 ug/ml or plate bound anti-CD3/anti-CD28 and 100 U/ml hIL-2 for 5 days (32). On day 5 CD8 T cells (H-2$^b$) were purified by positive selection using MACS purification and incubated for 4 hours with $^{51}$Cr labeled P815 (H-2$^d$) allogeneic target cells at the indicated effector to target ratios.

The results of these experiments demonstrated that in contrast to CD4 T and NK cells, T-bet is not involved in controlling IFN-γ production in the other major subset of T cells, the cytotoxic CD8 T cell. This observation demonstrates that CD4 and CD8 T cells, while closely related, and arising from a common progenitor in the thymus, have nevertheless evolved to utilize distinct mechanisms of transcriptional control of a shared cytokine.

Example 16

T-bet Regulates IgG Class Switching and Pathogenic Autoantibody Production

Because of its role in Th1 responses, it is likely that T-bet would play a critical role in systemic autoimmune syndromes like lupus, which rely heavily upon Th1 T cells for pathogenesis. Lupus-prone T-bet-deficient mice were generated by intercrossing a T-bet-deficient line with the MRL/MpJ-Fas (CD95)$^{lpr/lpr}$ murine lupus strain, generating animals of four genotypes, T-bet$^{+/+}$Fas$^{+/+}$, T-bet$^{-/-}$Fas$^{+/+}$, T-bet$^{+/+}$Fas$^{lpr/lpr}$ (T-bet+lpr), and T-bet$^{-/-}$Fas$^{lpr/lpr}$(T-bet–lpr). Flow cytometric analyses of tissues from adult 6-week old animals revealed that T-bet did not have a significant effect upon the proportional numbers of CD4+ or CD8+ T cells, or B220-positive B cells in spleen or lymph node. Upon aging, T-bet–lpr animals were protected from immune-complex renal disease, which was characterized by strikingly diminished glomerular, interstitial and perivascular inflammation as well as glomer-ular immune complex deposition. Also, they developed significantly less humoral autoimmunity as assessed by the fluorescent antinuclear antibody test and two tests for anti-DNA antibodies. Their sera contained some, albeit diminished, autoimmunity to DNA as assessed by ELISA, but were unable to recognize native, double-stranded DNA as assessed by Crithidia immunofluorescence, suggesting the presence of generalized (e.g., anti-ssDNA), but not matured (e.g., anti-dsDNA) autoimmunity in T-bet–lpr animals. Compared to T-bet$^+$lpr animals, T-bet$^-$lpr animals were relatively protected from glomerulonephritis-related mortality (survival of 57%, n=7 versus 100%, n=6, at 28 weeks, respectively).

Surprisingly, T-bet$^-$lpr animals continued to develop other manifestations consistent with T-cell autoimmunity, including cutaneous, salivary gland, and hepatic infiltrates, as well as lymphoid organomegaly, often in excess of their T-bet$^+$lpr littermates. These lymphoid infiltrates consisted mostly of T cells, as assessed by immunohistopathology. Such findings suggest that the Th1-dominant T cell autoimmunity in this model was largely intact in the absence T-bet. Although T-bet was required for the production of IFN-γ by naive CD4$^+$ T cells from CD95-intact animals, T-bet$^-$lpr T cells produced excess cytokines, including IFN-γ and IL-4, and demonstrated similar proliferative activity in an autologous mixed lymphocyte reaction, compared to their T-bet$^+$lpr littermates.

Since pathogenic autoantibodies are necessary and sufficient to induce immune complex glomerulonephritis, and T-bet is induced in both human and murine B cells upon activation, it is likely that T-bet is directly required in B lymphocyte function. As assessed by serum levels, T-bet was required for the complete expression in these lupus-prone animals of hypergammaglobulinemia IgG2a, IgG2b and IgG3, a requirement amplified in Fas$^{lpr/lpr}$ animals IgG2a levels, however, were severely diminished in T-bet-deficient sera from either Fas genotype. IgG2a immune deposits were significantly reduced in the kidneys of T-bet–lpr animals. Purified T-bet-deficient B cells were unable to complete class switching to IgG2a when stimulated in vitro, as assayed by secreted immunoglobulin. Class switching to IgG2b and IgG3 was significantly diminished, but nevertheless present in T-bet-deficient cells. These deficits appeared to occur at the transcriptional level, since in class-switching assays T-bet-deficient B cells were neither able to accumulate surface IgG2a nor generate germline or postswitch IgG2a transcripts. Conversely, T-bet-deficient B cells produced excess amounts of the Th2-related isotypes IgG1 and IgE. These deficits did not simply result from an unopposed effect of IL-4, because the addition of up to 10 μg/mL anti-mIL-4 antibodies to B cell cultures did not affect the IgG2a deficiency, or the IgG1/IgE excess. These observations suggest a profound role for T-bet in the regulation of IgG2a at the level of the germline transcript, and further implicate it in the regulation of IgG1 and IgE.

Further evidence that T-bet directly controls the transcription of IgG2a includes the following. Transfection of the murine pre-B cell lymphoma 18.81 with a T-bet expression plasmid induced endogenous IgG2a germline transcripts. In addition, transduction of primary T-bet-deficient B cells with a T-bet-expressing retrovirus confers the ability to generate IgG2a germline transcripts, as well as secreted IgG2a. Furthermore, purified B cells from a CMV-T-bet transgenic mouse line, which expresses T-bet under the control of the CMV early promoter, produced increased amounts of IgG2a when stimulated in vitro with LPS and rmIFN-γ compared to B cells from nontransgenic littermates (490±50 ng/mL vs. 1058±120 ng/mL, n=3). To determine if T-bet played a role in the IFN-γ signalling pathway, the CMV-T-bet transgenic line was crossed with an IFN-γ receptor (IFNγR)-deficient background T-bet was able to augment the production of IgG2a, this time in the absence of IFN-γ signaling. The proliferative capacity of T-bet deficient B cells, as well as their ability to upregulate several markers of B cell activation, including IFN-γ, IL-6, IL-10, and GM-CSF, was unaffected in vitro, further suggesting a direct role for T-bet in the regulation of IgG transcription, independent of B cell activation status.

T-bet therefore confers upon B lymphocytes the ability to class switch to IgG2a in response to IFN-γ. T-bet also plays a significant role in the regulation of other Ig isotypes, and thus, plays a major role in the regulation of pathogenic autoantibody production. Without being bound by one particular theory, given its role as a transcription factor, T-bet likely regulates class switching via control of germline transcripts, which have been strongly implicated as a prerequisite to isotype switch recombination. Alternatively, T-bet may participate in mediating accessibility of the IgG locus to transcriptional or recombinatorial factors, as it does for IFN-γ in CD4 T cells. In either scenario, T-bet serves as a mediator of signals to transactivate the classical IFN-□-related immuno-globulin isotype IgG2a, yet inhibits the classical Th2-related isotypes IgG1 and IgE. While T-bet is capable of inducing germline transcripts in the absence of exogenous IFN-γ, complete wild-type-level production of IgG2a appears to require IFN-□ signaling, suggesting that T-bet cooperates with another factor in the IFNγR pathway, such as STAT1, or at least require signaling messages, such as tyrosine phosphorylation, e.g.,activated by the IFNγR for complete activity.

The identification of T-bet as a regulator of IgG isotype class switching may prove helpful in future transcriptional analyses of the non-IL4-dependent IgG subclasses, whose study has been greatly hindered by their apparently very distant locus control regions. Although the present results demonstrate that T-bet can transactivate endogenous IgG2a transcripts in whole cells, it cannot transactivate a reporter construct consisting of 3 kB of putative IgG2a promoter upstream of the I exon, at least in 18.81 cells. Thus, the control region for IgG2a, at least as it relates to T-bet, may be quite distant. The present results are therefore of particular significance given the complete yet selective absence of IgG2a germline transcripts in the T-bet-deficient B cells. In comparison, several reported immunoglobulin isotype immunodeficiencies caused by other transcription factor knockouts involve multiple Ig isotypes and/or other developmental B cell defects. Thus, the present invention identifies T-bet as an isotype-specific participant in the class switch mechanism.

Example 17

T-bet Regulates Mucosal T Cell Activation in Experimental Colitis and Crohn's Disease Crohn's disease and ulcerative colitis are the two major forms of inflammatory bowel diseases (IBD) in humans. Whereas Crohn's disease is characterized by a transmural, granulomatous inflammation that can occur anywhere in the gastrointestinal tract, ulcerative colitis causes a more superficial, continuous inflammation that is restricted to the large bowel. Although the etiology of the diseases is unknown, it has been suggested that an activation of the mucosal immune system in response to bacterial antigens with consecutive pathologic cytokine production and activation of matrix metalloproteinases plays a key pathogenic role. In particular, cytokines produced by T lymphocytes appear to initiate and perpetuate chronic intestinal inflammation. Interestingly, cytokine production by lamina propria CD4+ T lymphocytes differs between Crohn's disease and ulcerative colitis. Whereas the former disease is associated with increased production of T helper 1 (Th1) type cytokines such as IFN-γ and TNF, the latter disease is associated with T cells producing large amounts of the Th2 type cytokine IL-5 while IFN-γ production is unaffected. In both Th1- and Th2-mediated IBD, the immunosuppressive cytokine TGF-β, mainly secreted by Th3 cells and a unique population of regulatory T cells (Tr), provides a powerful protective effect.

A. Reciprocal Expression of GATA-3 and T-bet in Lamina Propria T Cells from Patients with Crohn's Disease Since changes in cytokine production by lamina propria T cells have been implicated as a key phenomenon in the pathogenesis of inflammatory bowel diseases (IBD), a series of experiments on the expression of T-bet by purified lamina propria (LP) T cells in IBD patients was performed. Immunofluorescence double staining studies showed an accumulation of T-bet expressing LP T cells in patients with Crohn's disease (CD). In addition, it was found that T-bet was strongly expressed in both the cytoplasm and the nucleus of LP mononuclear cells in patients with Crohn's disease, while only a weak staining in perinuclear areas or no staining was observed in control patients and patients with ulcerative colitis. To verify increased expression of T-bet in patients with Crohn's disease, nuclear extracts of purified LP T cells from patients with Crohn's disease and control patients were isolated and expression of T-bet by EMSA and Western blot analysis was analyzed. Patients with Crohn's disease expressed higher amounts of nuclear T-bet compared with control patients.

The expression of GATA-3 in LP T cells from CD patients was also assessed. GATA-3 expression was downregulated in LP T cells from CD patients compared to control patients, as assessed by immunohistochemical double staining analysis for CD3 and GATA-3 on colon cryosections. These data are indicative of a reciprocal expression pattern of GATA-3 and T-bet in CD LP T cells that is associated with increased IFN-γ but decreased IL-4 and IL-5 production in this disease.

B. Induction of T-bet Expression in Th1- But Not Th2-mediated Animal Models of Chronic Intestinal Inflammation Nuclear proteins from T cell enriched lamina propria mononuclear cells (LPMC) in various animal colitis models were isolated and T-bet expression was assessed by EMSA and Western blot analysis. T-bet was found to be strongly expressed in T cell enriched LP cells in the TH1-mediated colitis model observed in SCID or RAG mice reconstituted with CD62L+ CD4+ T cells. Time course studies showed that increased T-bet expression in the colon occurred as early as 3 weeks after cell transfer before the onset of colitis. Maximum expression was noted 6 weeks after cell transfer when the mice started to develop colitis, although increased T-bet expression was also observed in the full-blown colonic inflammation seen at 12 weeks after T cell transfer. Furthermore, increased T-bet expression was consistently noted in two additional TH1-mediated animal models of chronic intestinal inflammation, namely colitis in IL-10 deficient mice and colitis induced by the hapten reagent 2,4,6,-trinitrobenzene sulfonic acid (TNBS). In contrast, unchanged or lower levels of T-bet were detected in T cell enriched LP cells in oxazolone colitis and TCRα$^{-/-}$ μ$^{-/-}$ associated colitis, two colitis models that are believed to be mediated by IL-4 producing T cells and Th2 cells, respectively. These findings indicate that T-bet is potentially a key regulator of the mucosal TH1/TH2 cytokine balance in experimental colitis in vivo.

C. Retroviral or Transgenic Overexpression of T-bet Induces an Early Onset of Severe CD62L+ CD4+ Th1 T Cell-mediated Colitis in SCID Mice To determine the potential regulatory role of T-bet in Th1-mediated colitis in vivo by transgenic or retroviral overexpression techniques, the colitogenic potential of T cells after infection with a T-bet retrovirus was analyzed. FACS-sorted GFP+ CD62L+ double positive CD4+ T cells that were retrovirally transduced with T-bet induced an earlier onset of severe colitis in SCID mice compared to SCID mice reconstituted with control transduced CD62L+ T cells, as assessed by weight loss curves. This phenotype demonstrates that overexpression of T-bet accelerates development of TH1-mediated chronic intestinal inflammation. It was further observed that transfer of CD62L+ CD4+ T cells from T-bet transgenic mice induced an earlier onset of colitis activity in SCID mice compared to T cells from wild-type littermates.

D. Mice Lacking T-bet (T-bet Knockout) are More Susceptible to Th2-mediated Colitis To determine the susceptibility of mice in which the T-bet gene has been inactivated by homologous recombination for T cell-mediated colitis, T-bet deficient mice that exhibited an altered susceptibility to Th2-mediated colitis using the oxazolone-induced colitis model that has previously been shown to be dependent on IL-4 production by T cells were analyzed. The T-bet knockout mice showed enhanced susceptibility to oxazolone-induced colitis compared to both wild-type litterinates and heterozygous T-bet mice, based on by weight curve), macroscopic and histopathologic criteria. This was accompanied by a marked increase in IL-4 production by splenic CD3+ T cells, while IFN-γ production by these cells was not significantly changed.

To determine whether the observed increase in IL-4 production was responsible for the differences between wild-type and T-bet knockout mice, antibodies to IL-4 or control rat Ig to T-bet knockout mice after oxazolone sensitization were administered. Antibodies to IL-4 suppressed histologic colitis activity in oxazolone-treated T-bet knockout mice indicating that the protective role of T-bet in Th2-mediated colitis is due to its direct or indirect regulation of IL-4 production.

E. T-bet Deficiency Protects from Th1-mediated Experimental Colitis in an Adoptive Transfer Model Using CD62L+ CD4+ T Cells The effects of T-bet deficiency in Th1-mediated colitis induced by transfer of CD4+ CD62L+ CD45Rb$^{high}$ T cells in SCID and RAG knockout mice were assessed. Transfer of T-bet expressing CD4+ CD62L+ T cells from wild-type mice resulted in clinical and endoscopic signs of severe colitis. In contrast, transfer of T-bet$^{-/-}$ CD4+ CD62L+ T cells failed to induce chronic diarrhea, weight loss, rectal prolapse and endoscopic signs of colitis. Furthermore, transfer of T-bet deficient T cells resulted in a markedly reduced colitis activity in SCID mice reconstituted with CD62L+ CD45Rb$^{high}$ CD4+ T cells in three independent experiments, as assessed by macroscopic and histologic criteria. This protective effect of T-bet deficiency on CD62L+ CD4+ T cell-induced colitis was at least as pronounced as that seen upon transfer of STAT-1-deficient CD62L+ CD4+ T cells (histopathologic score: STAT-1$^{-/-}$ reconstituted mice: 1.25+/−0.9 vs. T-bet$^{-/-}$ reconstituted mice: 0.8+/−0.2). LP T cells from T-bet knockout T cell reconstituted mice produced less IFN-γ compared to LP cells from wild-type T cell reconstituted mice (336+/−24 pg/ml versus 1159+/−25 pg/ml) indicating that T-bet deficiency suppresses proinflammatory cytokine production by mucosal CD4+ T cells. Interestingly, CD4+ CD62L+ T cells from heterozygous T-bet mice showed a marked variability to induce colitis in three independent experiments, likely due to a threshold effect of T-bet expression in controlling cytokine gene expression and hence the colitogenic potential of T cells.

F. T-bet Controls the Mucosal Balance Between IFN-1 and IL-4 Production by T Cell Enriched Lamina Propria Cells in the Absence of Colitogenic Stimuli The structure of the lamina propria and cytokine production by lamina propria mononuclear cells (LPMC) in mice lacking T-bet was assessed. No macroscopic or histologic abnormalities in the small and large bowel of T-bet heterozygous and T-bet knockout mice in the absence of colitogenic stimuli was observed. To analyze cytokine production by T cell enriched LPMC from T-bet deficient mice and wild-type littermates, cells were stimulated by anti-CD3 plus anti-CD28 for 48 hours and cytokine production in culture supernatants was determined by ELISA. Two independent experiments demonstrated that T cell enriched LPMC from T-bet knockout mice secreted lower levels of IFN-$\gamma$ than cells from wild-type littermates in the absence of colitogenic stimuli. In contrast, production of the Th2 type cytokines IL-4, IL-6 and IL-10 by T cell enriched LPMC was augmented in T-bet deficient animals compared to wild-type mice. In particular, IL-4 production by T-bet$^{-/-}$ and T-bet$^{+/-}$ LPMC was increased compared to T-bet expressing LPMC from wild-type littermates (FIG. 7b). These changes in cytokine production were seen using LPMC from both the small and large bowel indicating that T-bet is a regulator of the mucosal Th1/Th2 cytokine balance in the entire gut immune system.

Whether increased Th2 cytokine production by LPMC in T-bet knockout mice was associated with evidence for activated IL-4 signaling in LP T cells was assessed next. There was increased GATA-3 expression in nuclear extracts from T cell enriched LPMC of T-bet deficient mice, as shown by both gel retardation assays and Western blot analysis, consistent with an increased presence of Th2 effector T cells in the mucosa of T-bet knockout mice.

G. T-bet Deficient Regulatory CD62L$^-$ CD4$^+$ T Cells Show Enhanced Protective Functions in Th1-mediated Colitis and Exhibit Increased TGF-D Production and Signaling To determine the effect of T-bet deficiency on TGF-$\beta$ production and signaling in T cells, the T cell enriched LPMC in T-bet knockout mice were observed and shown to produce increased arnounts of TGF-$\beta$ compared to cells from wild-type littermates. This increased production of TGF-$\beta$ in the absence of T-bet could be important for the regulatory function of T-bet in colitis, since TGF-$\beta$ production by T cells has been recently suggested to play a key role in suppressing chronic intestinal inflammation. In intestinal inflammation, TGF-$\beta$ is mainly produced by a unique population of regulatory CD25$^+$ CD45RB$^{low}$ CD62L$^-$ CD4$^+$ T cells that have been shown to suppress colitis activity in SCID mice when cotransfered with CD4$^+$ CD62L$^+$ T cells. Furthermore, at least in the spleen, IL-4 producing T cells have been shown to produce high amounts of TGF-$\beta$ in secondary cultures.

Both splenic CD62L$^+$ and CD62L$^-$ CD4$^+$ T cells from healthy mice expressed large amounts of nuclear T-bet as shown by Western blot analysis. Splenic CD25$^+$ cells, however, showed lower amounts of nuclear T-bet expression. Furthermore, CD62L$^-$ CD45RB$^{low}$ CD4$^+$ T cells from T-bet knockout mice showed decreased expression of Smad7, an inhibitory Smad protein that is induced by IFN-$\gamma$ and suppresses TGF-$\beta$ signaling in T cells, compared to cells from wild-type mice. Consistently, splenic T-bet$^{-/-}$ CD62L$^-$ CD4$^+$ T cells exhibited increased nuclear Smad3 expression compared to T-bet expressing CD62L$^-$ CD4$^+$ T cells indicative of enhanced TGF-$\beta$ signaling. Based on these findings the potential regulatory capacity of CD62L$^-$ CD4$^+$ T lymphocytes from wild-type, T-bet heterozygous and T-bet knockout mice to suppress colitis induced by T-bet expressing CD62L$^+$ CD4$^+$ T cells was analyzed. Cotransfer of regulatory CD62L$^-$ CD4$^+$ T cells plus naive CD62L$^+$ CD4$^+$ T cells from T-bet expressing wild-type mice led to less severe colitis compared to mice reconstituted with CD62L$^+$ CD4$^+$ T cells confirming a protective role for this T cell subset in vivo. Moreover, cotransfer of T-bet-deficient regulatory CD62L$^-$ CD4$^+$ T cells caused a more pronounced protective effect on CD62L$^+$ CD4$^+$ T cell-mediated colitis compared to regulatory CD62L$^-$ cells from wild-type mice. This finding was associated with an increased production of TGF-$\beta$ by lamina propria T cells from reconstituted mice and by an expansion of the number of regulatory CD4$^+$ CD25$^+$ T cells in the spleen of reconstituted mice.

H. T-bet Controls TGF-$\beta$ Production and Signaling in Regulatory T Cells

Regulatory T cells producing IL-10 or TGF-$\beta$ mediate protective effects in Th1-mediated colitis by suppressing the activity of T lymphocytes. To determine the if T-bet has a role in TGF-$\beta$ production and signaling in regulatory T cells, the following studies were performed. Cells were cultured in the presence of antibodies to CD3 and CD28 with or without recombinant IL-4 and TGF-$\beta$ (1 ng/ml). Cellular extracts were made after 48 hours and analyzed for the expression of T-bet and beta-actin by Western blot analysis. To determnine whether TGF-$\beta$ is produced by T cell enriched LPMC from wild-type (WT), T-bet heterozygous (HET) and T-bet knockout (KO) mice in the absence of colitogenic stimuli, cells were stimulated with antibodies to CD3 plus CD28 and supernatants were analyzed by ELISA. To determine whether T-bet is expressed in splenic CD25$^+$, CD62L$^+$ and CD62L$^-$ CD4$^+$ T cells from healthy wild-tpye cytoplasmic (CYT) and nuclear (NUC) extracts from these cells were isolated and analyzed for T-bet expression by Western blotting. To determine whether TGF-$\beta$-mediated signaling is increased in T-bet deficient CD62L$^-$ CD4$^+$ T cells, CD62L$^-$ CD4$^+$ T cells from wild-type and T-bet knockout mice were stimulated with anti-CD3 plus anti-CD28 and rIFN-$\gamma$ for 12 hours followed by protein extraction and Western blot analysis. Cellular extracts were analyzed for Smad7 expression whereas nuclear extracts were analyzed for Smad3 levels. To measure the inflammation score of mice reconstituted with CD62L$^+$ CD4,$^+$ T cells from wild-type mice and CD62L$^-$ CD4 + T cells from T-bet knockout mice (KO) and wild-type (WT) control mice were measured.

The foregoing studies demonstrate a regulatory role for T-bet in mucosal cytokine production. Specifically, the present invention demonstrates that CD62L$^-$ CD4$^+$ T cells from T-bet knockout mice exhibit a stronger protective effect on CD62L$^+$ CD4$^+$ T cell-induced colitis than the corresponding cell population from wild-type mice. This observation is related to differences in TGF-$\beta$ production and signaling, as CD62L$^-$ CD4$^+$ T cells from T-bet deficient mice exhibited increased nuclear Smad3 expression. After binding of TGF-$\beta$ to its receptor on T cells, Smad3 is interacts with the TGF-$\beta$ receptor I followed by importin-1$\beta$ and RanGTPase-mediated import of Smad3 into the nucleus where it controls expression of $\beta$ target genes. IFN-$\gamma$ has been previously shown to inhibit TGF-$\beta$ signaling by a Jak1/STAT-1-mediated rapid activation of the synthesis of the inhibitory Smad-7 protein, which in turn can prevent the interaction of Smad3 with the TGF-β type I receptor. Furthermore, Smad7 can form a complex with the ubiquitin-ligase Smurf2 that targets the TGF-β receptor for degradation. Thus, the reduced production of IFN-γ by splenic CD4$^+$ T cells and T cell enriched lamina propria cells in T-bet deficient animals causes reduced expression of Smad7 followed by increased TGF-β signaling via Smad3/4. In fact, CD62L$^-$ CD4$^+$ T cells from T-bet deficient mice express reduced levels of Smad7 compared to T cells from wild-type mice.

Since administration of neutralizing antibodies to TGF-β is known to suppress the protective capacity of CD62L$^-$ CD4$^+$ T cells on Th1-mediated colitis, the present invention demonstrates that the enhanced regulatory capacity of T-bet deficient CD62L$^-$ CD4$^+$ cells is due to increased TGF-β production and signaling. The enhanced TGF-β production of T-bet deficient T cells is likely augmented after T cell transfer, as TGF-β has been demonstrated to positively regulate its own production. The relevance of a defect in TGF-β1 expression or TGF-β-mediated signaling via Smad3 for the mucosal immune system has been shown by the observation that knockout mice for these proteins develop T cell-mediated chronic intestinal inflammation. TGF-β in turn downregulates T-bet expression in mucosal cells, demonstrating a reciprocal relationship between TGF-β and T-bet levels in T cells.

In summary, the present invention identifies T-bet as a master switch for T cell-mediated chronic intestinal inflammation and the regulation of protective immune responses by TGF-β. T-bet controls Th1 and Th2 cytokine production in colitis and its levels are downregulated by TGF-β. Furthermore, downregulation of T-bet is associated with increased TGF-β levels due to failure of T-bet-mediated activation of Smad7. Thus, modulation of T-bet function is a valuable target for local therapeutic intervention in Th1-mediated chronic intestinal inflammation such as is observed in Crohn's disease.

Example 18

Mice Lacking T-bet Spontaneously Develop Airway Changes Consistent with Human Asthma Human asthma is associated with reversible airway obstruction, airway inflammation, airway hyperresponsiveness (AHR) and, in chronic asthma, air-way remodeling. Murine models of asthma mimic many of the features of the human disease. In these models the production of IL4, IL-5 and IL-13 have been associated with the development of an asthma-like phenotype. In an adoptive transfer model, enhanced expression of IFNγ by Th1 cells in the airway protects against allergic disease, but the presence of Th1 cells does not attenuate Th2 cell-induced airway hyperreactivity and inflammation.

To determine whether T-bet was expressed in the lungs of normal individuals and in patients with allergic asthma, immunohistochemistry using a mAb to T-bet was performed. The results revealed expression of T-bet in thirteen normal control lungs, but very little expression in seven patients with allergic asthma. Double staining for CD4 and T-bet in consecutive sections showed that most of the cells expressing T-bet were CD4$^+$ T cells. Thus, T-bet deficiency recapitulates many aspects of the asthmatic phenotype.

Naïve mice, i.e., neither antigen sensitized nor challenged, with a targeted deletion of T-bet were examined to ascertain if such animals would manifest various aspects of the induced asthma phenotype. Compared to wild type (wt) mice, those either heterozygous (T-bet +/−) or homozygous for a targeted deletion of T-bet (T-bet −/−) exhibited greater airway responsiveness, as measured in unanesthetized animals by the enhanced pause response (Penh), following aerosol exposure to methacholine. These findings were confirmed in mice that had been sensitized by systemic exposure to ovalbumin but sham challenged with aerosol phosphate buffered saline (termed OVA/PBS), by the demonstration that both T-bet (+/−) and (−/−) mice manifested airway hyper-responsiveness, as compared to wt mice, when the pulmonary resistance response resulting from intravenous infusion of methacholine, was used as the outcome indicator. Histopathologic analysis of the airways of T-bet (−/−) mice at baseline demonstrated peribronchial and perivenular infiltration with eosinophils and lymphocytes as compared to control wild-type littermates. T-bet deficient mice had increased deposition of fibroblast-like cells beneath the basement membrane. Eosinophils were not present in the bronchoalveolar lavage fluid of T-bet deficient mice despite enhanced recovery of IL-5. T-bet +/− heterozygous mice, that have only a 50% reduction in T-bet protein, displayed a phenotype very similar to mice with a complete absence of T-bet.

In contrast to the spontaneous asthma observed in T-bet−/− and +/− animals, many murine models of asthma, depend on a protocol of priming and sensitization to allergen to elicit disease. Thus, OVA aerosol challenge of mice previously sensitized to OVA was tested to determnine whether it would lead to enhanced airway responsiveness in T-bet deficient mice as it does in wt mice. The pulmonary resistance response observed after intravenous infusion of methacholine in T-bet deficient mice sensitized to OVA and receiving aerosol challenge was similar to that observed in mice who did not receive aerosol OVA challenge After OVA/OVA exposure, no differences were observed between wt or T-bet deficient mice with respect to the infiltration of the airways with eosinophils or lymphocytes or in the cellular composition of the bronchoalveolar lavage fluid. Thus, mice with reduced or absent levels of T-bet display a spontaneous, non-allergen-induced asthma phenotype that is not further exacerbated with antigenic stimulation.

The thickness of the sub-epithelial collagen layer was evaluated in wt and T-bet −/− and +/− deficient animals. In the wt animals there was minimal deposition of collagen beneath the basement membrane, while in the T-bet deficient mice the sub-basement membrane collagen layer was significantly thicker than it was in wild type mice. In addition to a thickened collagen layer, there were increased numbers of bronchial myofibroblasts, as assessed by immunostaining for alpha-smooth muscle actin. These data indicate that the airways of T-bet deficient mice undergo remodeling similar to that observed in humans with chronic asthma.

Whether these structural changes in the airway were associated with a difference in the patterns of cytokine expression between wt and T-bet deficient mice was examined TGF-beta, a potent stimulator of tissue fibrosis, TNFα and Il-4, another pro-inflammatory cytokine implicated in the chronic remodeling of the airways in asthma, were recovered in increased amounts from the BALF of mice homozygous for the T-bet targeted deletion. T-bet deficiency induced a selective alteration in patterns of cytokine expression as no significant changes were observed in IL-10 and IL-6 production. Although the physiological and histologic findings were similar in mice either hetero- or homozygous for the targeted deletion, only the homozygous mice exhibited an increased production of cytokines.

The identity of the cells in T-bet deficient mice responsible for airway hyperreactivity and airway inflammation was examined by adoptive transfer of spleen CD4+ cells from different groups of OVA sensitized mice into histocompatible SCID mice. To enhance the localization of the transferred T cells into the lungs of mice, the OVA aerosol was administered one day before adoptive transfer of the T cells. On the day following the adoptive transfer, OVA aerosol exposures were begun and continued for three days. Four days after cell transfer, lung mechanics were evaluated. Control SCID mice received an intraperitoneal infusion of saline rather than T cells suspended in saline. Recipients of wt spleen CD4 cells had comparable airway responsiveness to wt mice that received OVA sensitization but were not challenged. Mice that had been reconstituted with CD4 cells lacking T-bet showed increased airway hyperresponsiveness as compared to mice reconstituted with CD4 cells derived from wild-type littermates and similar to that of OVA sensitized mice lacking T-bet. CD4 staining of BALF cells harvested after measurement of lung mechanics was performed to assure that CD4+ cells were recruited to the lung; the proportion of lymphocytes that were CD4 positive in wt (+/+) mice was 38.9%+/−2.2; in CD4 T-bet (+/−) mice was 39.57%+/−6.48; and in T-bet (−/−) mice was 38.5%+/−5.48. In addition, the lungs of SCID mice reconstituted with CD4 cells derived from T-bet (−/−) mice exhibited increased IL-4 in the BALF as compared to recipient mice reconstituted with spleen CD4+ cells derived from wt mice, demonstrating that the airway hyperreactivity observed in T-bet (−/−) mice is T-cell mediated.

The present invention demonstrates that targeted deletion of T-bet, in the absence of an induced inflammatory response, results in a physiological and inflammatory phenotype in murine airways similar to that created by allergen exposure in sensitized mice. In addition to acute inflammatory changes, T-bet deficient mice demonstrate airway remodeling consistent with asthma that is reminiscent of the human disease. Remarkably, this phenotype exists spontaneously and is full-blown, since, when sensitized and challenged with allergen, T-bet deficient mice fail to enhance either their physiological or pathologic responses.

EQUILVALENTS

Those skilled in the art will recognize, or be able to ascertain using no more than routine experimentation, many equivalents to the specific embodiments of the invention described herein. Such equivalents are intended to be encompassed by the following claims.

We claim:

1. An isolated nucleic acid molecule comprising a nucleotide sequence encoding the polypeptide of SEQ ID NO:2, or which is complementary thereto over the full length of said nucleic acid molecule.

2. The nucleic acid molecule of claim , which comprises the nucleotide sequence shown in SEQ ID NO:1, or which is complementary thereto over the full length of SEO ID NO:1.

3. The isolated nucleic acid molecule of claim 1, further comprising a nucleotide sequence encoding a heterologous polypeptide.

4. An isolated nucleic acid molecule, which has at least 90% nucleotide identity with SEQ ID NO:1 over its full length, and which encodes a polypeptide that binds a consensus T-box site in DNA and induces IFN-γ production in CD4+ cells.

5. The nucleic acid molecule of claim 4, wherein the polypeptide has at least one activity selected from the group consisting of: inhibiting production of IL-2, and inducing the differentiation of Thp cells and Th2 cells into Th1 cells.

6. The nucleic acid molecule of claim 4, wherein the identity is determined by the BLAST program using the default Blastn matrix.

7. An isolated nucleic acid molecule which hybridizes to a full length complement of the nucleic acid molecule set forth in SEQ ID NO:1 in 6×SSC at 45° C., followed by one or more washes in 0.2×SSC, 0.1% SDS at 65° C. under stringent conditions, wherein said nucleic acid molecule encodes a polypeptide that binds a consensus T-box site in DNA and induces IFN-γ production in CD4+ cells.

8. An isolated nucleic acid molecule which encodes a polypeptide comprising an amino acid sequence at least 95% identical to the amino acid sequence of SEQ ID NO:2, wherein said nucleic acid molecule encodes a polypeptide that binds to a consensus T-box site in DNA and induces IFN-γ production in CD4+ cells.

9. The nucleic acid molecule of claim 8, wherein the polypeptide has at least one activity selected from the group consisting of: inhibiting production of IL-2, and inducing the differentiation of Thp cells and Th2 cells into Th1 cells.

10. An isolated nucleic acid molecule consisting of at least 700 contiguous nucleotides of SEQ ID NO:1 which sequence encodes a T-box domain, or an isolated nucleic acid molecule consisting of a nucleotide sequence complementary to the at least 700 contiguous nucleotides of SEO ID NO:1.

11. An isolated nucleic acid molecule comprising the nucleotide sequence shown in SEQ ID NO:1, wherein the nucleic acid molecule is labeled with a detectable substance.

12. An isolated nucleic acid molecule comprising at least 700 contiguous nucleotides of SEQ ID NO:1 which sequence encodes a T-box domain, or an isolated nucleic acid molecule comprising a nucleotide sequence complementary to the at least 700 contiguous nucleotides of SEQ ID NO:1.

13. A vector comprising the nucleic acid molecule of any one of claims 4, 7, 10, and 12.

14. The vector of claim 13, which is an expression vector.

15. An isolated host cell containing the vector of claim 14.

16. A method for producing a T-bet protein comprising culturing the host cell of claim 15 in a suitable medium until a T-bet protein is produced.

17. The method of claim 16, further comprising isolating the T-bet protein from the medium or the host cell.

18. The expression vector of claim 14, comprising a constitutive promoter.

19. The expression vector of claim 14, comprising an inducible promoter.

20. The expression vector of claim 14, comprising a tissue-specific regulator element.

21. An isolated nucleic acid molecule comprising a nucleotide sequence encoding the polypeptide of SEQ ID NO:4, or which is complementary thereto over the full length of said nucleic acid molecule.

22. The nucleic acid molecule of claim 21, which comprises the nucleotide sequence shown in SEQ ID NO:3, or which is complementary thereto over the full length of SEQ ID NO:3.

23. The isolated nucleic acid molecule of claim 21, further comprising a nucleotide sequence encoding a heterologous polypeptide.

24. An isolated nucleic acid molecule, which has at least 90% nucleotide identity with SEQ ID NO:3 over its full length, and which encodes a polypeptide that binds a consensus T-box site in DNA and induces IFN-γ production in CD4+ cells.

25. The nucleic acid molecule of claim 24, wherein the polypeptide has at least one activity selected from the group consisting of: inhibiting production of IL-2, and inducing the differentiation of Thp cells and Th2 cells into Th1 cells.

26. An isolated nucleic acid molecule which hybridizes to a full lenght complement of the nucleic acid molecule set forth in SEQ ID NO:3 in 6×SSC at 45° C., followed by one or more washes in 0.2×SSC, 0.1% SDS at 65° C. under stringent conditions, wherein said nucleic acid molecule encodes a polypeptide that binds a consensus T-box site in DNA and induces IFN-γ production in CD4+ cells.

27. An isolated nucleic acid molecule which encodes a polypeptide comprising an amino acid sequence at least 95% identical to the amino acid sequence of SEQ ID NO:4, wherein said nucleic acid molecule encodes a polypeptide that binds to a consensus T-box site in DNA and induces IFN-γ production in CD4+ cells.

28. An isolated nucleic acid molecule consisting of at least 600 contiguous nucleotides of SEQ ID NO:3 which encodes a T-box domain, or an isolated nucleic acid molecule consisting of a nucleotide sequence complementary to the at least 600 continuous nucleotides of SEO ID NO:3.

29. An isolated nucleic acid molecule comprising at least 600 contiguous nucleotides of SEO ID NO:3 which sequence encodes a T-box domain, or an isolated nucleic acid molecule comprising a nucleotide sequence complementary to the at least 600 contiguous nucleotides of SEQ ID NO:3.

30. A vector comprising the nucleic acid molecule of any one of claims 24, 26, 28, and 29.

31. The vector of claim 30, which is an expression vector.

32. The expression vector of claim 31, comprising a constitutive promoter.

33. The expression vector of claim 31, comprising an inducible promoter.

34. The expression vector of claim 31, comprising a tissue-specific regulator element.

35. A host cell containing the vector of claim 31.

36. A method for producing a T-bet protein comprising culturing the host cell of claim 35 in a suitable medium until a T-bet protein is produced.

37. The method of claim 36, further comprising isolating the T-bet protein from the medium or the host cell.

38. An isolated nucleic acid molecule comprising the nucleotide sequence shown in SEQ ID NO:3, wherein the nucleic acid molecule is labeled with a detectable substance.

* * * * *

UNITED STATES PATENT AND TRADEMARK OFFICE
CERTIFICATE OF CORRECTION

PATENT NO. : 7,393,944 B2
APPLICATION NO. : 10/008264
DATED : July 1, 2008
INVENTOR(S) : Glimcher et al.

Page 1 of 1

It is certified that error appears in the above-identified patent and that said Letters Patent is hereby corrected as shown below:

In the Specification

Please delete the paragraph beginning at Column 1, Line number 13 and add the following:
This invention was made with government support under AG037833, AI036535, AI039646, AR062227, and AI007290 awarded by National Institutes of Health. The government has certain rights in the invention.

Signed and Sealed this
Seventh Day of January, 2025

Derrick Brent
*Acting Director of the United States Patent and Trademark Office*

SEQUENCE LISTING

```
<160> NUMBER OF SEQ ID NOS: 9

<210> SEQ ID NO 1
<211> LENGTH: 1608
<212> TYPE: DNA
<213> ORGANISM: Homo sapiens
<220> FEATURE:
<221> NAME/KEY: CDS
<222> LOCATION: (1)..(1605)

<400> SEQUENCE: 1 atg ggc atc gtg gag ccg ggt tgc gga gac atg ctg acg ggc acc gag      48
Met Gly Ile Val Glu Pro Gly Cys Gly Asp Met Leu Thr Gly Thr Glu
 1               5                  10                  15 ccg atg ccg ggg agc gac gag ggc cgg gcg cct ggc gcc gac ccg cag      96
Pro Met Pro Gly Ser Asp Glu Gly Arg Ala Pro Gly Ala Asp Pro Gln
            20                  25                  30 cac cgc tac ttc tac ccg gag ccg ggc gcg cag gac gcg gac gag cgt     144
His Arg Tyr Phe Tyr Pro Glu Pro Gly Ala Gln Asp Ala Asp Glu Arg
        35                  40                  45 cgc ggg ggc ggc agc ctg ggg tct ccc tac ccg ggg ggc gcc ttg gtg     192
Arg Gly Gly Gly Ser Leu Gly Ser Pro Tyr Pro Gly Gly Ala Leu Val
    50                  55                  60 ccc gcc ccg ccg agc cgc ttc ctt gga gcc tac gcc tac ccg ccg cga     240
Pro Ala Pro Pro Ser Arg Phe Leu Gly Ala Tyr Ala Tyr Pro Pro Arg
65                  70                  75                  80 ccc cag gcg gcc ggc ttc ccc ggc gcg ggc gag tcc ttc ccg ccg ccc     288
Pro Gln Ala Ala Gly Phe Pro Gly Ala Gly Glu Ser Phe Pro Pro Pro
                85                  90                  95 gcg gac gcc gag ggc tac cag ccg ggc gag ggc tac gcc gcc ccg gac     336
Ala Asp Ala Glu Gly Tyr Gln Pro Gly Glu Gly Tyr Ala Ala Pro Asp
            100                 105                 110 ccg cgc gcc ggg ctc tac ccg ggg ccg cgt gag gac tac gcg cta ccc     384
Pro Arg Ala Gly Leu Tyr Pro Gly Pro Arg Glu Asp Tyr Ala Leu Pro
        115                 120                 125 gcg gga ctg gag gtg tcg ggg aaa ctg agg gtc gcg ctc aac aac cac     432
```

```
                Ala Gly Leu Glu Val Ser Gly Lys Leu Arg Val Ala Leu Asn Asn His
                    130                 135                 140 ctg ttg tgg tcc aag ttt aat cag cac cag aca gag atg atc atc acc           480
Leu Leu Trp Ser Lys Phe Asn Gln His Gln Thr Glu Met Ile Ile Thr
145                 150                 155                 160 aag cag gga cgg cgg atg ttc cca ttc ctg tca ttt act gtg gcc ggg           528
Lys Gln Gly Arg Arg Met Phe Pro Phe Leu Ser Phe Thr Val Ala Gly
                165                 170                 175 ctg gag ccc acc agc cac tac agg atg ttt gtg gac gtg gtc ttg gtg           576
Leu Glu Pro Thr Ser His Tyr Arg Met Phe Val Asp Val Val Leu Val
            180                 185                 190 gac cag cac cac tgg cgg tac cag agc ggc aag tgg gtg cag tgt gga           624
Asp Gln His His Trp Arg Tyr Gln Ser Gly Lys Trp Val Gln Cys Gly
        195                 200                 205 aag gcc gag ggc agc atg cca gga aac cgc ctg tac gtc cac ccg gac           672
Lys Ala Glu Gly Ser Met Pro Gly Asn Arg Leu Tyr Val His Pro Asp
210                 215                 220 tcc ccc aac aca gga gcg cac tgg atg cgc cag gaa gtt tca ttt ggg           720
Ser Pro Asn Thr Gly Ala His Trp Met Arg Gln Glu Val Ser Phe Gly
225                 230                 235                 240 aaa cta aag ctc aca aac aac aag ggg gcg tcc aac aat gtg acc cag           768
Lys Leu Lys Leu Thr Asn Asn Lys Gly Ala Ser Asn Asn Val Thr Gln
                245                 250                 255 atg att gtg ctc cag tcc ctc cat aag tac cag ccc cgg ctg cat atc           816
Met Ile Val Leu Gln Ser Leu His Lys Tyr Gln Pro Arg Leu His Ile
                260                 265                 270 gtt gag gtg aac gac gga gag cca gag gca gcc tgc aac gct tcc aac           864
Val Glu Val Asn Asp Gly Glu Pro Glu Ala Ala Cys Asn Ala Ser Asn
            275                 280                 285 acg cat atc ttt act ttc caa gaa acc cag ttc att gcc gtg act gcc           912
Thr His Ile Phe Thr Phe Gln Glu Thr Gln Phe Ile Ala Val Thr Ala
        290                 295                 300 tac cag aat gcc gag att act cag ctg aaa att gat aat aac ccc ttt           960
Tyr Gln Asn Ala Glu Ile Thr Gln Leu Lys Ile Asp Asn Asn Pro Phe
305                 310                 315                 320 gcc aaa gga ttc cgg gag aac ttt gag tcc atg tac aca tct gtt gac          1008
Ala Lys Gly Phe Arg Glu Asn Phe Glu Ser Met Tyr Thr Ser Val Asp
                325                 330                 335 acc agc atc ccc tcc ccg cct gga ccc aac tgt caa ttc ctt ggg gga          1056
Thr Ser Ile Pro Ser Pro Pro Gly Pro Asn Cys Gln Phe Leu Gly Gly
                340                 345                 350 gat cac tac tct cct ctc cta ccc aac cag tat cct gtt ccc agc cgc          1104
Asp His Tyr Ser Pro Leu Leu Pro Asn Gln Tyr Pro Val Pro Ser Arg
            355                 360                 365 ttc tac ccc gac ctt cct ggc cag gcg aag gat gtg gtt ccc cag gct          1152
Phe Tyr Pro Asp Leu Pro Gly Gln Ala Lys Asp Val Val Pro Gln Ala
        370                 375                 380 tac tgg ctg ggg gcc ccc cgg gac cac agc tat gag gct gag ttt cga          1200
Tyr Trp Leu Gly Ala Pro Arg Asp His Ser Tyr Glu Ala Glu Phe Arg
385                 390                 395                 400 gca gtc agc atg aag cct gca ttc ttg ccc tct gcc cct ggg ccc acc          1248
Ala Val Ser Met Lys Pro Ala Phe Leu Pro Ser Ala Pro Gly Pro Thr
                405                 410                 415 atg tcc tac tac cga ggc cag gag gtc ctg gca cct gga gct ggc tgg          1296
Met Ser Tyr Tyr Arg Gly Gln Glu Val Leu Ala Pro Gly Ala Gly Trp
                420                 425                 430 cct gtg gca ccc cag tac cct ccc aag atg ggc ccg gcc agc tgg ttc          1344
Pro Val Ala Pro Gln Tyr Pro Pro Lys Met Gly Pro Ala Ser Trp Phe
            435                 440                 445
```

-continued

```
cgc cct atg cgg act ctg ccc atg gaa ccc ggc cct gga ggc tca gag    1392
Arg Pro Met Arg Thr Leu Pro Met Glu Pro Gly Pro Gly Gly Ser Glu
    450                 455                 460 gga cgg gga cca gag gac cag ggt ccc ccc ttg gtg tgg act gag att    1440
Gly Arg Gly Pro Glu Asp Gln Gly Pro Pro Leu Val Trp Thr Glu Ile
465                 470                 475                 480 gcc ccc atc cgg ccg gaa tcc agt gat tca gga ctg gcc gaa gga gac    1488
Ala Pro Ile Arg Pro Glu Ser Ser Asp Ser Gly Leu Gly Glu Gly Asp
                485                 490                 495 tct aag agg agg cgc gtg tcc ccc tat cct tcc agt ggt gac agc tcc    1536
Ser Lys Arg Arg Arg Val Ser Pro Tyr Pro Ser Ser Gly Asp Ser Ser
            500                 505                 510 tcc cct gct ggg gcc cct tct cct ttt gat aag gaa gct gaa gga cag    1584
Ser Pro Ala Gly Ala Pro Ser Pro Phe Asp Lys Glu Ala Glu Gly Gln
        515                 520                 525 ttt tat aac tat ttt ccc aac tga                                    1608
Phe Tyr Asn Tyr Phe Pro Asn
    530                 535

<210> SEQ ID NO 2
<211> LENGTH: 535
<212> TYPE: PRT
<213> ORGANISM: Homo sapiens

<400> SEQUENCE: 2

Met Gly Ile Val Glu Pro Gly Cys Gly Asp Met Leu Thr Gly Thr Glu
1               5                   10                  15

Pro Met Pro Gly Ser Asp Glu Gly Arg Ala Pro Gly Ala Asp Pro Gln
            20                  25                  30

His Arg Tyr Phe Tyr Pro Glu Pro Gly Ala Gln Asp Ala Asp Glu Arg
        35                  40                  45

Arg Gly Gly Gly Ser Leu Gly Ser Pro Tyr Pro Gly Gly Ala Leu Val
    50                  55                  60

Pro Ala Pro Pro Ser Arg Phe Leu Gly Ala Tyr Ala Tyr Pro Pro Arg
65                  70                  75                  80

Pro Gln Ala Ala Gly Phe Pro Gly Ala Gly Glu Ser Phe Pro Pro Pro
                85                  90                  95

Ala Asp Ala Glu Gly Tyr Gln Pro Gly Glu Gly Tyr Ala Ala Pro Asp
            100                 105                 110

Pro Arg Ala Gly Leu Tyr Pro Gly Pro Arg Glu Asp Tyr Ala Leu Pro
        115                 120                 125

Ala Gly Leu Glu Val Ser Gly Lys Leu Arg Val Ala Leu Asn Asn His
    130                 135                 140

Leu Leu Trp Ser Lys Phe Asn Gln His Gln Thr Glu Met Ile Ile Thr
145                 150                 155                 160

Lys Gln Gly Arg Arg Met Phe Pro Phe Leu Ser Phe Thr Val Ala Gly
                165                 170                 175

Leu Glu Pro Thr Ser His Tyr Arg Met Phe Val Asp Val Val Leu Val
            180                 185                 190

Asp Gln His His Trp Arg Tyr Gln Ser Gly Lys Trp Val Gln Cys Gly
        195                 200                 205

Lys Ala Glu Gly Ser Met Pro Gly Asn Arg Leu Tyr Val His Pro Asp
    210                 215                 220

Ser Pro Asn Thr Gly Ala His Trp Met Arg Gln Glu Val Ser Phe Gly
225                 230                 235                 240

Lys Leu Lys Leu Thr Asn Asn Lys Gly Ala Ser Asn Asn Val Thr Gln
                245                 250                 255
```

```
Met Ile Val Leu Gln Ser Leu His Lys Tyr Gln Pro Arg Leu His Ile
        260                 265                 270

Val Glu Val Asn Asp Gly Glu Pro Glu Ala Ala Cys Asn Ala Ser Asn
            275                 280                 285

Thr His Ile Phe Thr Phe Gln Glu Thr Gln Phe Ile Ala Val Thr Ala
        290                 295                 300

Tyr Gln Asn Ala Glu Ile Thr Gln Leu Lys Ile Asp Asn Asn Pro Phe
305                 310                 315                 320

Ala Lys Gly Phe Arg Glu Asn Phe Glu Ser Met Tyr Thr Ser Val Asp
                325                 330                 335

Thr Ser Ile Pro Ser Pro Gly Pro Asn Cys Gln Phe Leu Gly Gly
        340                 345                 350

Asp His Tyr Ser Pro Leu Leu Pro Asn Gln Tyr Pro Val Pro Ser Arg
            355                 360                 365

Phe Tyr Pro Asp Leu Pro Gly Gln Ala Lys Asp Val Val Pro Gln Ala
370                 375                 380

Tyr Trp Leu Gly Ala Pro Arg Asp His Ser Tyr Glu Ala Glu Phe Arg
385                 390                 395                 400

Ala Val Ser Met Lys Pro Ala Phe Leu Pro Ser Ala Pro Gly Pro Thr
                405                 410                 415

Met Ser Tyr Tyr Arg Gly Gln Glu Val Leu Ala Pro Gly Ala Gly Trp
            420                 425                 430

Pro Val Ala Pro Gln Tyr Pro Pro Lys Met Gly Pro Ala Ser Trp Phe
                435                 440                 445

Arg Pro Met Arg Thr Leu Pro Met Glu Pro Gly Pro Gly Gly Ser Glu
    450                 455                 460

Gly Arg Gly Pro Glu Asp Gln Gly Pro Pro Leu Val Trp Thr Glu Ile
465                 470                 475                 480

Ala Pro Ile Arg Pro Glu Ser Ser Asp Ser Gly Leu Gly Glu Gly Asp
                485                 490                 495

Ser Lys Arg Arg Arg Val Ser Pro Tyr Pro Ser Ser Gly Asp Ser Ser
            500                 505                 510

Ser Pro Ala Gly Ala Pro Ser Pro Phe Asp Lys Glu Ala Glu Gly Gln
        515                 520                 525

Phe Tyr Asn Tyr Phe Pro Asn
        530                 535

<210> SEQ ID NO 3
<211> LENGTH: 1593
<212> TYPE: DNA
<213> ORGANISM: Mus musculus
<220> FEATURE:
<221> NAME/KEY: CDS
<222> LOCATION: (1)..(1590)

<400> SEQUENCE: 3 atg ggc atc gtg gag ccg ggc tgc gga gac atg ctg acc ggc acc gag    48
Met Gly Ile Val Glu Pro Gly Cys Gly Asp Met Leu Thr Gly Thr Glu
 1               5                  10                  15 ccg atg ccg agt gac gag ggc cgg ggg ccc gga gcg gac caa cag cat    96
Pro Met Pro Ser Asp Glu Gly Arg Gly Pro Gly Ala Asp Gln Gln His
            20                  25                  30 cgt ttc ttc tat ccc gag ccg ggc gca cag gac ccg acc gat cgc cgc   144
Arg Phe Phe Tyr Pro Glu Pro Gly Ala Gln Asp Pro Thr Asp Arg Arg
        35                  40                  45 gca ggt agc agc ctg ggg acg ccc tac tct ggg ggc gcc ctg gtg cct   192
```

-continued

```
                Ala Gly Ser Ser Leu Gly Thr Pro Tyr Ser Gly Gly Ala Leu Val Pro
                     50                  55                  60 gcc gcg ccg ggt cgc ttc ctt gga tcc ttc gcc tac ccg ccc cgg gct         240
Ala Ala Pro Gly Arg Phe Leu Gly Ser Phe Ala Tyr Pro Pro Arg Ala
 65                  70                  75                  80 cag gtg gct ggc ttt ccc ggg cct ggc gag ttc ttc ccg ccg ccc gcg         288
Gln Val Ala Gly Phe Pro Gly Pro Gly Glu Phe Phe Pro Pro Pro Ala
                 85                  90                  95 ggt gcg gag ggc tac ccg ccc gtg gat ggc tac cct gcc cct gac ccg         336
Gly Ala Glu Gly Tyr Pro Pro Val Asp Gly Tyr Pro Ala Pro Asp Pro
             100                 105                 110 cgc gcg ggg ctc tac cca ggg ccg cgc gag gac tac gca ttg ccc gcg         384
Arg Ala Gly Leu Tyr Pro Gly Pro Arg Glu Asp Tyr Ala Leu Pro Ala
         115                 120                 125 ggg ttg gag gtg tct ggg aag ctg aga gtc gcg ctc agc aac cac ctg         432
Gly Leu Glu Val Ser Gly Lys Leu Arg Val Ala Leu Ser Asn His Leu
     130                 135                 140 ttg tgg tcc aag ttc aac cag cac cag aca gag atg atc atc act aag         480
Leu Trp Ser Lys Phe Asn Gln His Gln Thr Glu Met Ile Ile Thr Lys
145                 150                 155                 160 caa gga cgg cga atg ttc cca ttc ctg tcc ttc acc gtg gcc ggg ctg         528
Gln Gly Arg Arg Met Phe Pro Phe Leu Ser Phe Thr Val Ala Gly Leu
                 165                 170                 175 gag ccc aca agc cat tac agg atg ttt gtg gat gtg gtc ttg gtg gac         576
Glu Pro Thr Ser His Tyr Arg Met Phe Val Asp Val Val Leu Val Asp
             180                 185                 190 cag cac cac tgg cgg tac cag agc ggc aag tgg gtg cag tgt gga aag         624
Gln His His Trp Arg Tyr Gln Ser Gly Lys Trp Val Gln Cys Gly Lys
         195                 200                 205 gca gaa ggc agc atg cca ggg aac cgc tta tat gtc cac cca gac tcc         672
Ala Glu Gly Ser Met Pro Gly Asn Arg Leu Tyr Val His Pro Asp Ser
     210                 215                 220 ccc aac acc gga gcc cac tgg atg cgc cag gaa gtt tca ttt ggg aag         720
Pro Asn Thr Gly Ala His Trp Met Arg Gln Glu Val Ser Phe Gly Lys
225                 230                 235                 240 cta aag ctc acc aac aac aag ggg gct tcc aac aat gtg acc cag atg         768
Leu Lys Leu Thr Asn Asn Lys Gly Ala Ser Asn Asn Val Thr Gln Met
                 245                 250                 255 atc gtc ctg cag tct ctc cac aag tac cag ccc cgg ctg cac atc gtg         816
Ile Val Leu Gln Ser Leu His Lys Tyr Gln Pro Arg Leu His Ile Val
             260                 265                 270 gag gtg aat gat gga gag cca gag gct gcc tgc agt gct tct aac aca         864
Glu Val Asn Asp Gly Glu Pro Glu Ala Ala Cys Ser Ala Ser Asn Thr
         275                 280                 285 cac gtc ttt act ttc caa gag acc cag ttc att gca gtg act gcc tac         912
His Val Phe Thr Phe Gln Glu Thr Gln Phe Ile Ala Val Thr Ala Tyr
     290                 295                 300 cag aac gca gag atc act cag ctg aaa atc gac aac aac ccc ttt gcc         960
Gln Asn Ala Glu Ile Thr Gln Leu Lys Ile Asp Asn Asn Pro Phe Ala
305                 310                 315                 320 aaa gga ttc cgg gag aac ttt gag tcc atg tac gca tct gtt gat acg        1008
Lys Gly Phe Arg Glu Asn Phe Glu Ser Met Tyr Ala Ser Val Asp Thr
                 325                 330                 335 agt gtc ccc tcg cca cct gga ccc aac tgt caa ctg ctt ggg gga gac        1056
Ser Val Pro Ser Pro Pro Gly Pro Asn Cys Gln Leu Leu Gly Gly Asp
             340                 345                 350 ccc ttc tca cct ctt cta tcc aac cag tat cct gtt ccc agc cgt ttc        1104
Pro Phe Ser Pro Leu Leu Ser Asn Gln Tyr Pro Val Pro Ser Arg Phe
         355                 360                 365
```

```
tac ccc gac ctt cca ggc cag ccc aag gat atg atc tca cag cct tac    1152
Tyr Pro Asp Leu Pro Gly Gln Pro Lys Asp Met Ile Ser Gln Pro Tyr
    370                 375                 380 tgg ctg ggg aca cct cgg gaa cac agt tat gaa gcg gag ttc cga gct    1200
Trp Leu Gly Thr Pro Arg Glu His Ser Tyr Glu Ala Glu Phe Arg Ala
385                 390                 395                 400 gtg agc atg aag ccc aca ctc cta ccc tct gcc ccg ggc ccc act gtg    1248
Val Ser Met Lys Pro Thr Leu Leu Pro Ser Ala Pro Gly Pro Thr Val
                405                 410                 415 ccc tac tac cgg ggc caa gac gtc ctg gcg cct gga gct ggt tgg ccc    1296
Pro Tyr Tyr Arg Gly Gln Asp Val Leu Ala Pro Gly Ala Gly Trp Pro
            420                 425                 430 gtg gcc cct caa tac ccg ccc aag atg agc cca gct ggc tgg ttc cgg    1344
Val Ala Pro Gln Tyr Pro Pro Lys Met Ser Pro Ala Gly Trp Phe Arg
        435                 440                 445 ccc atg cga act ctg ccc atg gac ccg ggc ctg gga tcc tca gag gaa    1392
Pro Met Arg Thr Leu Pro Met Asp Pro Gly Leu Gly Ser Ser Glu Glu
450                 455                 460 cag ggc tcc tcc ccc tcg ctg tgg cct gag gtc acc tcc ctc cag ccg    1440
Gln Gly Ser Ser Pro Ser Leu Trp Pro Glu Val Thr Ser Leu Gln Pro
465                 470                 475                 480 gag ccc agc gac tca gga cta ggc gaa gga gac act aag agg agg agg    1488
Glu Pro Ser Asp Ser Gly Leu Gly Glu Gly Asp Thr Lys Arg Arg Arg
                485                 490                 495 ata tcc ccc tat cct tcc agt ggc gac agc tcc tct ccc gct ggg gcc    1536
Ile Ser Pro Tyr Pro Ser Ser Gly Asp Ser Ser Ser Pro Ala Gly Ala
            500                 505                 510 cct tct cct ttt gat aag gaa acc gaa ggc cag ttt tat aat tat ttt    1584
Pro Ser Pro Phe Asp Lys Glu Thr Glu Gly Gln Phe Tyr Asn Tyr Phe
        515                 520                 525 ccc aac tga                                                        1593
Pro Asn
530

<210> SEQ ID NO 4
<211> LENGTH: 530
<212> TYPE: PRT
<213> ORGANISM: Mus musculus

<400> SEQUENCE: 4

Met Gly Ile Val Glu Pro Gly Cys Gly Asp Met Leu Thr Gly Thr Glu
1               5                   10                  15

Pro Met Pro Ser Asp Glu Gly Arg Gly Pro Gly Ala Asp Gln Gln His
            20                  25                  30

Arg Phe Phe Tyr Pro Glu Pro Gly Ala Gln Asp Pro Thr Asp Arg Arg
        35                  40                  45

Ala Gly Ser Ser Leu Gly Thr Pro Tyr Ser Gly Gly Ala Leu Val Pro
    50                  55                  60

Ala Ala Pro Gly Arg Phe Leu Gly Ser Phe Ala Tyr Pro Pro Arg Ala
65                  70                  75                  80

Gln Val Ala Gly Phe Pro Gly Pro Gly Glu Phe Phe Pro Pro Pro Ala
                85                  90                  95

Gly Ala Glu Gly Tyr Pro Pro Val Asp Gly Tyr Pro Ala Pro Asp Pro
            100                 105                 110

Arg Ala Gly Leu Tyr Pro Gly Pro Arg Glu Asp Tyr Ala Leu Pro Ala
        115                 120                 125

Gly Leu Glu Val Ser Gly Lys Leu Arg Val Ala Leu Ser Asn His Leu
    130                 135                 140
```

```
Leu Trp Ser Lys Phe Asn Gln His Gln Thr Glu Met Ile Ile Thr Lys
145                 150                 155                 160

Gln Gly Arg Arg Met Phe Pro Phe Leu Ser Phe Thr Val Ala Gly Leu
                165                 170                 175

Glu Pro Thr Ser His Tyr Arg Met Phe Val Asp Val Val Leu Val Asp
            180                 185                 190

Gln His His Trp Arg Tyr Gln Ser Gly Lys Trp Val Gln Cys Gly Lys
        195                 200                 205

Ala Glu Gly Ser Met Pro Gly Asn Arg Leu Tyr Val His Pro Asp Ser
    210                 215                 220

Pro Asn Thr Gly Ala His Trp Met Arg Gln Glu Val Ser Phe Gly Lys
225                 230                 235                 240

Leu Lys Leu Thr Asn Asn Lys Gly Ala Ser Asn Asn Val Thr Gln Met
                245                 250                 255

Ile Val Leu Gln Ser Leu His Lys Tyr Gln Pro Arg Leu His Ile Val
            260                 265                 270

Glu Val Asn Asp Gly Glu Pro Glu Ala Ala Cys Ser Ala Ser Asn Thr
        275                 280                 285

His Val Phe Thr Phe Gln Glu Thr Gln Phe Ile Ala Val Thr Ala Tyr
    290                 295                 300

Gln Asn Ala Glu Ile Thr Gln Leu Lys Ile Asp Asn Asn Pro Phe Ala
305                 310                 315                 320

Lys Gly Phe Arg Glu Asn Phe Glu Ser Met Tyr Ala Ser Val Asp Thr
                325                 330                 335

Ser Val Pro Ser Pro Gly Pro Asn Cys Gln Leu Leu Gly Gly Asp
            340                 345                 350

Pro Phe Ser Pro Leu Leu Ser Asn Gln Tyr Pro Val Pro Ser Arg Phe
    355                 360                 365

Tyr Pro Asp Leu Pro Gly Gln Pro Lys Asp Met Ile Ser Gln Pro Tyr
    370                 375                 380

Trp Leu Gly Thr Pro Arg Glu His Ser Tyr Glu Ala Glu Phe Arg Ala
385                 390                 395                 400

Val Ser Met Lys Pro Thr Leu Leu Pro Ser Ala Pro Gly Pro Thr Val
                405                 410                 415

Pro Tyr Tyr Arg Gly Gln Asp Val Leu Ala Pro Gly Ala Gly Trp Pro
            420                 425                 430

Val Ala Pro Gln Tyr Pro Pro Lys Met Ser Pro Ala Gly Trp Phe Arg
        435                 440                 445

Pro Met Arg Thr Leu Pro Met Asp Pro Gly Leu Gly Ser Ser Glu Glu
    450                 455                 460

Gln Gly Ser Ser Pro Ser Leu Trp Pro Glu Val Thr Ser Leu Gln Pro
465                 470                 475                 480

Glu Pro Ser Asp Ser Gly Leu Gly Glu Gly Asp Thr Lys Arg Arg Arg
                485                 490                 495

Ile Ser Pro Tyr Pro Ser Ser Gly Asp Ser Ser Ser Pro Ala Gly Ala
            500                 505                 510

Pro Ser Pro Phe Asp Lys Glu Thr Glu Gly Gln Phe Tyr Asn Tyr Phe
        515                 520                 525

Pro Asn
    530

<210> SEQ ID NO 5
<211> LENGTH: 27
<212> TYPE: DNA
```

-continued

```
<213> ORGANISM: Artificial Sequence
<220> FEATURE:
<223> OTHER INFORMATION: Synthetic oligonucleotide

<400> SEQUENCE: 5
gggaatttca cacctaggtg aaattcc                                           27

<210> SEQ ID NO 6
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 6
aatttcacac ctaggtgtga aatt                                              24

<210> SEQ ID NO 7
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 7
gagctatcac ctaagtgtgg gcta                                              24

<210> SEQ ID NO 8
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 8
aaactgccac ctaagtgtgg gcta                                              24

<210> SEQ ID NO 9
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 9
aaactgctgt ctaaacatgg gcta                                              24
```